US012350297B2

(12) United States Patent
Danino et al.

(10) Patent No.: US 12,350,297 B2
(45) Date of Patent: Jul. 8, 2025

(54) PROGRAMMABLE BACTERIA FOR THE TREATMENT OF CANCER

(71) Applicant: The Trustees of Columbia University in the City of New York, New York, NY (US)

(72) Inventors: Tal Danino, New York, NY (US); Nicholas Arpaia, New York, NY (US); Sreyan Chowdhury, New York, NY (US); Candice Gurbatri, New York, NY (US)

(73) Assignees: THE TRUSTEES OF COLUMBIA UNIVERSITY IN THE CITY OF NEW YORK, New York, NY (US); NATIONAL INSTITUTES OF HEALTH (NIH) U.S. DEPT. OF HEALTH AND HUMAN SERVICES (DHHS), Bethesda, MD (US)

( * ) Notice: Subject to any disclaimer, the term of this patent is extended or adjusted under 35 U.S.C. 154(b) by 885 days.

(21) Appl. No.: 17/152,893

(22) Filed: Jan. 20, 2021

(65) Prior Publication Data

US 2021/0308195 A1   Oct. 7, 2021

Related U.S. Application Data

(63) Continuation of application No. PCT/US2019/042795, filed on Jul. 22, 2019.

(60) Provisional application No. 62/700,972, filed on Jul. 20, 2018, provisional application No. 62/747,826, filed on Oct. 19, 2018, provisional application No. 62/773,748, filed on Nov. 30, 2018, provisional application No. 62/834,032, filed on Apr. 15, 2019.

(51) Int. Cl.
| | |
|---|---|
| *A61K 35/74* | (2015.01) |
| *A61P 35/00* | (2006.01) |
| *C07K 14/195* | (2006.01) |
| *C07K 14/52* | (2006.01) |
| *C07K 16/28* | (2006.01) |
| *A61K 39/00* | (2006.01) |

(52) U.S. Cl.
CPC .............. *A61K 35/74* (2013.01); *A61P 35/00* (2018.01); *C07K 14/195* (2013.01); *C07K 14/521* (2013.01); *C07K 16/2803* (2013.01); *C07K 16/2818* (2013.01); *C07K 16/2827* (2013.01); *C07K 16/2896* (2013.01); *A61K 2039/505* (2013.01); *C07K 2317/569* (2013.01)

(58) Field of Classification Search
CPC .................................................. A61K 35/74
See application file for complete search history.

(56) References Cited

U.S. PATENT DOCUMENTS

| | | | |
|---|---|---|---|
| 6,080,849 | A | 6/2000 | Bermudes et al. |
| 9,598,697 | B2 | 3/2017 | Curtiss, III et al. |
| 9,816,083 | B2 | 11/2017 | Lin et al. |
| 2007/0190029 | A1 | 8/2007 | Pardoll |
| 2013/0034907 | A1 | 2/2013 | Collins et al. |
| 2013/0295054 | A1 | 11/2013 | Huang |

FOREIGN PATENT DOCUMENTS

| | | |
|---|---|---|
| WO | WO 2003/063593 | 8/2003 |
| WO | WO 2016/188449 | 1/2016 |
| WO | WO 2016/164636 | 10/2016 |
| WO | WO 2016/210373 | 12/2016 |
| WO | WO 2017/123675 | 7/2017 |
| WO | WO 2017/198212 | 11/2017 |
| WO | 2018129404 A1 | 7/2018 |

OTHER PUBLICATIONS

Silvasubramaniam et al., "Bioengineering microbial communities: Their potential to help, hinder and disgust", Bioengineered, Apr. 26, 2016, vol. 7, No. 3, 137-144.
Tjuvajev et al., "*Salmonella*-based tumor-targeted cancer therapy: tumor amplified protein expression therapy (TAPET) for diagnostic imaging", J Control Release vol. 74/ Issue 1-3, pp. 313-315, Jul. 2001.
Zheng et al., "Optically-controlled bacterial metabolite for cancer therapy", Nat Commun, vol. 9 / Issue 1, pp. 1680, Apr. 2018.
Advani et al. (Nov. 1, 2018) CD47 Blockade by Hu5F9-G4 and Rituximab in Non-Hodgkin's Lymphoma. N Engl J Med 379:1711-1721.
Armstrong et al. (Apr. 15, 2002) Immunization with a recombinant adenovirus encoding a lymphoma idiotype: induction of tumor-protective immunity and identification of an idiotype-specific T cell epitope. J. Immunol. 168, 3983-3991.
Bannas et al. (Nov. 2017) Nanobodies and nanobody-based human heavy Chain antibodies as antitumor therapeutics. Frontiers in immunology 8:1603.
Contardi et al. (May 2005) CTLA-4 is constitutively expressed on tumor cells and can trigger apoptosis upon ligand interaction. International journal of cancer 117(4):538-550.

(Continued)

*Primary Examiner* — Albert M Navarro
(74) *Attorney, Agent, or Firm* — Potomac Law Group, PLLC

(57) ABSTRACT

Disclosed herein are programmable bacteria for tumor-targeted immunotherapeutic delivery. In certain embodiments, the programmable bacteria comprise at least one synchronized lysis circuit contained in a single operon which are capable of being further engineered to cyclically produce anti-cancer therapeutic agents including but not limited to nanobodies against immune checkpoint inhibitors and over-expressed markers in cancers, toxins, tumor antigens, cytokines, and chemokines. In some embodiments, the programmable bacteria comprise at least one synchronized lysis circuit contained in a single operon and at least one plasmid producing a therapeutic agent, i.e., at least one plasmid comprising a nucleic acid sequence which encodes a therapeutic agent. The disclosure also provides methods of curing and treating cancer using the programmable bacteria.

18 Claims, 75 Drawing Sheets

(56) References Cited

OTHER PUBLICATIONS

Danino et al. (Jul. 12, 2012) In vivo gene expression dynamics of tumor-targeted bacteria. ACS synthetic biology 1(10):465-470.
Danino et al. (May 27, 2015) Programmable probiotics for detection of cancer in urine. Science translational medicine 7(289):289ra284.
Derman et al. (2012) Alp7R regulates expression of the actin-like protein Alp7A in Bacillus subtilis. J Bacteriol 194:2715-2724.
Din et al. (Aug. 4, 2016) Synchronized cycles of bacterial lysis for in vivo delivery. Nature 536(7614):81-85.
Fedorec et al. (Jun. 19, 2018) Two new plasmid post-segregational killing mechanisms for the implementation of synthetic gene networks in E. coli. bioRxiv:350744.
Fedorec (Aug. 28, 2014) Mechanisms for Plasmid Maintenance. CoMPLEX, University College London.
Gerdes et al. (Aug. 1986) Mechanism of postsegregational killing by the hok gene product of the parB system of plasmid R1 and its homology with the relF gene product of the E. coli relB operon. EMBO J 5:2023-2029.
Haldimann and Wanner (Nov. 2001) Conditional-replication, integration, excision, and retrieval plasmid-host systems for gene structure-function studies of bacteria. Journal of Bacteriology 183:6384-93.
Hu et al. (Nov. 2017) Nanobody-based delivery systems for diagnosis and targeted tumor therapy. Frontiers in immunology 8:1442.
Huang et al. (Jan. 20, 2017) Targeting CD47: the achievements and concerns of current studies on cancer immunotherapy. J Thorac Dis 9:E168-E174.
Ingram et al. (Sep. 19, 2017) Localized CD47 blockade enhances immunotherapy for murine melanoma. Proc Natl Acad Sci U S A 114:10184-10189.
Kauder et al. (Feb. 21, 2018) ALX148 blocks CD47 and enhances innate and adaptive antitumor immunity with a favorable safety profile. PloS one 13:e0201832.
Kim et al. (Aug. 12, 2014) Eradication of metastatic mouse cancers resistant to immune checkpoint blockade by suppression of myeloid-derived cells. Journal for immunotherapy of cancer 2(3):p. 267.
Kong et al. (Oct. 29, 2007) LPS-induced down-regulation of signal regulatory protein {alpha} contributes Journal of Exp Med vol. 204, No. 11, pp. 2719-2731.
Liu et al. (Oct. 2015) CD47 blockade triggers T cell-mediated destruction of immunogenic tumors. Nat Med 21:1209-1215.
Majeti et al. (Jul. 23, 2009) CD47 is an adverse prognostic factor and therapeutic antibody target on human acute myeloid leukemia stem cells. Cell 138:286-299.
Naidoo et al. (Sep. 1, 2015) Toxicities of the anti-PD-1 and anti-PD-L1 immune checkpoint antibodies. Annals of Oncology 26:2375-2391.
Sagiv-Barfi et al. (Jan. 14, 2015) Therapeutic antitumor immunity by checkpoint blockade is enhanced by ibrutinib, an inhibitor of both BTK and ITK. Proc Natl Acad Sci USA 201500712.
Secher et al. (Sep. 2017) Oral administration of the probiotic strain Escherichia coli Nissle 1917 reduces susceptibility to neuroinflammation and repairs experimental autoimmune encephalomyelitis-induced intestinal barrier dysfunction. Frontiers in immunology 8:1096.
Skinner et al. (Jun. 2013) Measuring mRNA copy number in individual Escherichia coli cells using single-molecule fluorescent in situ hybridization. Nat Protoc 8, 1100-1113.
Sockolosky et al. (Apr. 18, 2016) Durable antitumor responses to CD47 blockade require adaptive immune stimulation. Proc Natl Acad Sci U S A 113, E2646-2654.
Swann and Smyth (May 2007) Immune surveillance of tumors. Journal of Clinical Investigation 117:1137.
Weiskopf et al. (Jul. 5, 2013) Engineered SIRPα Variants as Immunotherapeutic Adjuvants to Anticancer Antibodies. Science 341:88-91.
Willingham et al. (Apr. 24, 2012) The CD47-signal regulatory protein alpha (SIRPa) interaction is a therapeutic target for human solid tumors. Proc Natl Acad Sci U S A 109:6662-6667.
Lee and Jeong (Nov. 2015) Challenges to production of antibodies in bacteria and yeast. Journal of bioscience and bioengineering 120(5):483-490.
Redelman-Sidi et al. (Feb. 4, 2014) The mechanism of action of BCG therapy for bladder cancer—a current perspective. Nature Reviews Urology 11(3):153.
Din et al. 'Synchronized Cycles Of Bacterial Lysis For In Vivo Delivery' Nature, Aug. 4, 2016; vol. 536; pp. 81-93; Supplementary Information pp. 1-10; abstract; figure 1; figure 1 legend; supplementary information p. 7, second paragraph doi: 10 .1038/nature 18930.
Chakraborty et al., "The difficulties in cancer treatment", Ecancermedicalscience. Nov. 1, 20124; 6(16).
Supplementary Search Report issued EP Pat. Appln. No. 19837650.1 dated Apr. 22, 2022.
Zugazagoitia et al., "Current Challenges in Cancer Treatment", Clin Ther. Jul. 2016;38(7):1551-66.

Fig. 1
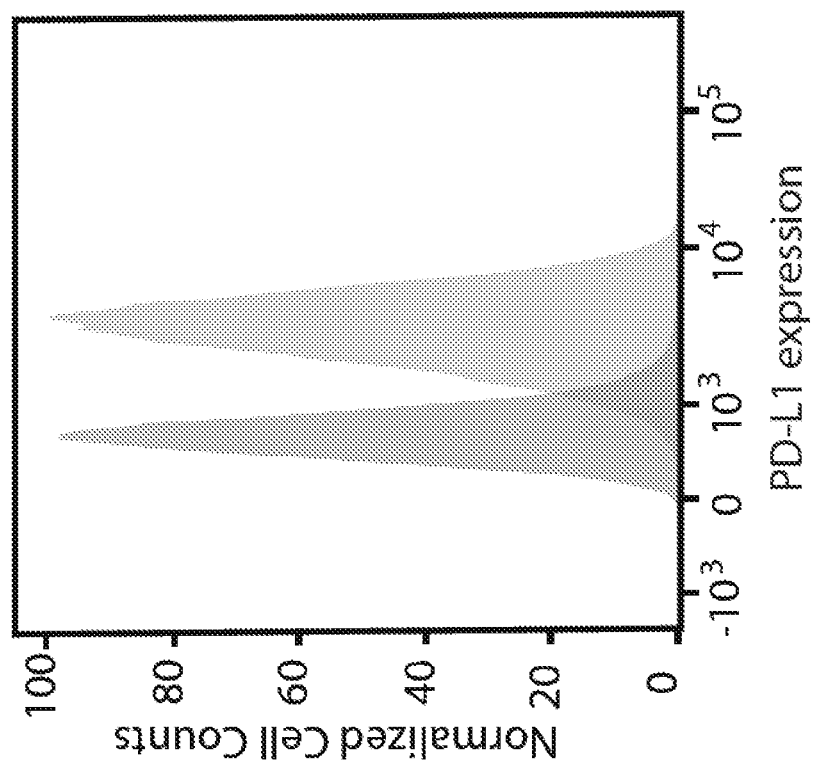
Fig. 1B
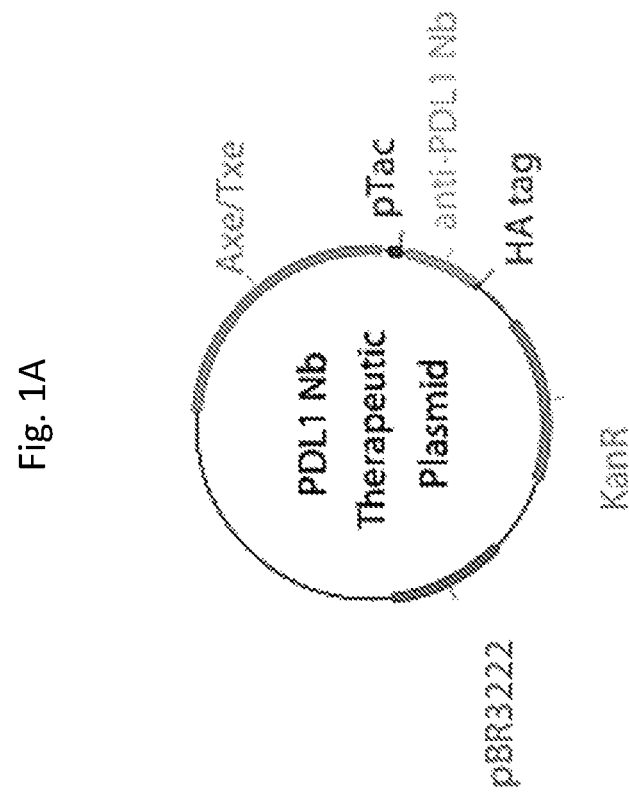
Fig. 1A

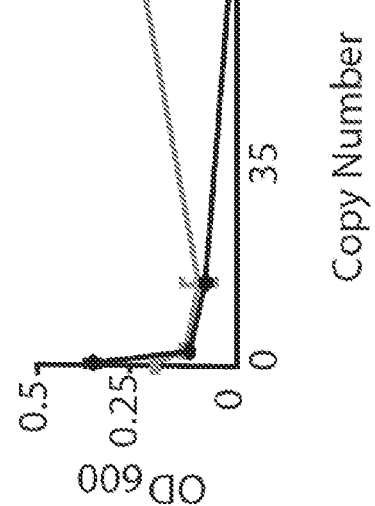
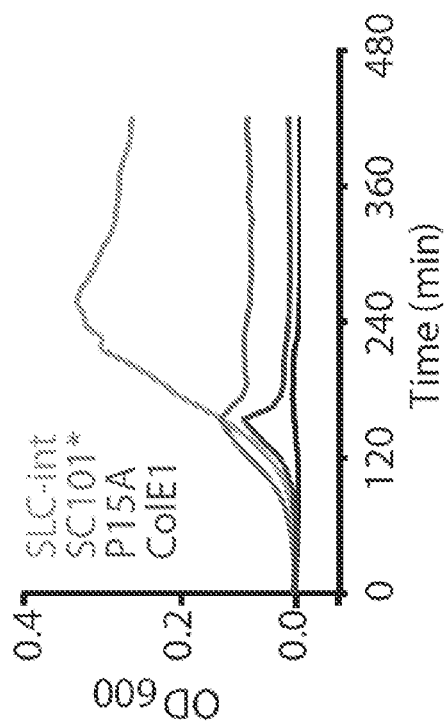
Fig. 2F
Fig. 2E

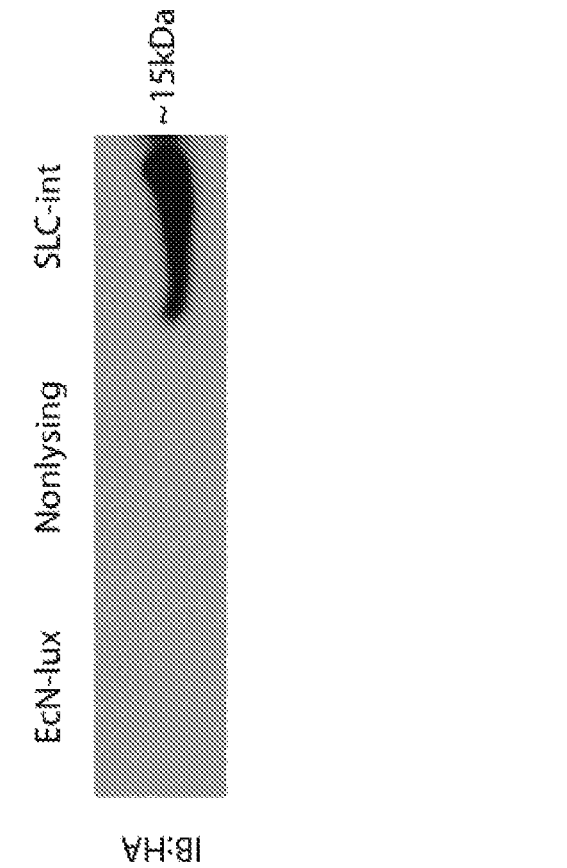

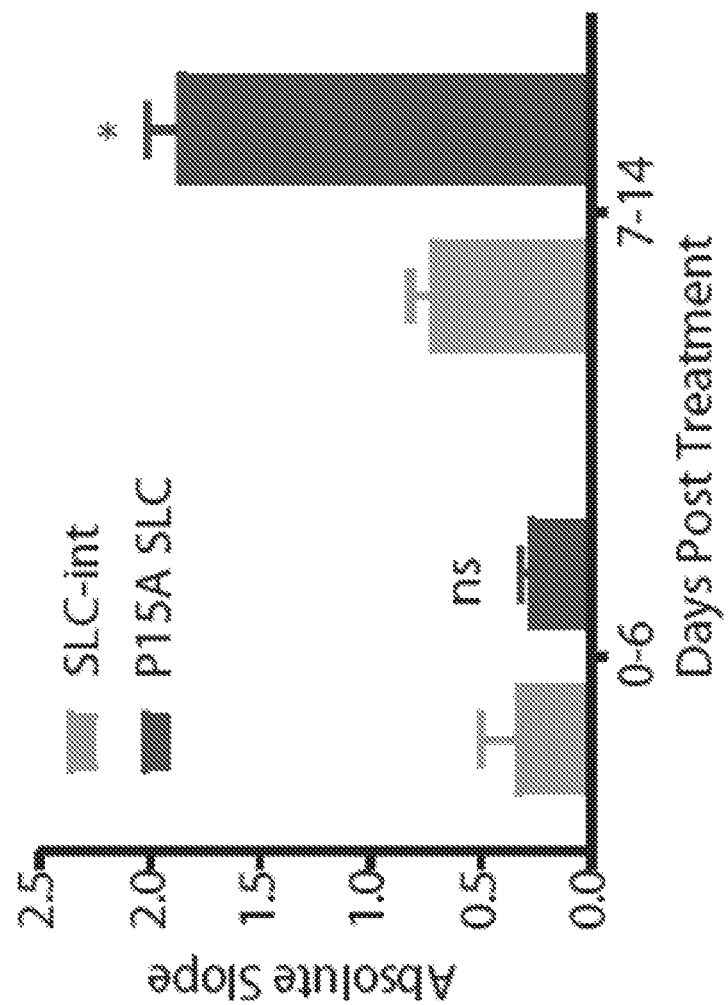

Fig. 4
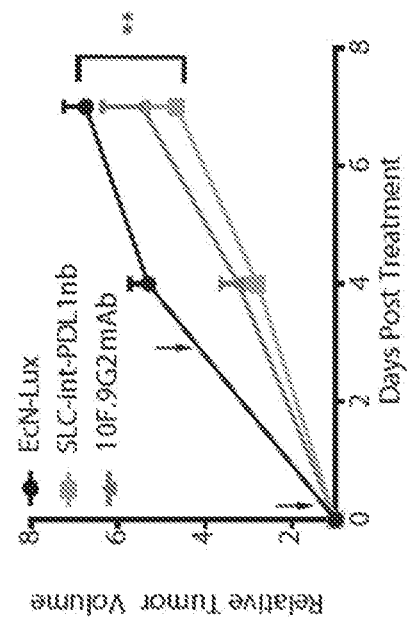
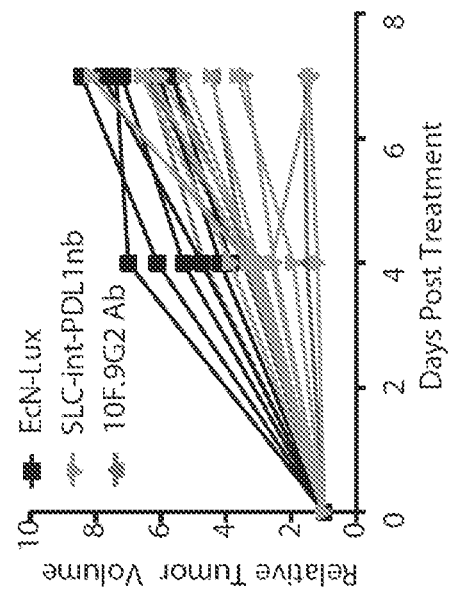
Fig. 4A

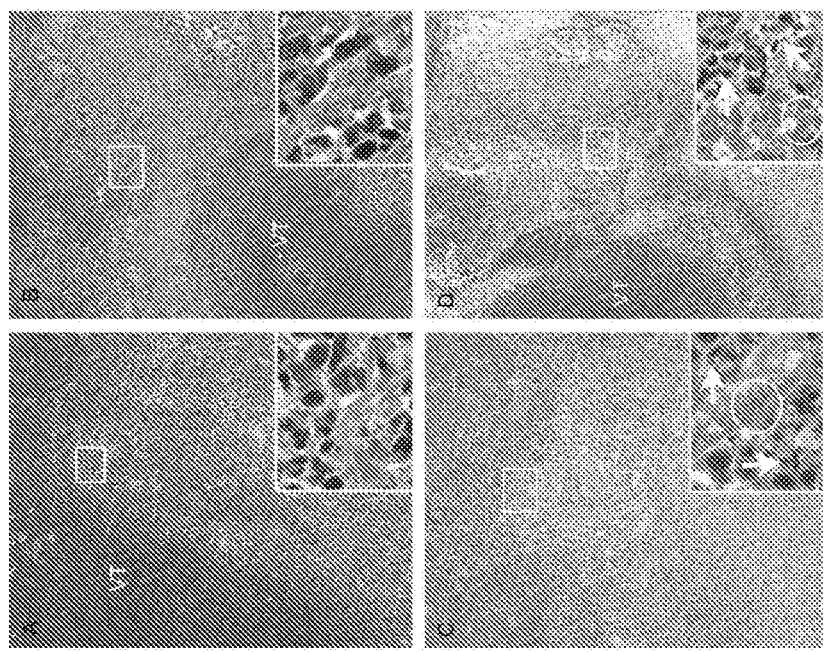
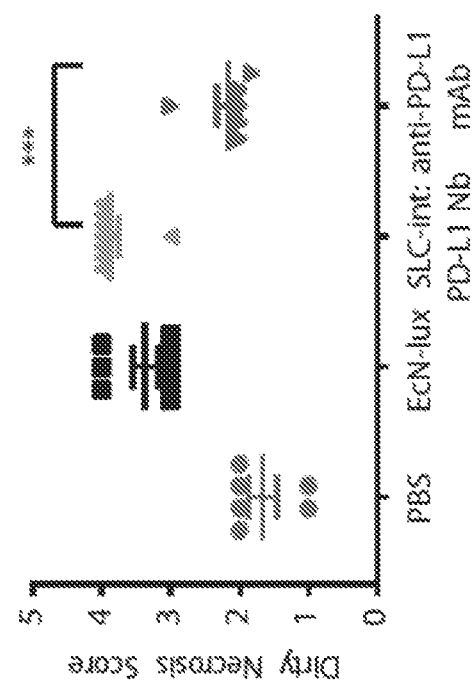
Fig. 4B

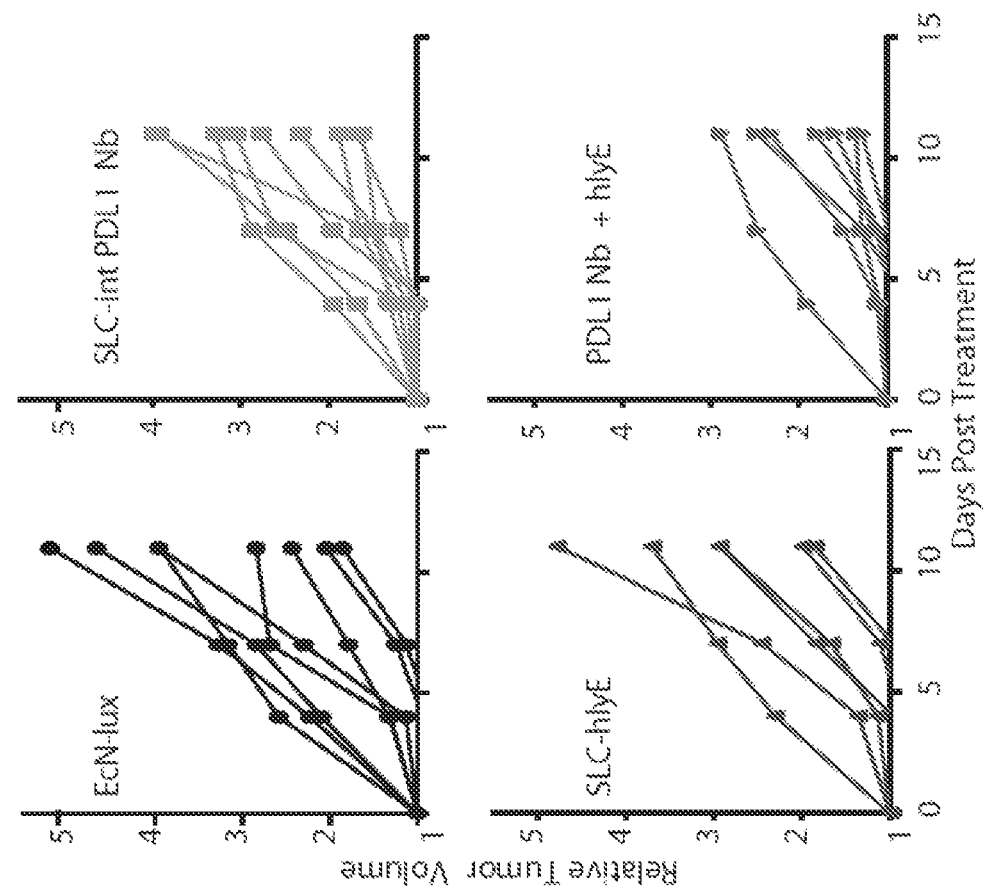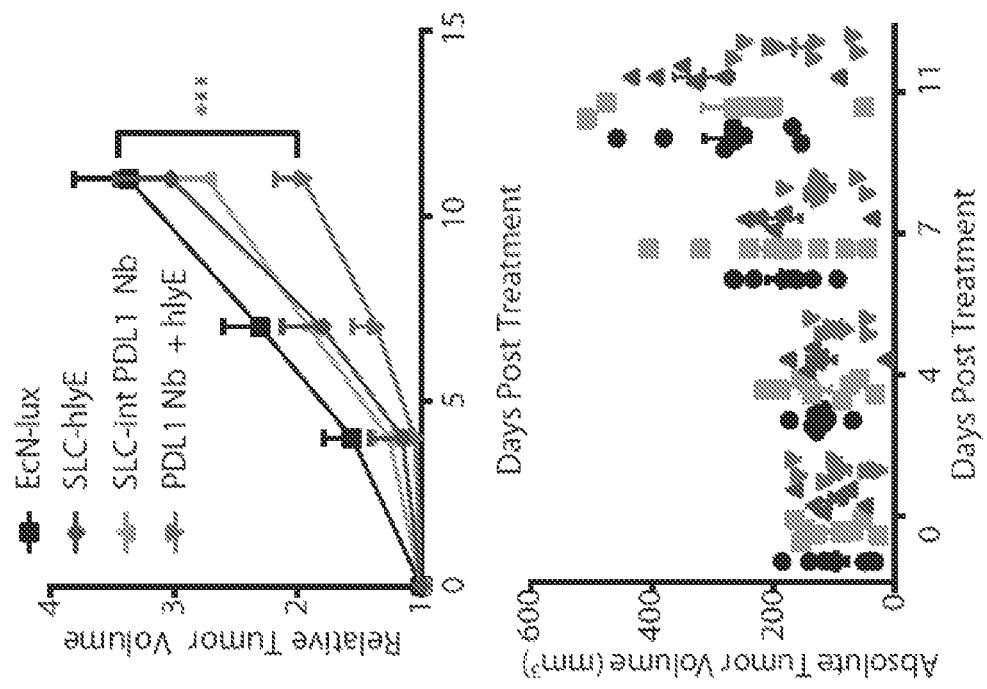

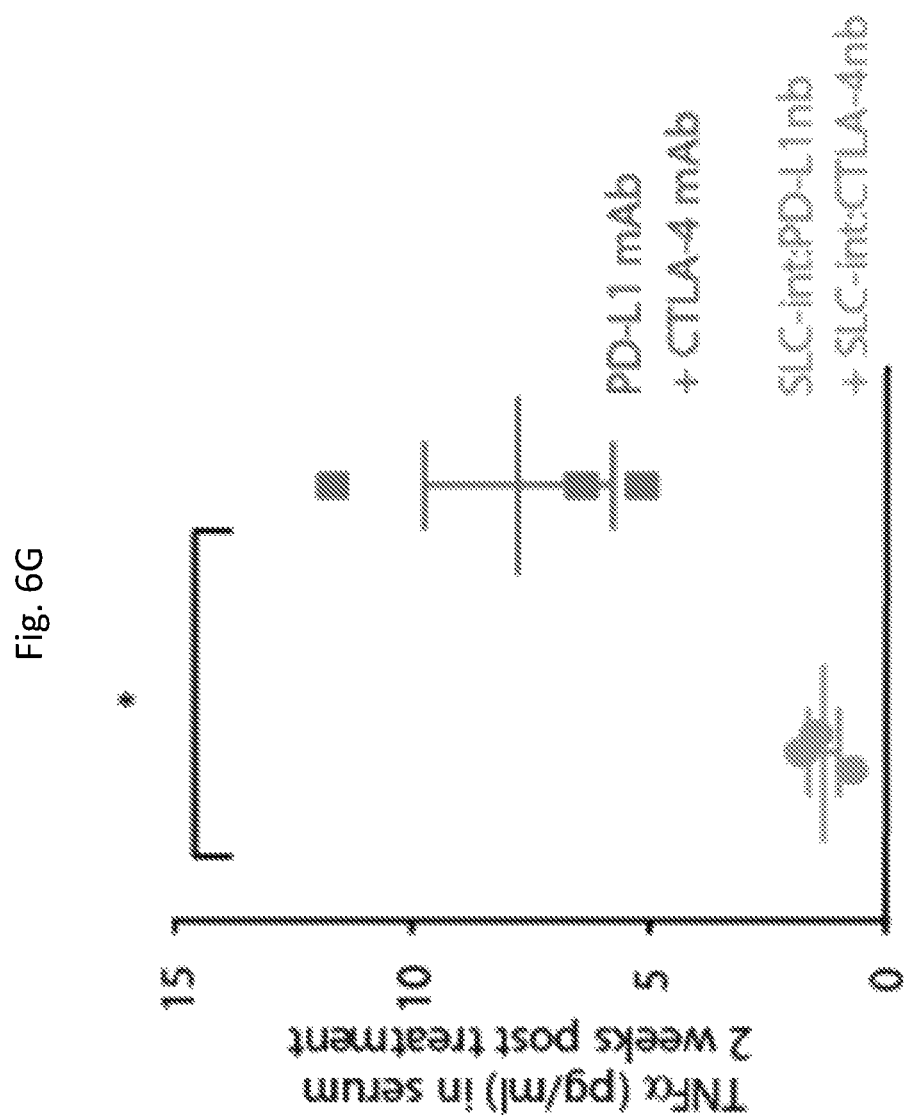

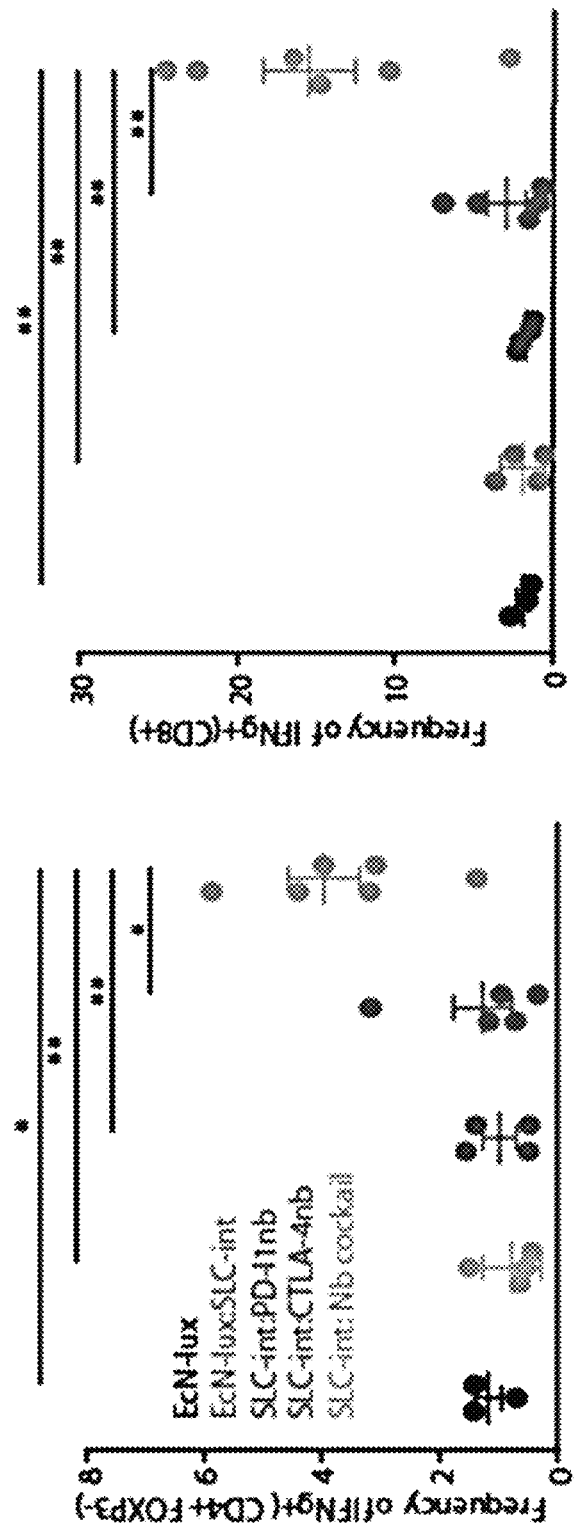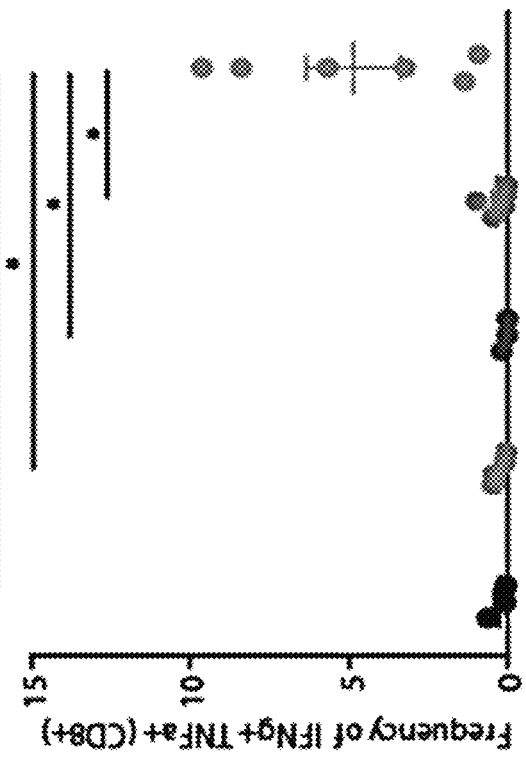
Fig. 6O

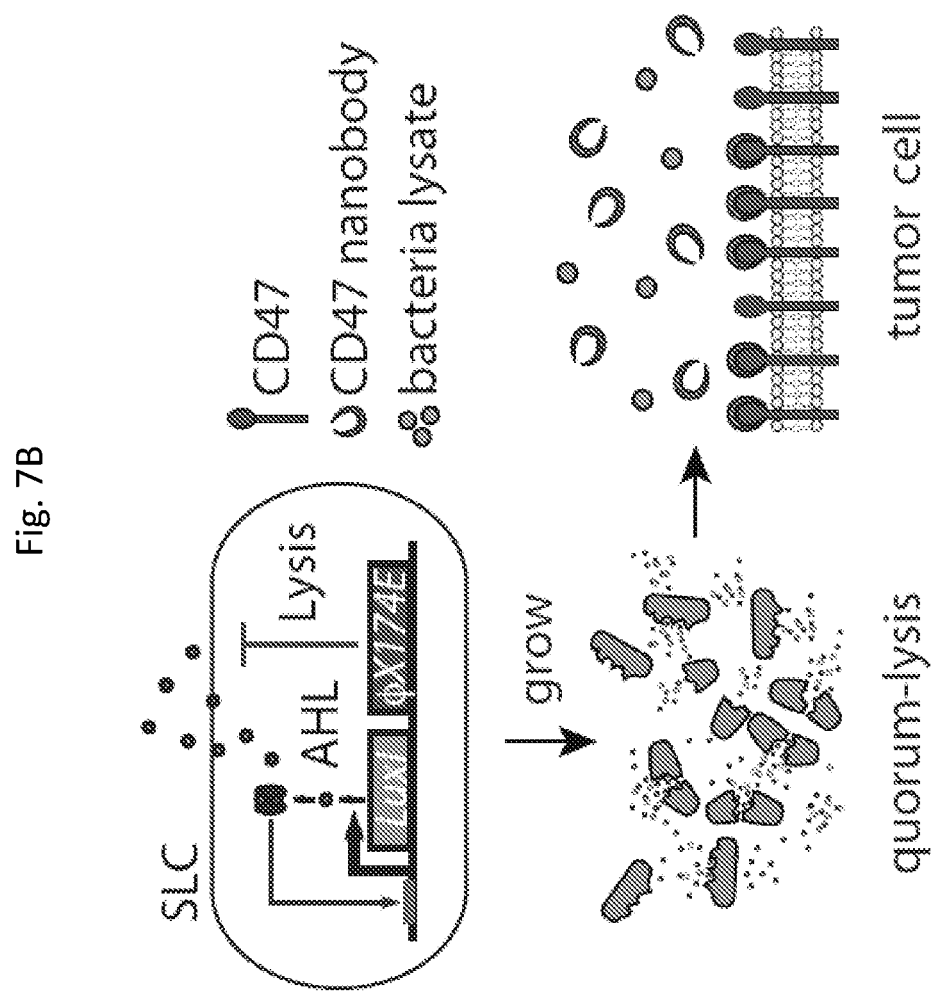

Fig. 9
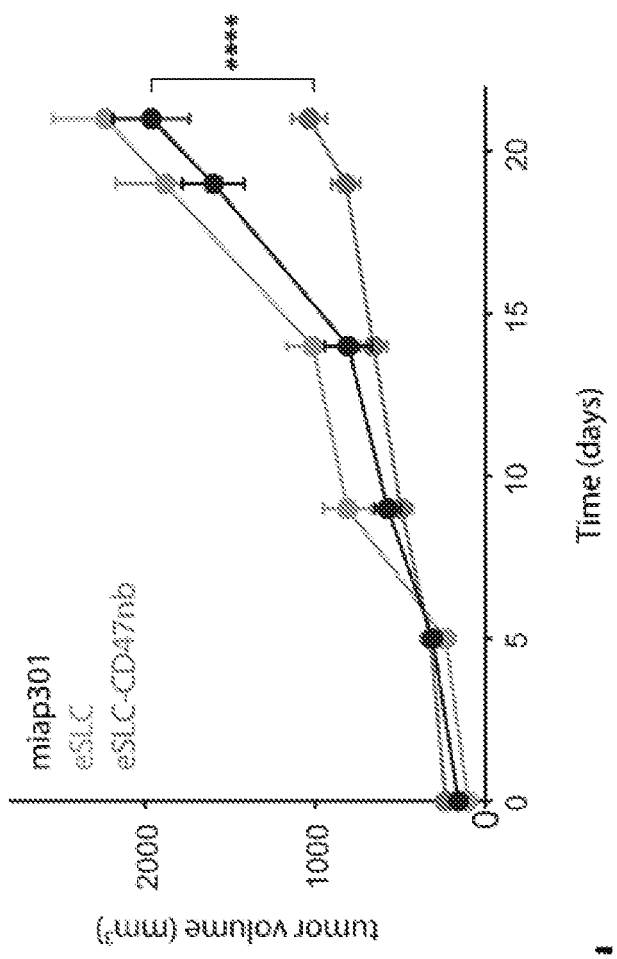
Fig. 9B
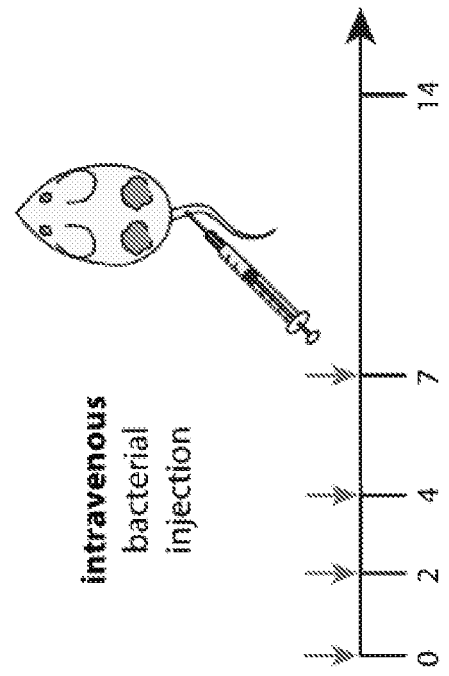
Fig. 9A

Fig. 10
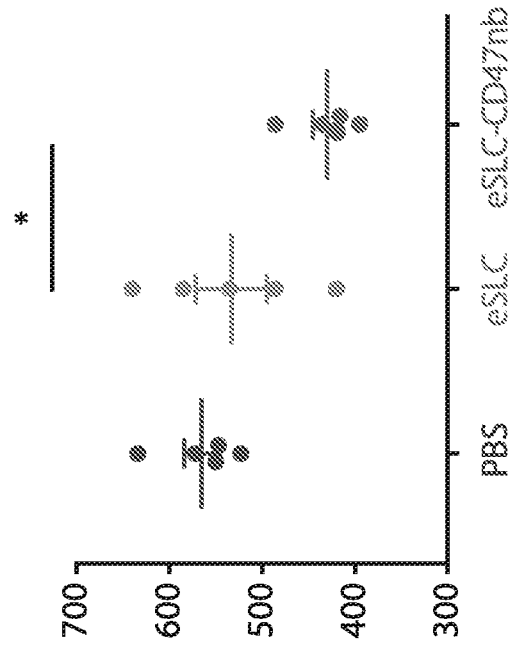
Fig. 10A
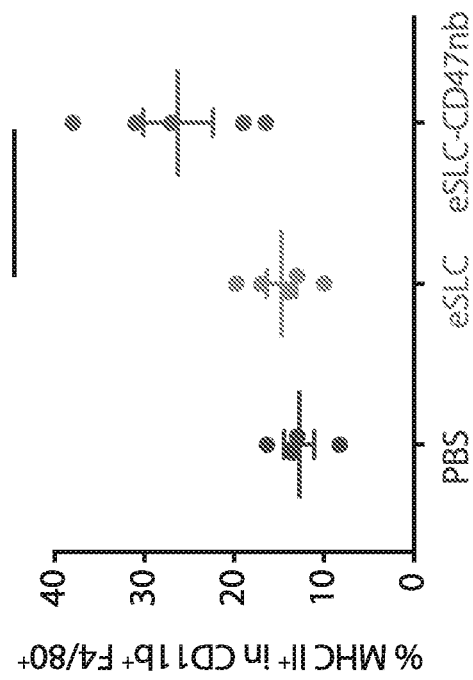
Fig. 10B

Fig. 11
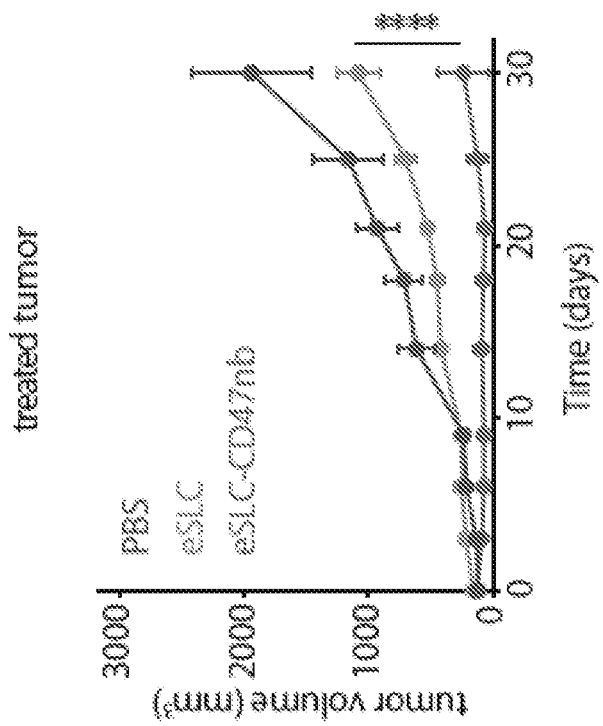
Fig. 11A
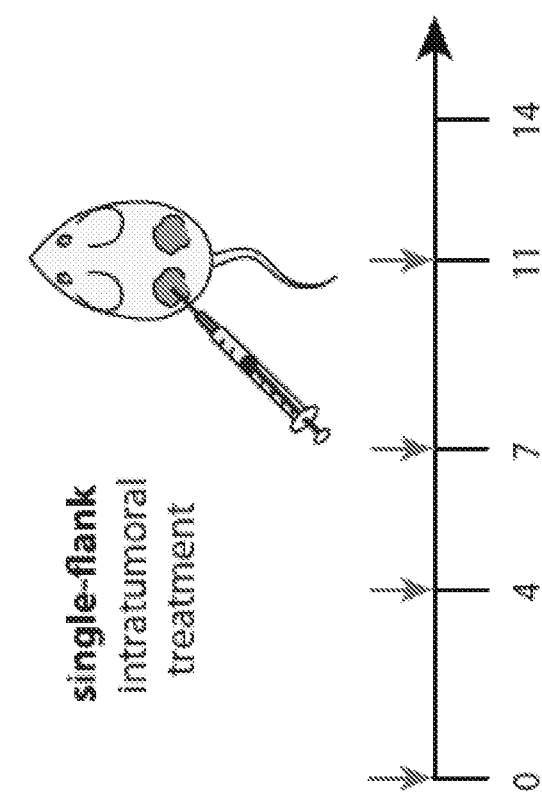
Fig. 11B

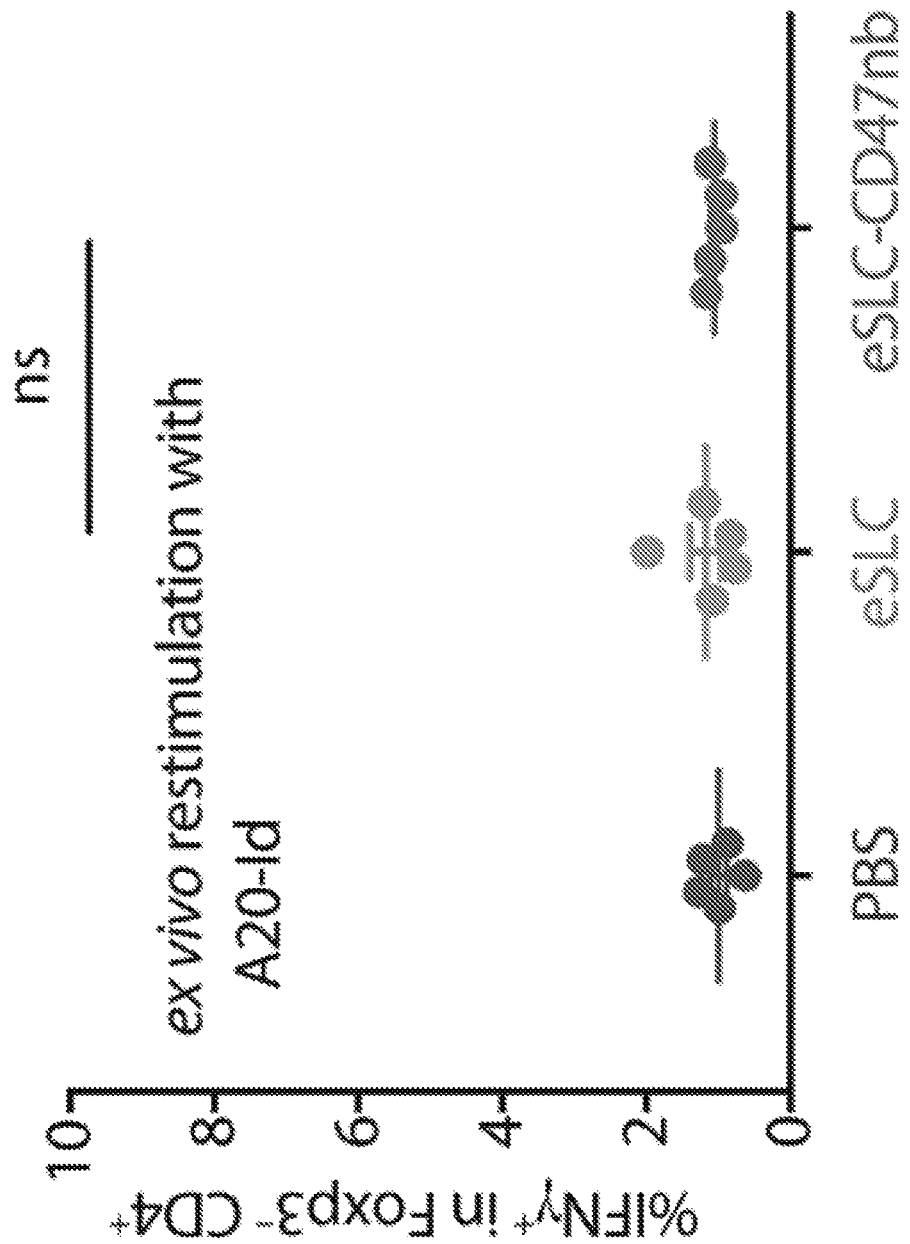

PROGRAMMABLE BACTERIA FOR THE TREATMENT OF CANCER

CROSS-REFERENCE TO OTHER APPLICATIONS

The present application is a continuation of International Patent Application No. PCT/US2019/042795 filed on Jul. 22, 2019, which claims priority to U.S. Patent Application Ser. Nos. 62/700,972 filed Jul. 20, 2018, 62/747,826 filed Oct. 19, 2018, 62/773,748 filed Nov. 30, 2018, and 62/834,032 filed Apr. 15, 2019, each of which are incorporated by reference as if expressly set forth in its entirety herein.

STATEMENT OF GOVERNMENTAL INTEREST

This invention was made with government support under W81XWH-17-1-0395 awarded by the Defense Health Agency, Medical Research and Development Branch, and CA197649, and GM069811 awarded by the National Institutes of Health. The government has certain rights in the invention.

FIELD OF THE INVENTION

Disclosed herein are programmable bacteria for tumor-targeted immunotherapeutic delivery. In certain embodiments, the programmable bacteria comprise at least one synchronized lysis circuit contained in a single operon which are capable of being further engineered to cyclically produce anti-cancer therapeutic agents including but not limited to nanobodies against immunecheckpoint inhibitors and over-expressed markers in cancers, toxins, tumor antigens, cytokines, and chemokines. In some embodiments, the programmable bacteria comprise at least one synchronized lysis circuit contained in a single operon and at least one plasmid producing a therapeutic agent, i.e., at least one plasmid comprising a nucleic acid sequence which encodes a therapeutic agent.

BACKGROUND OF THE INVENTION

The immune system is remarkably effective at defending its host from invading pathogens and maintaining homeostasis. Yet, cancer is able to evade a robust immune system, making it one of the top three leading causes of death globally (Murphy and Weaver 2016). The concept of the immune system acting as the body's first defense against neoplasia motivated decades of research into the role of the immune system in tumorigenesis (Dunn et al. 2002). Since then, studies have also shed light on the complex process of immunoediting, whereby the immune system permits the evolution of the tumor (Dunn et al. 2002; Swann and Smyth 2007). During a period of genetic instability, the tumor cells alter antigens previously recognized by the immune system (Swann and Smyth 2007). While the immune system seeks to destroy cancer cells it recognizes, it creates a selective pressure for new variants able to resist immunological attack.

The tumor microenvironment shapes anti-tumor immunity and can allow for tumor escape through a multitude of mechanisms that promote immunosuppression. Exploiting these mechanisms has led to advancements in the field of cancer immunology. Recently, the field has explored the use of immunology-based therapies such as antibodies against checkpoint inhibitors like programmed cell death protein-1 (PD-1) and its associated ligand PD-L1 as an alternative to the standard surgical or chemotherapeutic options in an attempt to mitigate side effects by focusing only on malignant cells. Cancers often exploit these "checkpoint" pathways by presenting ligands like PD-L1 to bind to PD-1 and inhibit T cell activation, expansion and function, which allows for cancer cell immune evasion (Baumeister et al. 2016). While these antibodies have had efficacy of almost 30% in specific cancers like melanoma, they can also result in immune-related adverse effects (iRAEs) in up to 12% of patients when used as a single agent and more notably in up to 89% in patients when used in combination with other checkpoint blockade therapies (Naidoo et al. 2015). Such iRAEs include pneumonitis, endocrine disorders, and other symptoms related to pancreatic and renal toxicities and may lead to drug discontinuation (Naidoo et al. 2015).

Thus, there is a clear need for improved delivery systems that provide controllable and local delivery of checkpoint blockade inhibitors to the tumor site to minimize adverse effects and to gain access to difficult hypoxic or non-vascularized tumors. Additionally, classic treatments such as chemotherapy are plagued by extreme side effects often due to non-specificity and toxicity. The two major revolutions in treatment paradigms that have emerged in recent years also have shortcomings. These involve targeting actionable alterations in oncogene-driven cancers and immune-oncology. However, these remain limited as druggable genomic alterations are diverse and represent only small subsets of patients in certain tumor types and immune checkpoint inhibitors have only seen long-term survival benefits in a minority of patients.

Described herein are programmable bacteria which provide controlled delivery of anti-cancer and other therapeutic agents including checkpoint inhibitors.

SUMMARY OF THE INVENTION

The disclosure provides for programmable bacteria comprising at least one synchronized lysis circuit contained in a single operon which can be further engineered to produce a therapeutic agent. In some embodiments, the synchronized lysis circuit is integrated into the genome of the programmable bacteria. In some embodiments, the synchronized lysis circuit is contained in a plasmid. In some embodiments, the therapeutic agent is chosen by a skilled practitioner based upon the cancer being treated. In some embodiments, the therapeutic agent is chosen from the group consisting of nanobodies to checkpoint inhibitors and over-expressed markers in cancers, toxins, tumor antigens, cytokines, and chemokines. In some embodiments, the therapeutic agent is an antigen specific for the patient's tumor. In some embodiments, the therapeutic agent is produced by a plasmid, i.e., a plasmid comprising a nucleic acid sequence which encodes the therapeutic agent. In some embodiments the synchronized lysis circuit is on a different plasmid than the plasmid producing the therapeutic agent, i.e., the plasmid comprising a nucleic acid sequence which encodes the therapeutic agent. In some embodiments, the plasmid producing the therapeutic agent is a high copy plasmid.

The disclosure also provides for programmable bacteria comprising at least one synchronized lysis circuit contained in a single operon and at least one plasmid producing a therapeutic agent i.e., a plasmid comprising a nucleic acid sequence which encodes a therapeutic agent. In some embodiments, the therapeutic agent is chosen from the group consisting of nanobodies to checkpoint inhibitors and over-expressed markers in cancers, toxins, tumor antigens, cytokines, and chemokines. In some embodiments, the therapeutic agent is an antigen specific for a patient's tumor. In some embodiments, the synchronized lysis circuit is integrated into the genome of the programmable bacteria. In some embodiments, the synchronized lysis circuit is contained in a plasmid. In some embodiments the synchronized lysis circuit is on a different plasmid than the plasmid producing the therapeutic agent, i.e., the plasmid comprising a nucleic acid sequence which encodes the therapeutic agent. In some embodiments, the plasmid producing the therapeutic agent is a high copy plasmid.

In some embodiments the programmable bacteria comprise more than one plasmid producing a therapeutic agent, e.g., two, three, four, five, six or more plasmids producing therapeutic agents.

The disclosure also provides compositions comprising the programmable bacteria in any of the foregoing embodiments. In some embodiments, the composition is a pharmaceutical composition.

A further embodiment is a solution comprising any programmable bacteria in any of the foregoing embodiments. These solutions can be injected into a subject. These solutions can be frozen. These solutions can be used for the manufacture of a medicament for a disease that can be treated by the programmable bacteria.

Yet a further embodiment is a cell culture comprising any of the programmable bacteria described herein.

All of the foregoing embodiments including programmable bacteria and solutions, compositions and pharmaceutical compositions comprising the programmable bacteria can be used to treat or cure disease. In some embodiments, the disease is cancer.

In some embodiments, the programmable bacteria can be used in a method of inducing systemic adaptive immunity to limit or reduce the growth of untreated tumors.

In some embodiments, the programmable bacteria or compositions or solutions comprising the programmable bacteria can be administered intratumorally, intravenously or orally.

Yet a further embodiment of the disclosure is a method of treating or curing disease in a subject, in need thereof, comprising administering the programmable bacteria described herein or a composition or solution comprising the programmable bacteria described herein. In some embodiments, the composition is a pharmaceutical composition. In some embodiments, more than one programmable bacteria described herein is administered to the subject. In some embodiments, the more than one programmable bacteria are in a single composition or solution. In some embodiments, the more than one programmable bacteria are in different compositions or solutions. In some embodiments, a composition or solution comprises more than one programmable bacteria. In some embodiments, more than one composition or solution comprising the programmable bacteria is administered to the subject. In some embodiments, the programmable bacteria or compositions or solutions comprising the programmable bacteria are administered in conjunction with conventional cancer treatment or therapy.

In yet additional embodiments, the invention relates to kits for practicing any of the methods disclosed herein and includes kits comprising the programmable bacteria and compositions and solutions comprising the programmable bacteria.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 1—Design of a probiotic cancer therapy system for release of a functional anti-PD-L1 blocking nanobody (Nb) by programmable bacteria encoding a synchronized lysis circuit (SLC). FIG. 1A shows the plasmid map of the constitutive expression of PD-L1 Nb on a high copy plasmid. FIG. 1B show graphs of flow cytometry analysis of the PD-L1 expression on CT26 cells (left hand peak: isotype control; right hand peak: stained with an anti-PD-L1 monoclonal antibody (mAb), 10F.9G2 clone).

FIG. 2E shows bacterial population dynamics in batch culture of the four lysing variants. FIG. 2F shows experimental data of the number of bacteria needed to reach quorum as a function of copy number and time to first lysis event. Error bars represent S.E.M of repeated experiments. FIG. 2O are graphs of plate reader experiment showing the oscillations of colonies plated from tumors harvested on day 3 and 14 and a grid showing the number of successful lysis events.

FIG. 3—Probiotics expressing PD-L1 Nb (SLC-int:PD-L1nb) elicit a durable therapeutic response in a syngeneic murine model of colorectal cancer. FIG. 3A is a western blot showing PD-L1 Nb protein levels collected from the supernatant of EcN-lux, EcN-lux-PD-L1 Nb (nonlysing), and SLC-int-PD-L1 Nb strains. FIG. 3D is a graph of the absolute slope between day 0 and 6 and between day 7 and 14 in the treated mice (* $P=0.0175$, segmented linear regression analysis).

FIG. 4—Comparison of the SLC-int:PD-L1 Nb System to a PD-L1 mAb. FIG. 4A shows a graphs of the mean relative tumor trajectory (left panel) and individual trajectories (right panel) of mice receiving intratumoral injections of $5 \times 10^6$ bacteria of EcN-lux (dark lines with squares) or SLC-int: PD-L1nb (light lines with upside down triangles) or intraperiotoneal injection of 200 ug/mouse of 10F.9G2 mAb (medium lines with triangles). All treatments were administered on day 0 and 4 (N=6-8 tumors per group,  $P=0.0015$. two-way ANOVA with Bonferroni post-test, error bars represent S.E.M). FIG. 4B shows histology images (right hand panel) and plot of dirty necrosis scores (left hand panel) of histology tissue samples from tumors treated with PBS, EcN-lux, SLC-int:PD-L1nb, and anti-PD-L1 mAb (N=6-8 scores per group of biological replicates, *$P=0.007$ Mann Whitney Test ordinal non parametric between SLC-int:PD-L1nb and anti-PD-L1 mAb, error bars represent S.E.M). Histology images-main panels are 40×, inserts are 600× of the approximate areas of boxed regions in low magnification images. VT is viable tumor; Circles in insets are bacterial colonies; arrows degenerate neutrophils (i.e., dirty necrosis). (Top left) PBS, (Top right) 10F.9G2 mAb, (Bottom left) EcN-lux, (Bottom right) SLC-int:PD-L1-nb.

FIG. 5—SLC-int:PD-11nb and bacterially-expressed hemolysin exotoxin (hlyE) combination therapy is more efficacious than individual therapies. BALB/c mice were implanted subcutaneously with $5 \times 10^6$ CT26 cells on both hind flanks. When tumors reached approximately 200 mm$^3$, mice received intratumoral injections of $5 \times 10^6$ bacteria every 3-4 days of either EcN-lux, EcN-SLC-hlyE, SLC-int: PD-L1nb, or an equal parts cocktail of EcN-SLC-hlyE and SLC-int:PD-L1nb strains. FIG. 5A is a graph of mean relative tumor trajectory of the mice in each treatment group (n=6-9 tumors per group,** $P=0.0004$, two-way ANOVA with Bonferonni post test, error bars represent S.E.M). FIG. 5B is a scatter plot of absolute tumor volume distribution of each individual mouse in each treatment group. FIG. 5C is a graph of the individual trajectories of relative tumor volumes for each mouse in each treatment group.

FIG. 6G is a graph of TNFα levels measured in the serum of A20-bearing mice receiving a single injection of PD-L1mAb+CTLA-4mAb intraperitoneally or SLC-int:PD-L1nb+SLC-int:CTLA-4nb intratumorally (* P=0.0334, unpaired T test, N=3). FIG. 6O are graphs of IFNg+ (CD4+ FOXP3-) T cells, IFNg+ (CD8+) T cells and IFNg+ TNFα+ (CD8+) T cells in the same mice (*P<0.05, **P<0.01, Ordinary 1-way ANOVA, N=3-6).

FIG. 7B shows a schematic of *E. coli* with SLC reaching a quorum and inducing the phage lysis protein θX174E, leading to bacterial lysis and release of a constitutively produced, anti-CD47 blocking nanobody which binds to CD47 on the tumor cell surface.

FIG. 9—Immunotherapeutic eSLC-CD47nb bacteria primed robust adaptive antitumor immune responses when intravenously administered. FIG. 9A shows the treatment schedule of bacterial immunotherapy. Mice were injected with $5 \times 10^6$ A20 cells into both hind flanks. When tumor volume reached 100-200 mm3 mice received intravenous injections of eSLC or eSLC-CD47nb or intraperitoneal injections of miap301 CD47mAb (400 µg), FIG. 9B is a graph of tumor volume in each group of treated mice (n=3 per group, **** P<0.0001 two-way ANOVA with Tukey's multiple comparisons test).

FIG. 10—Immunophenotyping of tumor infiltrating myeloid and lymphoid subsets following intratumoral bacterial injection. $5 \times 10^6$ A20 cells were subcutaneously implanted into the hind flanks of BALB/c mice. When tumors reached 100-150 mm3 in volume (day 0), mice were treated with either PBS, eSLC or eSLC-CD47nb on days 0, 4 and 7. On day 3 or day 8, tumors were homogenized and tumor-infiltrating myeloid and lymphoid subsets were isolated for flow cytometric analysis (n=3-5 mice per group). FIG. 10A is a graph of the frequency of isolated MHC II+CD11b+F4/80+ macrophages on day 3 following treatment. FIG. 10B is a graph of the MFI of SIRPα staining within CD11b+ F4/80+ subset on day 8 following treatment. (FIGS. 10C-10F—n=3-7 per group. * P<0.05, ** P<0.01, unpaired t-test). (FIGS. 10H-10I, *P<0.05, **P<0.01, unpaired t-test).

FIG. 11—Systemic adaptive immunity following bacterial therapy limited growth of untreated tumors. FIG. 11A shows the treatment schedule. BALB/c mice (n=4 per group) were implanted subcutaneously with $5 \times 10^6$ A20 cells on both hind flanks. When tumor volumes reached 100-150 mm³, mice received intratumoral injections every 3-4 days with PBS, eSLC or eSLC-CD47 into a single tumor. FIG. 11B is a tumor growth curves of treated tumors (** P<0.0001, two-way ANOVA with Tukey's multiple comparisons test, error bars represent s.e.m.). FIG. 11L is a graph of the frequency of tumor-infiltrating IFNγ+ cells within the FOXP3-CD4+ T cell population following ex vivo restimulation with A20-Id peptide (DYWGQGTEL) in the presence of brefeldin A (P>0.05, unpaired two-tailed t-test).

DETAILED DESCRIPTION OF THE INVENTION

Definitions

Figure 1D:
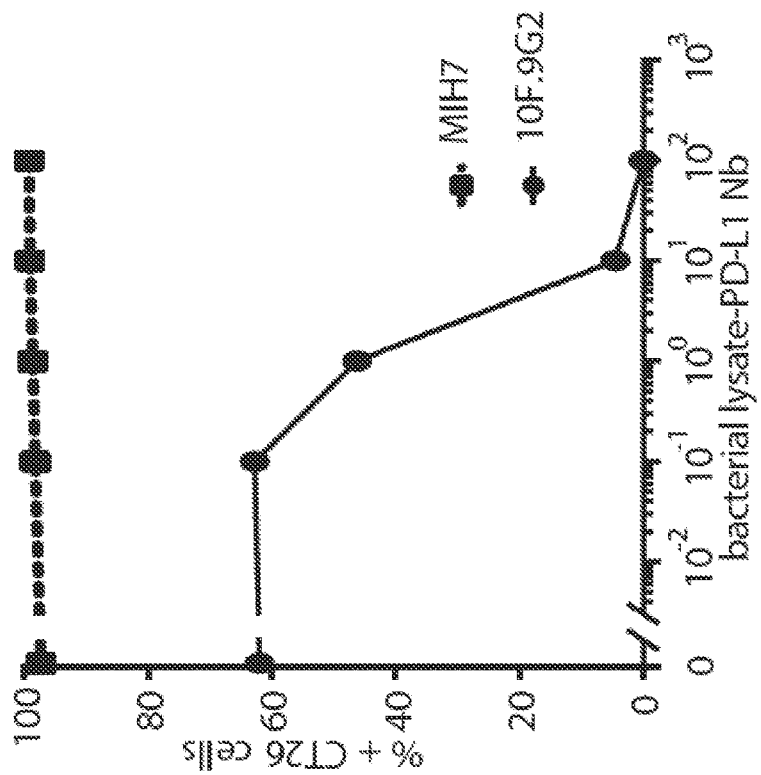
FIG. 1D shows the binding curve of PD-L1 Nb to the 10F.9G2 and MIH7 PD-L1 epitopes of CT26 cells.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The compositions and methods disclosed herein are particularly desirable for human medical applications.

The term "patient" as used in this application means a human subject. In some embodiments, the "patient" is one suffering with cancer.

The terms "treat", "treatment", and the like refer to a means to slow down, relieve, ameliorate or alleviate at least one of the symptoms of the disease, or reverse the disease after its onset, preventing tumor growth, reducing tumor size, preventing or slowly the spread of metastasis, reversing (at least partially) chemo-resistance, and any other subjective or objective improvement in the patient related to the patient's cancer.

The term "cure" and the like means to heal, to make well, or to restore to good health or to allow a time without recurrence of disease so that the risk of recurrence is small.

The terms "prevent", "prevention", and the like refer to acting prior to overt disease or disorder onset, to prevent the disease or disorder from developing or minimize the extent of the disease or disorder or slow its course of development.

The term "in need thereof" would be a subject known or suspected of having or being at risk of developing cancer.

A subject in need of treatment or cure would be one that has already developed the disease or disorder.

As used herein, the term "conventional cancer treatment" or "conventional cancer therapy" refers to treatment or therapy that is widely accepted and used by most healthcare professionals. It is different from alternative or complementary therapies, which are not as widely used. Examples of conventional treatment for cancer include surgery, chemotherapy, targeted therapies, radiation therapy, tomotherapy, immunotherapy, cancer vaccines, hormone therapy, hyperthermia, stem cell transplant (peripheral blood, bone marrow, and cord blood transplants), photodynamic therapy, and blood product donation and transfusion.

The term "agent" as used herein means a substance that produces or is capable of producing an effect and would include, but is not limited to, chemicals, pharmaceuticals, biologics, small organic molecules, antibodies, nucleic acids, peptides, and proteins.

As used herein, "programmable bacteria" means the all forms of the bacteria disclosed herein which are programmed, recombinantly or genetically engineered to be capable of delivering a therapeutic agent. The term is used to include all embodiments and forms of the programmable bacteria which can include bacteria from any strain which are non-pathogenic. In some embodiments, the bacteria are probiotic. The term also includes programmable bacteria comprising at least one synchronized lysis circuit contained in a single operon integrated in the genome of the bacteria. The term further includes programmable bacteria comprising at least one synchronized lysis circuit contained in a single operon contained on a plasmid within the programmable bacteria. The term includes programmable bacteria comprising a synchronized lysis circuit contained in a single operon that can be further programmed to include one or more plasmids comprising a nucleic acid sequence which encodes a therapeutic agent but does not include the one or more plasmids currently. The term further includes programmable bacteria comprising a synchronized lysis circuit contained in a single operon which also comprises one or more plasmids comprising a nucleic acid sequence which encodes a therapeutic agent. In some embodiments, the synchronized lysis circuit contained in a single operon can be integrated in the genome of the bacteria. In some embodiments, the synchronized lysis circuit contained in a single operon can be contained on a plasmid within the programmable bacteria. In an embodiment where the synchronized lysis circuit contained in a single operon is contained on a plasmid, it is contained on a different plasmid than the one or more comprising a nucleic acid sequence which encodes a therapeutic agent.

As used herein "non-pathogenic bacteria" refer to bacteria that are not capable of causing disease or harmful responses in a host. In some embodiments, non-pathogenic bacteria are gram-negative bacteria. In some embodiments, non-pathogenic bacteria are gram-positive bacteria. In some embodiments, non-pathogenic bacteria do not contain lipopolysaccharides (LPS). In some embodiments, non-pathogenic bacteria are commensal bacteria. Examples of non-pathogenic bacteria include, but are not limited to certain strains belonging to the genus *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli* Nissle, *Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. Naturally pathogenic bacteria may be genetically engineered to provide reduce or eliminate pathogenicity.

The term "probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. In some embodiments, the probiotic bacteria are gram-negative bacteria. In some embodiments, the probiotic bacteria are gram-positive bacteria. Some species, strains, and/or subtypes of non-pathogenic bacteria are currently recognized as probiotic bacteria. Examples of probiotic bacteria include but are not limited to certain strains belonging to the genus *Bifidobacteria, Escherichia coli, Lactobacillus*, and *Saccharomyces*, e.g., *Bifidobacterium bifidum, Enterococcus faecium, Escherichia coli* strain Nissle, *Lactobacillus acidophilus, Lactobacillus bulgaricus, Lactobacillus paracasei, Lactobacillus plantarum*, and *Saccharomyces boulardii*. The probiotic may be a variant or a mutant strain of bacterium. Non-pathogenic bacteria may be genetically engineered to enhance or improve desired biological properties, e.g., survivability. Non-pathogenic bacteria may be genetically engineered to provide probiotic properties. Probiotic bacteria may be genetically engineered or programmed to enhance or improve probiotic properties.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "plasmid" means the vehicle by which a DNA or RNA sequence (e.g. a foreign gene) can be introduced into a host cell, so as to transform the host and promote expression (e.g. transcription and translation) of the introduced sequence. Plasmids typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A plasmid is generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Programmable plasmids will often include one or more replication systems for cloning or expression, one or more markers for selection in the host, e.g. antibiotic resistance, and one or more expression cassettes.

As used herein a "pharmaceutical composition" refers to a preparation of programmable bacteria of any of the foregoing embodiments with other components such as a pharmaceutically acceptable suitable carrier and/or excipient.

The term "pharmaceutically-acceptable" refers to molecular entities and compositions that do not produce an allergic or similar untoward reaction when administered to a host, such as gastric upset, dizziness and the like, when administered to a human, and approved by a regulatory agency of the Federal or a state government or listed in the U.S. Pharmacopeia or other generally recognized pharmacopeia for use in animals, and more particularly in humans.

As used herein, the term "carrier" refers to a diluent, adjuvant, excipient, or vehicle with which the therapeutic is administered, and includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., a cancer. A therapeutically effective amount may, for example, be sufficient to treat, prevent, reduce the severity, delay the onset, and/or reduce the risk of occurrence of one or more symptoms of a disorder associated with cancerous cells. An effective amount for a particular subject may vary depending on factors such as the condition being treated, the overall health of the patient, the method route and dose of administration and the severity of side effects. A therapeutically effective amount, as well as a therapeutically effective frequency of administration, can be determined by methods known in the art and discussed below The articles "a" and "an," as used herein, should be understood to mean "at least one," unless clearly indicated to the contrary.

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Programmable DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

| Abbreviations | |
|---|---|
| SLC | synchronized lysis circuit |
| Nb | nanobody |
| EcN or EcN-lux | *E.coli Nissle* 1917 |
| EcN-SLC or EcN-lux:SLC-int or SLC-int | *E.coli Nissle* 1917 engineered with synchronized lysis circuit |
| eSLC-CD47nb | bacteria containing a synchronized lysis circuit and a CD47 nanobody |
| SLC-int:PD-L1 Nb | bacteria containing an integrated synchronized lysis circuit and an anti-PD-L1 nanobody |
| SLC-int:CTLA-4 Nb | bacteria containing an integrated synchronized lysis circuit and an anti-CTLA-4 nanobody |
| EcN-SLC-int-cd47nb | bacteria containing a synchronized lysis circuit and a CD47 nanobody |
| Φx174E | phage lysis gene |
| AHL | acylhomoserine lactone |
| TLR | toll-like receptor |

Disclosed herein are methods and compositions for the delivery of therapeutic agents including but not limited to nanobodies to checkpoint inhibitors and over-expressed markers in cancers, toxins, tumor antigens, cytokines and chemokines. These methods and compositions are based upon the use of a stable biological circuit integrated into and/or contained within non-pathogenic bacteria. These methods and compositions allow for the therapeutic agent release locally, thus minimizing toxicity of the therapeutic agent. However, systemic delivery of the compositions to a subject, e.g., oral or intravenous administration, is also contemplated. There are also numerous other advantages to the compositions not found using the therapeutic agents alone.

As shown herein nanobodies were released using a sychronized lysing circuit contained in a single operon, thereby reducing possible horizontal gene transfer. This also served as a biocontainment measure to confine the bacterial population to the tumor site thusly minimizing the risk of systemic iRAEs. In some embodiments, the sychronized lysing circuit contained in a single operon was integrated into the genome of the bacteria. In some embodiments, these nanobodies include but are not limited to PD-L1, CTLA-4, and CD47 antagonists. See, e.g., Examples 4-6 and 8-10 and 12.

The integrated lysis circuit/nanobody systems disclosed herein demonstrated comparable therapeutic efficacy to the clinically relevant monoclonal antibodies and in some instances greater therapeutic efficacy. Furthermore, combining the combining the integrated lysis circuit/nanobody systems with a bacterially-expressed hemolysin exotoxin led to greater therapeutic efficacy than either monotherapy (e.g., Example 3-6). Moreover, when a combinatorial nanobody mixture or cocktail was used, synergistic therapeutic effects were observed along with a shift in the cytokine profile of the tumor microenvironment. Specifically, the bacteria comprising the single lysis circuit/nanobody CTLA-4 led to more detectable proinflammatory cytokine levels at the tumor site, which could act cooperatively with the bacteria comprising single lysis circuit/nanobody PD-L1 by supporting increased infiltration of immune cells into the tumor microenvironment. Additionally, 100% of tumors treated with the cocktail of both programmable bacteria responded (See, e.g., Example 6).

Cancer immunotherapies are often more effective in combination with other anticancer agents. Therefore, lysis circuit systems can be programmed to produce a wide variety of therapeutic agents that can be used in combination. Microbial-based therapeutic platforms are highly modular and optimal for the rapid production of multiple drugs that can then be delivered as a cocktail.

Additionally, the some of the exemplified integrated lysis circuits were developed in the probiotic strain, E. coli Nissle 1917, which has been shown to colonize liver metastases when delivered orally (Danino et al. 2015), thus offering a more translational route of therapeutic delivery for more advanced metastatic disease.

Shown herein also was the use of both the E. coli Nissle 1917 and a non-pathogenic E. coli to specifically lyse within the tumor microenvironment and release an encoded nanobody antagonist of CD47 (CD47nb) (Sockolosky et al. 2016), an anti-phagocytic receptor commonly overexpressed in several human cancers (Majeti et al. 2009; Willingham et al. 2012). Recent studies have shown that CD47 blockade not only increases phagocytosis of cancer cells but also promotes cross presentation of tumor antigens by dendritic cells to enhance priming of antitumor effector T cells in syngeneic murine tumor models (Sockolosky et el. 2016; Liu et al. 2015; Kauder et al. 2018). However, as demonstrated in both preclinical models and human trials, CD47 blockade using systemically delivered antibodies can result in anemia and thrombocytopenia due to high expression of CD47 on red blood cells and platelets respectively (Ingram et al. 2017; Huang et al. 2017; Advani et al. 2018). To improve upon its therapeutic profile, a nanobody (camelid single heavy chain antibody fragment) against CD47 with approximately 200-fold higher binding affinity than the commercially available anti-mouse CD47 monoclonal antibody (miap301) was recently developed and characterized (Sockolosky et al. 2016). This nanobody demonstrated mild effects as a systemically administered monotherapy, potentially due to lack of Fc-mediated effector function (Ingram et al. 2017).

In this study, a synchronized lysis circuit/nanobody system was used in an E. coli strain that colonizes in tumors and undergoes intratumoral quorum-lysis to locally release an encoded nanobody antagonist of CD47 (see, e.g., Examples 8-10). This system allows for the combined local delivery of an immunotherapeutic along with immunostimulatory bacterial lysis adjuvants to stimulate antitumor immunity and promote tumor regression. Consequently, the enhanced infiltration and activation of tumor infiltrating lymphocytes leading to the induction of durable and systemic anti-tumor immunity was achieved by the synchronized lysis circuit/nanobody system.

The delivery of CD47nb by tumor-colonizing bacteria increased activation of tumor-infiltrating T cells, stimulated rapid tumor regression, prevented metastasis, and lead to long-term survival in a syngeneic tumor model (see, e.g., Example 10). Moreover, a surprising advantage of the local injection of integrated lysis circuit/nanobody system was the systemic antitumor immune responses that reduced the growth of untreated tumors—providing, the first demonstration of an abscopal effect induced by an engineered bacterial immunotherapy (see, e.g., Example 11).

The use of the programmable bacteria with the integrated SLC was also used to deliver the CD47nb and high affinity SIRPα variants (See, e.g, Example 12).

Thus, engineered bacteria can be used for safe and local delivery of immunotherapeutic payloads leading to systemic antitumor immunity.

The results set forth herein show the multiple advantages of the single operon synchronized lysis circuit and the lysis-mediated release of the therapeutic agent over conventional therapy. Firstly, intratumoral delivery of nanobody by synchronized lysis circuit increases the local concentration of immunotherapy while simultaneously preventing systemic toxicity.

Second, local treatment with the synchronized lysis circuit promotes the induction of systemic antitumor immune responses that are not observed following treatment with other therapeutic agents including monoclonal antibody. These include pro-inflammatory cytokine production via TLRs, due to endotoxin/LPS release in gram-negative bacteria, and activation of the innate immune system via intracellular receptors and pathways including STING leading to type I IFN production, dendritic cell priming, and T cell activation.

This further allows the use of checkpoint inhibitors for so-called cold cancers. Tumors such as colorectal are considered "cold" due to overproduction of prostaglandins that dampen the immune response (Sandage et al. 2017). For this reason, colorectal cancer has demonstrated only modest responses to checkpoint blockade. Therefore, administration of checkpoint blockade nanobodies in vehicles lead to more immune cell recruitment enhances therapeutic responses which would be otherwise difficult to attain for "cold" cancers.

Third, the ease of engineering bacteria to express additional immunotherapeutic nanobodies, cytokines and other therapeutic agents, opens the possibility of evaluating combinations of several other immunotherapeutics which have exhibited systemic toxicity but may be safe and effective when delivered intratumorally using the synchronized lysis circuit. The systems described herein allow for the delivery of immunotherapeutics and other agents in a spatiotemporally defined manner and permit their delivery within diverse solid tumor settings. More broadly, programmable bacteria offer several advantages over other immunotherapeutic modalities including checkpoint blockade, CAR-T therapy and oncolytic virotherapy.

Fourth, even a single administration of the programmable bacteria resulted in a decrease in tumor volume and growth days after administration.

Fifth, there is a synergistic effect when nanobodies to checkpoint inhibitors were combined. When the programmable bacteria are delivering nanobodies as monotherapies (SLC-int: PD-L1nb or SLC-int:CTLA-4nb) there is a therapeutic efficacy similar to that of their analogous mAb therapies, albeit with less side effects. However, when these monotherapies are combined (SLC-int:Nb cocktail), where the total number of bacteria delivered does not differ from the monotherapies, complete tumor regression is seen. The tumor clearance is due to the synergistic combination of the SLC-int: CTLA-4nb and SLC-int:PD-L1nb since the total number of bacteria injected across all treatment groups was the same.

Finally, the integrated lysis circuit can be used to treat metastatic cancers due to the observed abscopal effect as well as by using bacteria known to target tissues and organs where metastasis often occurs, e.g., liver and lung.

The programmable bacteria disclosed herein can be delivered intratumorally as well as intravenously and orally and has been shown to work on several primary cancers as well as metastasized cancers even after a single administration. In all instances, there was no adverse effects following the administration of the programmable bacteria.

Abscopal Effect

The term "abscopal effect" was coined in 1953 to describe the shrinkage of untreated tumors concurrently with the shrinkage of tumors that had been locally treated at the time by radiation. While initially associated with localized radiation, the term has also come to encompass other type of localized tumor treatment. True abscopal effect is only when localized treatment results in systemic effects. For example, chemotherapy which circulates through the blood would not exhibit an abscopal effect.

An abscopal effect is very rare and has never been seen in cancer treatments other than radiation and possibly with the combination of radiation and immune checkpoint inhibitors. Reported herein is evidence of a cancer therapy wherein an abscopal effect is seen without the use of radiation.

Specifically, the use of the programmable bacteria to locally deliver a nanobody to a check-point inhibitor to a tumor led to the regression of untreated tumors. Moreover, this was a true abscopal effect as no programmable bacteria were found in the untreated tumors. (see, e.g., Example 11).

While not being bound by any theories, the programmable bacteria stimulated the immune system to seek out tumors and metastases that are even too small to be detected. The combined effect of bacterially induced local inflammation within the tumor and the blockade of checkpoint inhibitors lead to increased phagocytosis of tumor cells and subsequently to enhanced activation and proliferation of T cells within the treated tumors. Treatment with their engineered bacteria not only cleared the treated tumors but also reduced the incidence of tumor metastasis in multiple models.

Further evidence of this immune system stimulation is shown in this study where the untreated tumors had enhanced tumor antigen specific CD8+ cell activity (see e.g., Example 11).

Even further evidence is shown in the other studies reported herein. Mice treated with programmable bacteria comprising a nanobodies to different checkpoint inhibitors had an increase in splenic central memory CD4− and CD8+ cells and tumor-infiltrating IFNg+CD4+, IFNg+CD8+ cells, and double positive IFNg+TNFα+CD8+ cells, suggesting both systemic and local enhanced activation of T cells (see, e.g, Example 6) and induction of systemic adaptive immunity, leading to an abscopal effect and the shrinking of untreated tumors.

Components of the Programmable Bacteria

The programmable bacteria described herein comprise at least non-pathogenic bacteria and at least one synchronized lysis circuit contained in a single operon. In some embodiments, the programmable bacteria also comprise one or more plasmids that produce a therapeutic agent, i.e., one or more plasmids comprising a nucleic acid sequence which encodes a therapeutic agent. In some embodiments, the programmable bacteria also comprise additional components.

Bacteria

The programmable bacteria of the current disclosure comprise at least one synchronized lysis circuit contained in a single operon. In some embodiments, the programmable bacteria comprise one or more plasmid that produce a therapeutic agent, i.e., one or more plasmids comprising a nucleic acid sequence which encodes the therapeutic agent. The programmable bacteria of the current disclosure are capable of local and tumor-specific delivery of therapeutic agents, in particular anti-cancer agents, thereby reducing the systemic cytotoxicity and/or immune dysfunction associated with systemic administration of said agents. The programmable bacteria may be administered systemically as well, e.g, orally or parenterally.

The programmable bacteria described herein are advantageous in that they can generate an antitumor immune response, e.g., a local or innate immune response that develops into a systemic or adaptive immune response. For example, the programmable bacteria can stimulate the antigen-presenting ability of immune cells that infiltrate the tumor, the antigen-presenting ability of immune cells that infiltrate the tumor microenvironment (e.g., B cells, plasmacytoid and myeloid dendritic cells (DCs), CD4+ cells, CD8+ cells, T regs, natural killer cells (NK cells), and tumor-associated macrophages (TAMs)). Many immune cells found in the tumor microenvironment express pattern recognition receptors (PRRs), which receptors play a key role in the innate immune response through the activation of pro-inflammatory signaling pathways, stimulation of phagocytic responses (macrophages, neutrophils and dendritic cells) or binding to micro-organisms as secreted proteins. Examples of PRRs include Toll-like receptors (TLR), which are type 1 transmembrane receptors that have an extracellular domain which detects infecting pathogens. TLR1, 2, 4, and 6 recognize bacterial lipids, TLR9 recognizes bacterial DNA, and TLR5 and 10 recognize bacterial or parasite proteins. Other examples of PRRs include C-type lectin receptors (CLR), e.g., group I mannose receptors and group II asialoglycoprotein receptors, cytoplasmic (intracellular) PRRs, nucleotide oligomerization (NOD)-like receptors (NLRs), e.g., NOD1 and NOD2, retinoic acid-inducible gene I (RIG-I)-like receptors (RLR), e.g., RIG-I, MDA5, and DDX3, and secreted PRRs, e.g., collectins, pentraxins, ficolins, lipid transferases, peptidoglycan recognition proteins (PGRs) and the leucine-rich repeat receptor (LRR).

Upon detection of a pathogen, PRRs initiate the activation of signaling pathways, that stimulates the production of co-stimulatory molecules and pro-inflammatory cytokines, e.g., type I IFNs, IL-6, TNF, and IL-12, which play a role in the activation of inflammatory and immune responses mounted against infectious pathogens. Such response triggers the activation of immune cells present in the tumor microenvironment that are involved in the adaptive immune response (e.g., antigen-presenting cells (APCs) such as B cells, DCs, TAMs, and other myeloid derived suppressor cells).

Furthermore, TLRs can also be expressed by tumor cells. The direct activation of TLRs on cancer cells can result in the death of the targeted tumor cell and/or up-regulate antigen presenting molecules, e.g., in the case of B-cell lymphomas, for example. See, e.g., Example 8.

This ability of the programmable bacteria to induce an immune response which works in synergy with the therapeutic agent being delivered is one advantage. This induction allows the therapeutic agent to work more effectively in the tumor where delivered but is also responsible for the abscopal effect.

In some embodiments, the programmable bacteria are obligate anaerobic bacteria. In some embodiments, the programmable bacteria are facultative anaerobic bacteria. In some embodiments, the programmable bacteria are aerobic bacteria. In some embodiments, the programmable bacteria are gram-positive bacteria. In some embodiments, the programmable bacteria are gram-negative bacteria. In some embodiments, the programmable bacteria are non-pathogenic bacteria. In some embodiments, the programmable bacteria are commensal bacteria. In some embodiments, the programmable bacteria are probiotic bacteria. In some embodiments, the programmable bacteria are naturally pathogenic bacteria that are modified or mutated to reduce or eliminate pathogenicity. Exemplary bacteria include, but are not limited to, *Bacillus, Bacteroides, Bifidobacterium, Brevibacteria, Caulobacter, Clostridium, Enterococcus, Escherichia coli, Lactobacillus, Lactococcus, Listeria, Mycobacterium, Saccharomyces, Salmonella, Staphylococcus, Streptococcus, Vibrio, Bacillus coagulans, Bacillus subtilis, Bacteroides fragilis, Bacteroides subtilis, Bacteroides thetaiotaomicron, Bifidobacterium adolescentis, Bifidobacterium bifidum, Bifidobacterium breve* UCC2003, *Bifidobacterium infantis, Bifidobacterium lactis, Bifidobacterium longum, Clostridium acetobutylicum, Clostridium butyricum, Clostridium butyricum* M-55, *Clostridium butyricum miyairi, Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium,* and *Vibrio cholera.*

In certain embodiments, the bacteria are gram-negative comprising an endotoxin/LPS which can potently activate pro-inflammatory cytokine production via TLRs. In some embodiments, the bacteria are a non-pathogenic *E. coli*. In some embodiments, the bacteria are the probiotic bacteria, *E. coli* Nissle 1917 bacteria.

In some embodiments, the programmable bacteria without further manipulation or engineering are capable of activating the innate immune system via intracellular receptors and pathways including STING leading to type I IFN production, dendritic cell priming and T cell activation.

In some embodiments, a gene of interest is expressed in the bacteria which enhances the efficacy of therapeutic agent. Examples of these include T cell responses specific for *Bacteroides thetaiotaomicron* or *Bacteroides fragilis* that were associated with the efficacy of CTLA-4 blockade in mice and in patients and the efficacy of an antagonist of PD-1 in a mouse model of melanoma using *Bifidobacterium.*

In some embodiments, the programmable bacteria are capable of targeting cancerous cells, particularly in the hypoxic regions of a tumor.

In some embodiments, the bacteria are naturally capable of directing itself to cancerous cells, necrotic tissues, and/or hypoxic tissues. For example, bacterial colonization of tumors may be achieved without any specific genetic modifications in the bacteria or in the host. In some embodiments, the programmable bacteria are not naturally capable of directing itself to cancerous cells, necrotic tissues, and/or hypoxic tissues, but is genetically engineered to do so.

In some embodiments, the programmable bacteria have gene deletions for virulence genes such as PhoP, PhoQ, aroA, and msbB, allowing the bacteria to internalize inside tumors upon injection or feeding, and grow within the necrotic tissue.

Synchronized Lysis Circuit

A further component of the programmable bacteria is the synchronized lysis circuit (SLC). The SLC allow the bacteria to lyse when a certain cell density is reached, thus releasing a therapeutic agent or agents as well as other naturally occurring bacterial endotoxins.

The programmable bacteria disclosed herein comprise at least one synchronized lysis circuit contained in a single operon. In some embodiments the SLC is genomically integrated into the genome of the bacteria. In some embodiments, the SLC is on a plasmid or plasmids contained within the bacteria. Any plasmid known in the art can be used and include but are not limited to pColE1, p15A, pSC101, pUC19, pBR322, pET, pGEX, pR6K, pACYC, pBluescript, and pGEM.

The SLC comprises at least the following components: a nucleic acid encoding a quorum-sensing gene; a nucleic acid encoding a lysis gene; a promoter; and a terminator. In some embodiments, the SLC comprises more than one of each component. Additional components of the SLC may include antibiotic resistance genes.

Quorum sensing is a bacterial cell-cell communication process that involves the production, detection, and response to extracellular signaling molecules called autoinducers (AIs). AIs accumulate in the environment as the bacterial population density increases, and bacteria monitor this information to track changes in their cell numbers and collectively alter gene expression.

The SLCs exemplified herein comprised the quorum sensing genes LuxR and luxI, which are the quorum sensing genes typically used by gram negative bacteria. In these systems, the LuxI homolog is an AI synthase that catalyzes a reaction between SAM and an acyl carrier protein (ACP) to produce a freely diffusible acyl homoserine lactone (AHL) AI. At high concentrations, AHL bind to cognate cytoplasmic LuxR-like transcription factors. Typically, AHL-bound LuxR-type proteins also activate luxI expression, forming a feed-forward autoinduction loop that floods the vicinity with AI. Thus one embodiment of the SLC comprises a nucleic acid encoding a LuxR gene or homologs thereof, and a nucleic acid encoding a luxI gene or homologs thereof.

Other quorum sensing gene systems that are known in bacteria can be used. These include but are not limited to Las, Rhl, TraI/TraR, ExpI/ExpR-CarI/CarR, and Rpa.

The SLC further comprises a nucleic acid encoding a lysis gene. The SLC exemplified herein utilizes the lysis gene E from the bacteriophage ΦXΓ74. Other lysis genes that can be used in the SLC include but are not limited to the lambda phage lysis genes and the E7 lysis gene from colicin producing bacteria.

The SLC also includes at least one inducible promoter. Exemplified herein is the use of the plux promoter which is induced by AHL. Other inducible promoters can be used in the SLC. The choice of promoter is based upon the quorum sensing genes used in the SLC and it is within the skill of the art to choose the appropriate promoter.

One embodiment of the present invention is the SLC is contained in a single module system or in a single operon. This optimized smaller system can be genomically integrated into the bacteria or as a separate plasmid contained in the bacteria. Either way, the reduced burden on the bacteria allows for better bacterial growth and more efficient control and delivery of the therapeutic agent.

In one embodiment, the SLC may utilize the Lux quorum sensing system comprising the luxl and LuxR genes and a single luxl promoter. This single promoter allows transcription of both the luxl and the lysis gene, which is the lysis gene E from the bacteriophage ΦXΓ74. The bacteria comprising the SLC express luxl, produce the luxl protein which enzymatically produces AHL, which subsequently binds to the LuxR protein which activates transcription from the luxl promoter when the AHL concentration reaches a threshold level. Thus, the bacterial population will grow to a threshold population size, at which point sufficient AHL has accumulated to activate transcription from the Luxl promoter and produce the lysis protein. A fraction of the population will lyse, leaving behind a small colony size and thus reduced AHL concentrations. These surviving bacteria then re-grow to the threshold population size and exhibit another lysis event. This process continues in a periodic fashion. Upon lysis, the cells will release intracellular contents, including plasmids and therapeutic agents, to the extracellular space. See FIG. 1A.

A further advantage of the SLC described herein is that it is contained separately from the plasmid producing the therapeutic agent. This allows for the manufacture of programmable of bacteria with the SLC, in which one of more plasmids producing a therapeutic agent can be easily added at a later time. This in turn allows the programmable bacteria to be "custom-produced" with one or more plasmids producing a therapeutic agent targeted for a particular tumor and/or patient.

In some embodiments, the SLC is contained in a single plasmid within the bacteria and the bacteria also comprise one or more plasmids producing the therapeutic agent. In some embodiments, the SLC is genomically integrated into the genome of the bacteria and the bacteria further comprises one or more plasmids producing the therapeutic agent.

Figures 2, 2A:
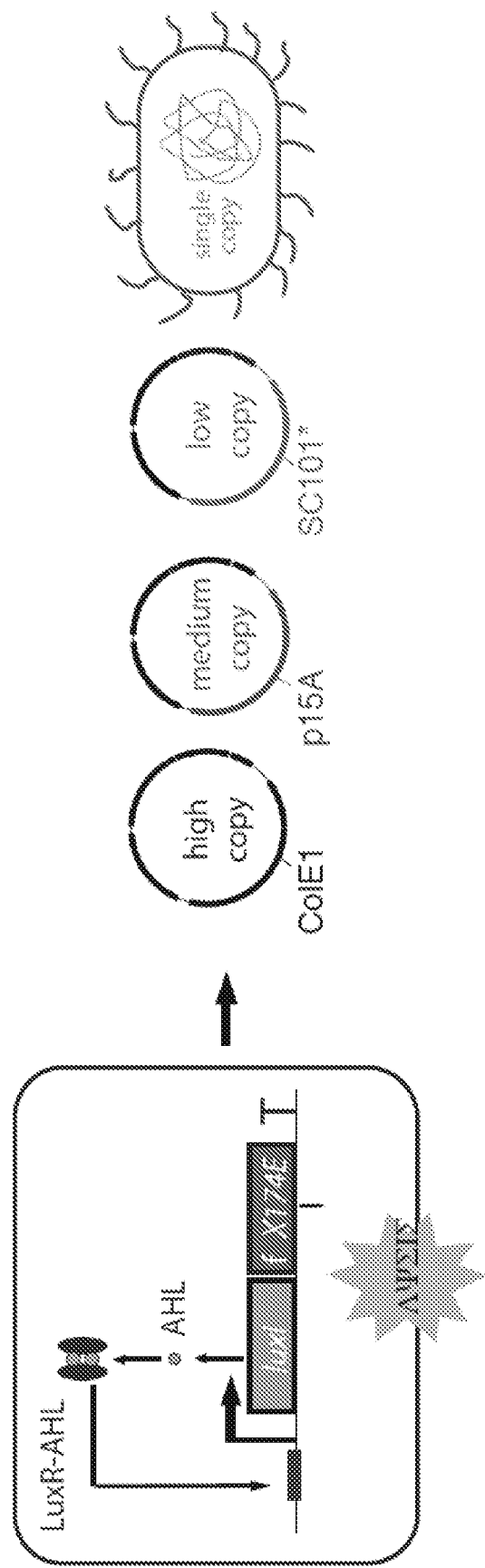
FIG. 2—Characterization of lysing variant dynamics.
FIG. 2A is a circuit diagram of the single operon SLC circuit in which plux drives the transcription of luxR, luxI and φ174E genes under a single promoter. The circuit was cloned into three plasmids of different copy numbers: sc101* (3-4 copies, low), p15A (15-20 copies, medium), and ColE1 (70-100 copies, high) and integrated once into the φ80 site of the EcN-lux genome (EcN-Lux:SLC-int).

In one embodiment, the SLC was constructed in a plasmid and then genomically integrated into a φ80 site of the EcN-lux strain (see FIG. 2A). It is within the skill of the art to determine a proper site for integration of the SLC depending on the plasmid used for the construct and the bacteria of choice.

Therapeutic Agents

The programmable bacteria described herein are capable of delivering one or more therapeutic agents. In some embodiments, the therapeutic agent is produced by a plasmid which is introduced into the programmable bacteria. In some embodiments, the plasmid comprises a nucleic acid encoding a therapeutic agent. In some embodiments, the nucleic acid is operably linked to a promoter. In some embodiments, the promoter is constitutive. In some embodiments, the promoter is inducible.

Examples of plasmid include but are not limited to pColE1, p15A, pAH162, and pSC101.

Examples of constitutive promoters include but are not limited to a chicken beta actin promoter, a retroviral Rous sarcoma virus (RSV) LTR promoter (optionally with a RSV enhancer), a cytomegalovirus (CMV) promoter (optionally with a CMV enhancer), a SV40 promoter, a dihydrofolate reductase promoter, a 13-actin promoter, a phosphoglycerol kinase (PGK) promoter, and an EFla promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Examples of inducible promoters regulated by exogenously supplied promoters include a zinc-inducible sheep metallothionine (MT) promoter, a dexamethasone (Dex)-inducible mouse mammary tumor virus (MMTV) promoter, a T7 polymerase promoter system (WO 98/10088), a ecdysone insect promoter (No et al., $Proc.\ Natl.\ Acad.\ Sci.\ USA$ 93:3346-3351 (1996)), a tetracycline-repressible system (Gossen et al., $Proc.\ Natl.\ Acad.\ Sci.\ USA$ 89:5547-5551 (1992)), a tetracycline-inducible system (Gossen et al., $Science$ 268:1766-1769 (1995), a RU486-inducible system (Wang et al., $Nat.\ Biotech.$ 15:239-243 (1997) and Wang et al., $Gene\ Ther.$ 4:432-441 (1997)) and a rapamycin-inducible system (Magari et al., $J.\ Clin.\ Invest.$ 100:2865-2872 (1997)).

Still other types of inducible promoters which may be useful in this context are those which are regulated by a specific physiological state, e.g., temperature, acute phase, a particular differentiation state of the cell, or in replicating cells only. In some embodiments, the therapeutic agent is operably linked to a directly or indirectly inducible promoter that is induced under low-oxygen or anaerobic conditions. In some embodiments, the therapeutic agent is operably linked to a directly or indirectly inducible promoter that is induced under inflammatory conditions (e.g., RNS, ROS). In some embodiments, the therapeutic agent is operably linked to a directly or indirectly inducible promoter that is induced under immunosuppressive conditions, e.g., as found in the tumor.

In some embodiments, the inducible promoter is an oxygen level-dependent promoter and the therapeutic agent is expressed in low-oxygen, microaerobic, or anaerobic conditions. For example, in low oxygen conditions, the oxygen level-dependent promoter is activated by a corresponding oxygen level-sensing transcription factor, thereby driving production of anti-cancer molecule. Inducible promoters described herein for hypoxic conditions such as FMR, AMR and DMR can be used as well as those for elevated levels of reactive oxygen species (ROS).

In some embodiments, the plasmid further comprise other components including but not limited to C-terminal hemagglutinin tag, stabilizing elements (to minimize plasmid loss in vivo), antibiotic resistance genes, and terminators.

Stabilizing elements include but are not limited to the hok/sok system (Gerdes et al. 1986) and alp7 partitioning system (Derman et al. 2012).

Antibiotic resistance genes include but are not limited to resistance to ampicillin, tetracycline and kanamycin In some embodiments, the plasmid is high copy. In some embodiments, the plasmid is medium copy. In some embodiments, the plasmid is low copy.

The use of the separate plasmid allows for simpler cloning without the confounding effect of perturbing the SLC circuit.

Thus, plasmids can be manipulated easily by non-experts, when combined with an SLC-containing bacteria, i.e., programmable bacteria.

The use of high copy plasmids for therapeutic production allow for much greater therapeutic efficacy from the bacteria.

The resulting plasmid comprising the nucleic acid encoding the therapeutic agent is transformed into the programmable bacteria comprising the SLC by methods known in the art.

In some embodiments, the therapeutic agent is an inhibitor of an immune suppressor molecule, for example, an inhibitor of an immune checkpoint molecule. The immune system is finely regulated to protect from invading pathogens, while avoiding immune responses mounted against the host's own cells Immune checkpoint molecules help prevent the development of autoimmune diseases. Several cancer drugs aim to inhibit these checkpoints in order to activate the immune system and boost the patient's anti-tumor responses, thus allowing the immune system to mount immune responses against self-antigens on cancerous cells. However, altered immunoregulation can provoke immune dysfunction and lead to autoimmune disorders when administered systemically. The problem of immune dysfunction, e.g., the development of an undesired autoimmune response, can be addressed by delivering an immune checkpoint inhibitor or inhibitor of another immune suppressor molecule locally at the tumor site as accomplished by the programmable bacteria of the invention.

The immune checkpoint molecule to be inhibited can be any known or later discovered immune checkpoint molecule or other immune suppressor molecule. In some embodiments, the immune checkpoint molecule, or other immune suppressor molecule, to be inhibited is selected from TGF-β, CTLA-4, PD-1, PD-L1, PD-L2, TIGIT, VISTA, LAG-3, TIM1, TIM3, CEACAM1, LAIR-1, HVEM, BTLA, CD160, CD200, CD200R, CD39, CD73, CD86, B7-H3, B7-H4, IDO, TDO, KIR, and A2aR.

In some embodiments, the inhibitor of the immune suppressor molecule is an antibody.

In some embodiments, the inhibitor of the immune suppressor molecule is a nanobody. Nanobodies are single single-domain antibodies that are small in size (approximately 15 kDa), maintain strong binding affinity, and can be recombinantly produced in bacteria. These nanobodies address the issues of poor tumor penetration of some large checkpoint inhibitor antibodies in some forms of cancer such as lung. The nanobodies will also minimize immune-related adverse events (IRAE), particularly in combination with locally released LPS from SLC.

In some embodiments, the nanobodies target checkpoint inhibitors including but not limited to PD-1, PD-L1 and CTLA-4.

The use of the programmable bacteria to deliver the nanobodies circumvents several issues including that nanobodies have extremely short half-lives. Also sustained SLC mediated delivery ensures proper dosing. Lastly, nanobodies lack Fc-regions that mediate phagocytosis of cells expressing the target antigen. As shown herein the bacterial delivery enhanced CD47 blockade and induced local activation of phagocytic cells (through innate immune mechanisms) obviating the requirement for Fc-signaling.

In some embodiments, the programmable bacteria contain plasmids capable of producing one or more agents which inhibit immune checkpoint inhibitors, e.g., one, two, three, four, five, six or more plasmid that produce agents which inhibit immune checkpoint inhibitors.

In certain embodiments, the programmable bacteria produce an anti-PD-1 nanobody and a nanobody against one or more checkpoints selected from CTLA-4, PD-L1, PD-L2, TIGIT, VISTA, LAG-3, TIM1, TIM3, CEACAM1, LAIR-1, HVEM, BTLA, CD160, CD200, CD200R, CD39, CD73, B7-H3, B7-H4, IDO, TDO, KIR, and A2aR.

In certain embodiments, the programmable bacteria produce an anti-CTLA-4 nanobody and a nanobody against one or more checkpoints selected from PD-1, PD-L1, PD-L2, TIGIT, VISTA, LAG-3, TIM1, TIM3, CEACAM1, LAIR-1, HVEM, BTLA, CD160, CD200, CD200R, CD39, CD73, B7-H3, B7-H4, IDO, TDO, KIR, and A2aR.

CD47 is a cell surface molecule implicated in cell migration and T cell and dendritic cell activation. CD47 is a widely recognized "don't eat me" signal that inhibits phagocytosis by macrophages upon binding to its ligand SIRPα. Importantly, CD47 is upregulated on multiple tumors, and treatment with anti-CD47 monoclonal antibodies has demonstrated efficacy as an immunotherapeutic when delivered at high doses in a lymphodeficient setting.

As shown herein, the inhibition of CD47 induced local activation of phagocytic cells. Thus, a further embodiment is the therapeutic agent is an inhibitor of CD47, including but not limited to antibodies and nanobodies. In further embodiments, the therapeutic agent is an inhibitor of SIRPα, including but not limited to antibodies and nanobodies.

In some embodiments, the therapeutic agent is an immunostimulatory molecule including but not limited to chemokine and cytokines. These molecules include but are not limited to CCL2, CXCL9, CXCL16, IL-18, IL-15, GM-CSF, IL-2, IL-15, IL-12, IL-7, IL-21, TNF, and interferon gamma (IFN-gamma).

In some embodiments, the therapeutic agent is heterodimer comprising subunits from more than one chemokine or cytokine. An example of such a heterodimer is IL12p70, a heterodimer comprised of IL12p40 and IL12p35. In some embodiments, the nucleic acid encoding the heterodimer is on one plasmid.

In yet further embodiments, the therapeutic agent is a toxin. In some embodiments, the toxins derive from bacteria. These toxins would include but are not limited to hemolysin E, melittin, anti-microbial peptides, diphtheria toxins, gelonin toxins, and anthrax toxins.

In a further embodiment, the therapeutic agent is a tumor antigen. As used herein the term "tumor antigen" is meant to refer to tumor-specific antigens, tumor-associated antigens (TAAs), and neoantigens. Tumor antigens are antigenic molecules produced in tumor cells that trigger an immune response in the host. These tumor specific antigens or tumor-associated antigens (TAAs) may be specific to a particular type of cancer cell or tumor cell and therefore the generated immune response will be directed to that cancer or tumor cell type. Examples of tumor antigens are ovalbumin and cytokeratin 19 (CK19). CK19 is a type I cytokeratin that has been suggested to be a suitable antigenic target for eliciting antitumor immunity. Cancer antigenic peptides are listed on databases including the Cancer Research Institute.

Tumor antigens are classified based on their molecular structure and source. Any protein produced in a tumor cell that has an abnormal structure due to mutation can act as a tumor antigen. Mutation of protooncogenes and tumor suppressors which lead to abnormal protein production are the cause of the tumor and thus such abnormal proteins are called tumor-specific antigens. Examples of tumor antigens include products of mutated oncogenes and tumor suppressor genes. Mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes. Thus, mutated antigens are only expressed by cancer as a result of genetic mutation or alteration in transcription.

In contrast, mutation of other genes unrelated to the tumor formation may lead to synthesis of abnormal proteins which are called tumor-associated antigens. These tumor-associated antigens are the products of other mutated genes that are overexpressed or aberrantly expressed cellular proteins. These overexpressed/accumulated antigens are expressed by both normal and neoplastic tissue, with the level of expression highly elevated in neoplasia. It should be noted that the classifications of "tumor specific antigen" and "tumor associated antigen" or of any of the "classes" described below are not meant to be mutually exclusive, there is overlap between the different "classes" with many tumor antigens falling into more than one "class"; thus the terminology is meant to be a general way of categorizing or grouping tumor antigens based on their characteristics and origin.

Oncofetal antigens are another important class of tumor antigens that are typically only expressed in fetal tissues and in cancerous somatic cells. Examples are alphafetoprotein (AFP) and carcinoembryonic antigen (CEA). These proteins are normally produced in the early stages of embryonic development and disappear by the time the immune system is fully developed. Thus self-tolerance does not develop against these antigens.

In addition to proteins, other substances like cell surface glycolipids and glycoproteins may also have an abnormal structure in tumor cells and could thus be targets of the immune system. Thus, other antigens are altered cell surface glycolipids and glycoproteins that are post translationally altered, e.g., have tumor-associated alterations in glycosylation.

Other examples include tissue differentiation antigens, which are antigens that are specific to a certain type of tissue. Mutant protein antigens are more specific to cancer cells because normal cells do not typically contain these proteins. Normal cells will display the normal protein antigen on their MHC molecules, whereas cancer cells will display the mutant version. Cell type-specific differentiation antigens are lineage-restricted (expressed largely by a single cancer histotype). There are also vascular or stromal specific antigens.

Cancer-testis antigens are expressed only by cancer cells and adult reproductive tissues such as testis and placenta. Cancer-testis antigens are antigens expressed primarily in the germ cells of the testes, but also in fetal ovaries and the trophoblast. Some cancer cells aberrantly express these proteins and therefore present these antigens, allowing attack by T-cells specific to these antigens. Example antigens of this type are CTAG1B and MAGEA1.

Proteins that are normally produced in very low quantities but whose production is dramatically increased in tumor cells, trigger an immune response. An example of such a protein is the enzyme tyrosinase, which is required for melanin production. Normally tyrosinase is produced in minute quantities but its levels are very much elevated in melanoma cells.

In addition to these types of antigens, there are also known neoantigens which can be used to stimulate an immune response. These antitumor T cells recognize unique antigenic features of tumor cells, characterized by mutations that permit uncontrolled growth and/or endow these cells with the ability to metastasize or survive within physiological locations outside of where the tumor initially originated. Such mutated-self, tumor-specific antigens (TSA), termed "neoantigens," represent the Achilles heel for a developing tumor. In fact, recent data demonstrate immunodominant T cell reactivities directed against mutated neoantigens following PD-1 blockade. Thus, the identification of a patient's unique neoantigen repertoire provides a novel therapeutic avenue through which to promote durable and systemic antitumor immunity.

The programmable bacteria themselves can stimulate an immune response in the tumor microenvironment, which immune response results in tumor cell lysis. Moreover, the programmable bacteria which comprise the SLC will release the neoantigens at lysis and allowing the neoantigens to be presented to antigen presenting cells, leading to immune-mediated antitumor responses. The killing of cancer cells can result in the release of novel cancer antigens (neoantigens) that may have been previously hidden to the immune system due to restricted presentation. Such neo-antigens can be taken up by local APCs in the context of a pro-inflammatory environment, which can trigger an immune response against the neo-antigen, killing the antigen-expressing cancer cells (including those cancer cells located at a distant site).

Additional Components

Additional components of the programmable bacteria would include other operons or circuits to allow control of the growth of the bacteria in certain environmental conditions found in tumors. By knocking out certain essential genes of a probiotic bacteria and placing their expression under the control of environmental sensors, the growth of the bacteria can be specified to the applicable tumor environment and regulated at off-target sites. Such a bacteria may include a tumor sensor for low oxygen, low pH, high lactate, and/or high $H_2O_2$ concentration, which are environment traits at the necrotic core of a solid tumor. The growth of the bacteria is controlled by the additional circuit which in turn regulates the SLC as the quorum sensing system of the SLC is sensitive to the growth of the bacterial population.

In some embodiments, the additional circuit is genomically integrated into the genome of the bacteria. In some embodiments the additional circuit is contained in a plasmid or plasmids. In some embodiments, the additional circuit is on a different plasmid than the SLC.

For example, lung cancer microenvironments are known to have elevated levels of reactive oxygen species (ROS) produced and secreted by metabolically disrupted cancer cells. In order to achieve growth specificity, in some embodiments, an essential bacterial gene can be knocked out and its expression placed under the control of the *E. coli* ROS stress regulator OxyR25 using the promoter of its target gene, e.g., katG26. Thus, bacteria will only be able to grow and divide when the presence of ROS enables expression of this essential gene. In some embodiments, the tunable regulatory region is a ROS-inducible regulatory region, and the transcription factor that senses ROS is OxyR. OxyR functions primarily as a global regulator of the peroxide stress response and is capable of regulating dozens of genes, e.g., genes involved in $H_2O_2$ detoxification (katE, ahpCF), heme biosynthesis (hemH), reductant supply (grxA, gor, trxC), thiol-disulfide isomerization (dsbG), Fe—S center repair (sufA-E, sufS), iron binding (yaaA), repression of iron import systems (fur)" and "OxyS, a small regulatory RNA. In further embodiments, the transcription factor is PhrR, RosR or SoxR.

A further example is tumor microenvironments that are hypoxic. To incorporate added levels of specificity and safety for translatability, a genetic circuit that requires hypoxic conditions for growth can be engineered in the bacteria. In this system, oxygen binds to the fumarate and nitrate reductase (FNR) monomers at physiological oxygen levels. Under hypoxic conditions, no oxygen is available for FNR binding, which results in dimerization and activation of FNR regulated promoters. Bacterial promoters including but not limited to FF+20 and Pvgb, which sense 0.5-5% oxygen in the tumor environmental range can be used in these circuits.

In other embodiments, alternative oxygen dependent promoters can be used including but not limited to DNR.

Administration, Dosing and Pharmaceutical Compositions

As discussed above, the present disclosure provides a pharmaceutical composition comprising a therapeutically effective amount of programmable bacteria in any form described herein and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

The pharmaceutical compositions may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The programmable bacteria may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, sub-cutaneous, intratumoral, peritumor, immediate-release, pulsatile-release, delayed-release, or sustained release).

Suitable dosage amounts for the programmable bacteria may range from about $10^4$ to $10^{12}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The programmable bacteria may be administered intravenously, e.g., by infusion or injection. Alternatively, the programmable bacteria may be administered intratumorally and/or peritumorally. In other embodiments, the programmable bacteria may be administered intra-arterially, intramuscularly, or intraperitoneally. In some embodiments, the programmable bacteria colonize about 20%, 30%, 40%, 50%, 60%, 70%, 80%, 90% or more of the tumor. In some embodiments, the programmable bacteria are co-administered with a PEGylated form of rHuPH20 (PEGPH20) or other agent in order to destroy the tumor septae in order to enhance penetration of the tumor capsule, collagen, and/or stroma.

The programmable bacteria may be administered via intratumoral injection, resulting in bacteria that is directly deposited within the target tumor. Intratumoral injection of the programmable bacteria may elicit a potent localized inflammatory response as well as an adaptive immune response against tumor cells.

Depending on the location, tumor type, and tumor size, different administration techniques may be used, including but not limited to, cutaneous, subcutaneous, and percutaneous injection, therapeutic endoscopic ultrasonography, or endobronchial intratumor delivery. In some embodiment, other techniques, such as laproscopic or open surgical techniques are used to access the target tumor.

Prior to the intratumor administration procedures, sedation in combination with a local anesthetic and standard cardiac, pressure, and oxygen monitoring, or full anesthesia of the patient is performed.

For some tumors, percutaneous injection can be employed, which is the least invasive administration method. Ultrasound, computed tomography (CT) or fluoroscopy can be used as guidance to introduce and position the needle. Single insertion points or multiple insertion points can be used in percutaneous injection protocols. Using a single insertion point, the solution may be injected percutaneously along multiple tracks, as far as the radial reach of the needle allows. In other embodiments, multiple injection points may be used if the tumor is larger than the radial reach of the needle.

Therapeutic endoscopic ultrasonography (EUS) is employed to overcome the anatomical constraints inherent in gaining access to certain other tumors. EUS-guided fine needle injection (EUS-FNI) has been successfully used for antitumor therapies for the treatment of head and neck, esophageal, pancreatic, hepatic, and adrenal masses. EUS-FNI has been extensively used for pancreatic cancer injections.

Intratumoral administration for lung cancer, such as non-small cell lung cancer, can be achieved through endobronchial intratumor delivery methods.

The clinically used and most well-known bacteria cancer therapy, Bacille Calmete-Guerin (BCG), has been used as the standard of care for bladder cancer for several decades (Redelman et al. 2014). It is delivered as a local, intravesical therapy for bladder cancer, and has been explored as an intra-tumoral therapy for primary and metastatic melanoma, head and neck cancers, and is in clinical trials for recurrent gliomas in the brain.

The dose to be injected is derived from the type and size of the tumor. The dose of the programmable bacteria is typically lower, e.g., orders of magnitude lower, than a dose for systemic intravenous administration.

The volume injected into each lesion is based on the size of the tumor. To obtain the tumor volume, a measurement of the largest plane can be conducted. The estimated tumor volume can then inform the determination of the injection volume as a percentage of the total volume. For example, an injection volume of approximately 20-40% of the total tumor volume can be used.

In some embodiments, the treatment regimen will include one or more intratumoral administrations. In some embodiments, a treatment regimen will include an initial dose, which followed by at least one subsequent dose. One or more doses can be administered sequentially in two or more cycles.

For example, a first dose may be administered at day 1, and a second dose may be administered after 1, 2, 3, 4, 5, 6, days or 1, 2, 3, or 4 weeks or after a longer interval.

Additional doses may be administered after 1, 2, 3, 4, 5, 6, days or after 1, 2, 3, or 4 weeks or longer intervals. In some embodiments, the first and subsequent administrations have the same dosage. In other embodiments, different doses are administered. In some embodiments, more than one dose is administered per day, for example, two, three or more doses can be administered per day.

The programmable bacteria may be administered orally and formulated as tablets, pills, dragees, capsules, liquids, gels, syrups, slurries, and suspensions. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, poly-acrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the programmable bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

In some embodiments, enteric coating materials may be used, in one or more coating layers (e.g., outer, inner and/o intermediate coating layers). Enteric coated polymers remain unionised at low pH, and therefore remain insoluble. But as the pH increases in the gastrointestinal tract, the acidic functional groups are capable of ionisation, and the polymer swells or becomes soluble in the intestinal fluid.

In another embodiment, the pharmaceutical composition comprising the programmable bacteria may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the programmable bacteria are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the programmable bacteria of the invention are well known in the art.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The programmable bacteria may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The programmable bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard methods.

The routes of administration and dosages described are intended only as a guide. The optimum route of administration and dosage can be readily determined by a skilled practitioner. The dosage may be determined according to various parameters, especially according to the location of the tumor, the size of the tumor, the age, weight and condition of the patient to be treated and the route and method of administration.

Methods of Treatment

It is contemplated that the programmable bacteria can be used to treat and cure any cancer. In some embodiments the cancer is a primary cancer. In some embodiments the cancer is a metastasized cancer. In some embodiments the cancer is a solid tumor.

Thus, one embodiment is a method of treating or curing cancer in a subject comprising administering to the subject a therapeutically effective amount of programmable bacteria comprising at least one synchronized lysis circuit contained in a single operon and at least one plasmid producing a therapeutic agent or a therapeutically effective amount of a composition or solution comprising programmable bacteria comprising at least one synchronized lysis circuit contained in a single operon and at least one plasmid producing a therapeutic agent.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include melanoma, lung cancer, head and neck cancer, renal cell cancer, colon cancer, colorectal cancer, squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, endometrial carcinoma, myeloma (such as multiple myeloma), salivary gland carcinoma, kidney cancer such as renal cell carcinoma and Wilms' tumors, basal cell carcinoma, prostate cancer, vulval cancer, thyroid cancer, testicular cancer, and esophageal cancer.

A "tumor" refers to the mass of tissue formed as cancerous cells grow and multiply, which can invade and destroy normal adjacent tissues. Cancer cells can break away from a malignant tumor and enter the bloodstream or lymphatic system, such that cancer cells spread from the primary tumor to form new tumors in other organs.

A "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors Non-limiting examples of preferred cancers for treatment or cure by the programmable bacteria include breast, melanoma (e.g., metastatic malignant melanoma), renal cancer (e.g., clear cell carcinoma), prostate cancer (e.g., hormone refractory prostate adenocarcinoma), pancreatic adenocarcinoma, colon cancer (CRC), lung cancer (e.g., non-small cell lung cancer), esophageal cancer, squamous cell carcinoma of the head and neck, liver cancer, ovarian cancer, cervical cancer, thyroid cancer, glioblastoma, glioma, and more generally solid tumors. Additionally, the programmable bacteria can be used to treat refractory or recurrent malignancies whose growth may be inhibited using compositions described herein.

It has been shown herein that the programmable bacteria selectively colonize in liver metastases as well as producing a systemic effect. Thus one embodiment is a method of treating or curing metastatic cancer in a subject comprising administering to the subject a therapeutically effective amount of programmable bacteria comprising at least one synchronized lysis circuit contained in a single operon and at least one plasmid producing a therapeutic agent or a therapeutically effective amount of a composition or solution comprising programmable bacteria comprising at least one synchronized lysis circuit contained in a single operon and at least one plasmid producing a therapeutic agent.

Additionally, the production of such cytokines is specifically advantageous for tumors such as colorectal because they are considered "cold" due to overproduction of prostaglandins that dampen the immune response (Sandage et al. 2017). For this reason, colorectal cancer has demonstrated only modest responses to checkpoint blockade. Therefore, administration of checkpoint blockade nanobodies in vehicles that might lead to more immune cell recruitment enhances therapeutic responses which would be otherwise difficult to attain for "cold" cancers.

Thus, a further embodiment is a method of treating or curing a cancer which demonstrates only a modest response to anti-cancer therapeutic agents in a subject comprising administering to the subject a therapeutically effective amount of programmable bacteria comprising a at least one synchronized lysis circuit contained in a single operon and at least one plasmid producing a therapeutic agent or a therapeutically effective amount of a composition or solution comprising programmable bacteria comprising at least one synchronized lysis circuit contained in a single operon and at least one plasmid producing a therapeutic agent. These cancers include but are not limited to colorectal cancer.

A further embodiment is a method of inducing systemic adaptive immunity to limit the growth of untreated tumors in a subject comprising administering to the subject a therapeutically effective amount of programmable bacteria comprising a at least one synchronized lysis circuit contained in a single operon and at least one plasmid producing a therapeutic agent or a therapeutically effective amount of a composition or solution comprising programmable bacteria comprising at least one synchronized lysis circuit contained in a single operon and at least one plasmid producing a therapeutic agent. As shown herein, the programmable bacteria activated or induced systemic adaptive immunity resulting in the reduction of the growth untreated tumors, i.e., an abscopal effect.

A further embodiment of the present disclosure is methods of treating and curing cancer using two or more programmable bacteria described herein. As shown herein the combination of programmable bacteria comprising plasmids which produce therapeutic agents had enhanced and even synergistic therapeutic efficacy. In some embodiments, the programmable bacteria comprise plasmids which produce different types of therapeutic agents, i.e., nanobodies, toxins, tumor antigens, cytokines, and chemokines e.g., a first programmable bacteria comprises a plasmid which produces an anti-PD-L1 nanobody and the second programmable bacteria comprises a plasmid which produces a hemolysin toxin. In some embodiments, the programmable bacteria comprise plasmids which produce the same type of therapeutic agents, i.e., nanobodies, toxins, tumor antigens, cytokines, and chemokines, but are different agents, e.g., a first programmable bacteria comprises a plasmid which produces an anti-PD-L1 nanobody and the second programmable bacteria comprises a plasmid which produces an anti-CTLA nanobody. In some embodiments, the two or more programmable bacteria are in different compositions or solutions. In some embodiments, the two or more programmable bacteria are in the same composition or solution.

In some embodiments, the second programmable bacteria are administered at the same time as the first programmable bacteria. In some embodiments, the second programmable bacteria are administered to the subject after the administration of the first programmable bacteria to the subject. The second programmable bacteria may be administered to the subject, for example, within one or more days or weeks of administration of the first composition to the subject. In some embodiments, the second programmable bacteria are administered to the subject at least one month after administration of the first programmable bacteria to the subject. In some embodiments, administration of the first programmable bacteria continues while the second programmable bacteria are administered to the subject.

In some embodiments, a third, fourth, fifth, sixth, seventh, etc. programmable bacteria can be administered to the subject. In some embodiments, the programmable bacteria comprise plasmids which produce different types of therapeutic agents, i.e., nanobodies, toxins, tumor antigens, cytokines, and chemokines e.g., a first programmable bacteria comprises a plasmid which produces an anti-PD-L1 nanobody and the second programmable bacteria comprises a plasmid which produces a hemolysin toxin and the third programmable bacteria comprises a plasmid which produces CXCL16. In some embodiments, the programmable bacteria comprise plasmids which produce the same type of therapeutic agents, i.e., nanobodies, toxins, tumor antigens, cytokines, and chemokines, but are different agents, e.g., a first programmable bacteria comprises a plasmid which produces an anti-PD-L1 nanobody and the second programmable bacteria comprises a plasmid which produces an anti-CTLA nanobody and a third programmable bacteria comprises a plasmid which produces an anti-CD47 nanobody. In some embodiments, the two or more programmable bacteria are in different compositions or solutions. In some embodiments, the two or more programmable bacteria are in the same composition or solution.

In some embodiments, the second, third, fourth, fifth, sixth, etc. programmable bacteria are administered at the same time as the first programmable bacteria. In some embodiments, the subsequent programmable bacteria are administered to the subject after the administration of the first programmable bacteria to the subject. The subsequent programmable bacteria may be administered to the subject, for example, within one or more days or weeks of administration of the first composition to the subject. In some embodiments, the subsequent programmable bacteria are administered to the subject at least one month after administration of the first programmable bacteria to the subject. In some embodiments, administration of the first programmable bacteria continues while the subsequent programmable bacteria are administered to the subject.

Further embodiments include methods and compositions for the treatment, cure and prevention of cancer wherein the programmable bacteria are used in combination with a therapeutically effective amount of other therapeutic agents including but not limited to chemotherapeutic agents, targeted chemotherapeutic agents and immunotherapy.

In these embodiments, the programmable bacteria improve the efficacy and causes the cancer to become more susceptible to other treatments, including but not limited to chemotherapeutic agents, targeted therapeutic agents and immunotherapy.

A "chemotherapeutic agent" or "chemotherapeutic drug" is a chemical compound useful in the treatment of cancer, regardless of mechanism of action. Classes of chemotherapeutic agents include, but are not limited to, microtubule-targeting moietys (MTAs), DNA damaging agents, alkylating agents, antimetabolites, spindle poison plant alkaloids, cytotoxic/antitumor antibiotics, topoisomerase inhibitors, antibodies, photosensitizers, and kinase inhibitors.

The chemotherapeutic agent may be natural or synthetic.

In some embodiments, the chemotherapeutic agent is a small molecule.

Targeted chemotherapeutic agents block specific proteins or genes. Targeted therapeutic agents include but are not limited to denosumab, romidepsin, ofatumumab, pazopanib, everlimus, nilotinib, temsirolimus, lapatinib, sunitinib, dasatinib, vorinostat, erlotinib, bevacizumab, cetuximab, bortezomib, gefitinib, ibritumomab, alemtuzumab, imatinib, gentuzumab, denileukin difitox, trastumab, rituximab, ramucirumab, ziv-aflibercept, panitumumab, and regorafenib.

Immunotherapy would include but is not limited to PD-1 inhibitors including pembrolizumab and nivolumab, and a CTLA-4 inhibitor including ipilimumab.

The methods and compositions described herein can be used in combination with other traditional cancer treatment or therapy.

Kits

The present invention also provides kits comprising any of the programmable bacteria described herein. In some embodiments, the programmable bacteria comprise one or more synchronized lysis circuits contained in a single operon. In some embodiments, the programmable bacteria further comprise one or more plasmids which produce a therapeutic agent.

A kit includes one or more components including, but not limited to, programmable bacteria described herein. Kits may further include a pharmaceutically acceptable carrier, as discussed herein. The programmable bacteria can be formulated as a pure composition or in combination with a pharmaceutically acceptable carrier, in a pharmaceutical composition.

In some embodiments, a kit includes programmable bacteria described herein in one container (e.g., in a sterile glass or plastic vial).

In some embodiments, a kit includes programmable bacteria described herein in one container (e.g., in a sterile glass or plastic vial) and a second or subsequent programmable bacteria described herein in another container (e.g., in a sterile glass or plastic vial).

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding the programmable bacteria may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

If the kit includes programmable bacteria comprising one or more synchronized lysis circuits contained in a single operon, the kit can further include reagents for constructing plasmids which produce therapeutic agents, including the plasmids, reagents for transfecting the programmable bacteria with the resulting plasmids, and instructions for use.

EXAMPLES

This invention will be better understood from the Experimental Details, which follow. However, one skilled in the art will readily appreciate that the specific methods and results discussed are merely illustrative of the invention as described more fully in the claims that follow thereafter.

Example 1—Bacteria Containing PD-L1 and CTLA4 Nanobody as the Deliverable Therapeutic Agent—Materials and Methods for Examples 2-6
Plasmid and Strains The circuit strains were cultured in LB media with their respective antibiotics (sc101*variant: 100 µg ml$^{-1}$ampicillin, p15A variant: 100 µg ml$^{-1}$ spectinomycin, colE1: 100 µg ml-$^{1}$ spectinomycin, and all with 50 µg ml$^{-1}$ spectinomycin and kanamycin for strains also transformed with PD-L1 therapeutic plasmid) with 0.2% glucose, in a 37° C. shaking incubator. CT26 and 4T1 mammalian cells were purchased from ATCC and cultured in RPMI supplemented with 10% fetal bovine serum and 1% penicillin/streptomycin. A20 cells were purchased from ATCC and cultured in RPMI supplemented with 10% fetal bovine serum and 1% penicillin/streptomycin and 0.01% 2-Mercaptoethanol. Mammalian cells were grown inside a 37° C. tissue culture incubator maintained at 5% $CO_2$. Plasmids were constructed using Gibson assembly cloning methods and integrated into the φ80 site of E. coli Nissle 1917 using the CRIM protocol (Haldimann and Wanner 2001). The EcN-SLC-hlyE construct was used in previous work (Din et al. 2016), while the PD-L1 Nb and CTLA4 Nb sequence was obtained from the online RCSB protein data bank and synthesized.

Antibodies

Antibodies used for in vivo experiments included anti-mouse PD-L1 (BioXCell cat: BE0101), Rat igG2b Isotype control (cat: BE0090), and anti-mouse CTLA4 (BioXCell cat: BE0164). Pre-conjugated primary antibodies used for flow cytometry and microscopy included Pe/Cy7 anti-mouse CD274 (Biolegend cat: 124313), Pe/Cy7 Rat IgG2b (Biolegend cat: 400617), Pe anti-mouse CD274 (Biolegend, cat: 155403), Pe Rat IgG2a isotype (BS biosciences cat: 557076), anti-HAAF 647 (R&D System cat: IC6875R-025), and mouse IgG1-AF 647 (R&D systems cat: IC200R).

For western blot an anti-HA high affinity (Roche, cat: 11867423001) and a rat HRP were used.

Immunofluorescence and Binding Kinetics

PD-L1 Nb protein non-lysing bacterial strains containing the PD-L1 Nb therapeutic plasmid were grown in a 50 mL LB culture with appropriate antibiotics to an optical density (OD) of 0.6 and then centrifuged at 3000 rcf for 5 minutes. The bacterial pellet was resuspended in 5 mL of RPMI media. Samples were frozen at −80° C. and thawed in a 30°

C. incubator 5 times and centrifuged at 3000 rcf for 5 minutes to remove bacterial debris. 1 mL of the resulting lysate was then filtered through a 0.2 micron filter.

Flow Cytometry

For flow cytometry, 1×10$^6$ CT26 cells were co-incubated in a 14 mL round bottom FACS compatible tube with a constant concentration of preconjugated PD-L1 Ab (1:800 for the 10F.9G2 clone and 1:200 for the MIH7 clone) and dilutions of the previously prepared bacterial lysate containing PD-L1 Nb (0.1%, 1%, 10%, 100% of full lysate) in a total working volume of 1 mL for 2 hours at room temperature. Samples were spun and washed with ice cold PBS and analyzed on an BD LSRII flow cytometer.

For flow cytometry on ex vivo tumor tissue, tumors were extracted for immunophenotyping on day 8 following bacteria treatment on days 0, 4, and 7. Lymphocytes were isolated from tumor tissue by mechanical homogenization and digestion with collagenase A (1 mg/ml, Roche) and DNAase I (0.5 ug/mL, Roche) in isolation buffer (RPMI 1640 supplemented with 5% FBS, 1% L glutamine, 1% penicillin/streptomycin, and 10 mM Hepes) for 1 hour at 37° C. Cells were then filtered through 100 um cell strainers and washed in isolation buffer before staining. A Ghost Dye cell viability staining was used as a live/dead marker. Extracellular antibodies used include: anti-B220 (BD 1:400), anti-CD4 (Tonbo), anti-CD8 (eBioscience 1:400) and anti-NKp46(BD 1:200). Cells were then fixed using FOXP3/transcription factor staining buffer set (Tonbo) as per the manufacturer's protocol and then stained intracellularly. Intracellular antibodies used include: anti-TCRβ (BD 1:400), anti-Ki67 (Thermo 1:400) and anti-FOXP3 (ebioscience 1:400). Samples were analyzed using a BD LSR Fortessa cell analyzer.

Single-stains and isotype controls were used for compensation of the dual stain. FlowJo was used for all data analysis.

Microscopy

For microscopy, 1×10$^6$ CT26 cells were stained on a poly-1-lysine coated glass flat bottom plate with appropriate antibodies for detection of PD-L1 expression (10F.9G2 clone). In a separate experiment, full bacterial lysate containing PD-L1 Nb was incubated on the monolayer of CT26 cells and probed with a pre-conjugated anti-HA antibody. A Nikon Eclipse Ti microscope was used for all microscopy and FIJI was used for any post-image analysis.

Characterization of PD-L1 Nb Expression and Release

To determine protein expression and functionality of the HA tag, PD-L1 Nb protein was released using the freeze/thaw method described above. A western blot was used for protein visualization and was performed by probing for 1 hour with the primary anti-HA antibody (1:800) and 1 hour with a rat HRP (1:4000) at room temperature. Protein was detected using a chemiluminescent substrate. For the characterization of protein release of the different lysing variants, bacterial strains with the different circuits were grown in a 50 mL culture. Every 3 hours for 12 hours, cultures were spun at 3000 rcf and 1 mL of supernatant was collected and stored at −80° C. 30 uL of the supernatants were run on the western blot and probed as described above for PD-L1 Nb expression.

Modeling

To further explore the population dynamics and therapeutic efficacy of a more translational probiotic-based platform, the ordinary differential equation model explored in the original synchronized lysis circuit system was built upon (Din et al. 2016).

The following set of ordinary differential equations were derived to describe the bacterial population number (N, equation[1]), total extracellular AHL (H, equation[2]), intracellular concentrations of the lysis protein E (L, equation [3]), intracellular concentrations of the LuxI protein (I, equation[4]), and intracellular concentrations of the PD-L1 Nb protein (P, equation[5]). In this system, bacteria grow logistically at a rate of μN to a maximum capacity, N$_0$ and lyse once at quorum. AHL is produced at a rate proportional to bacterial population and is cleared out at a rate of μ. The lysis protein is produced at a rate proportional to copy number and has a basal degradation (γL) and is also diluted as the bacterial population grows (μg). The luxI protein has similar dynamics but is further degraded by ClpXP machinery (γc). The therapeutic protein production is proportional to bacteria number and has basal degradation (γp) and is diluted as the bacterial population grows (μg). Internal production of LuxI and lysis protein is described by Plux (equation[6]) and the rate of cell degradation due to lysis is described by the hill function, γN (equation[7]).

$$\frac{dN}{dt} = \mu_N N \left(1 - \frac{N}{N_0}\right) - \gamma_N N \quad [1]$$

$$\frac{dH}{dt} = bNI - \frac{\mu H}{1 + N/N_0} \quad [2]$$

$$\frac{dL}{dt} = C_L P_{lux} - \gamma_L L - \mu_G L \quad [3]$$

$$\frac{dI}{dt} = C_I P_{lux} - \gamma_I I - \mu_G I - \gamma_c I \quad [4]$$

$$\frac{dP}{dt} = N P_{PDL1} - \gamma_P P - \mu_G P \quad [5]$$

$$P_{lux} = \alpha_0 + \frac{\alpha_H (H/H_0)^4}{1 + (H/H_0)^4} \quad [6]$$

$$\gamma_N = \frac{kL^n}{L_o^n + L^n} \quad [7]$$

Model Parameters Values

Figure 2B:
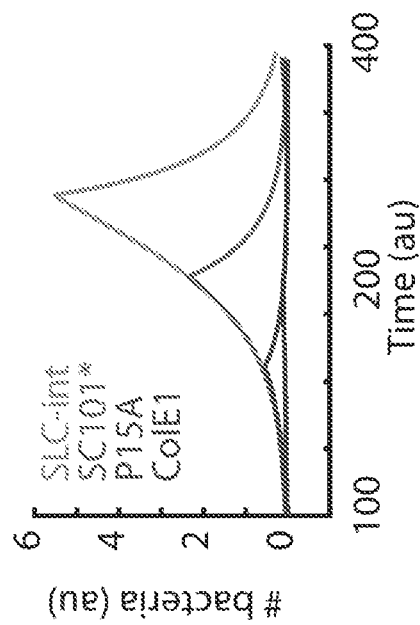
FIG. 2B shows a computational simulation of one lysis event for the copy number variants over time (green: single integrant, red: low copy, blue: medium copy, black: high copy).
Figure 2C:
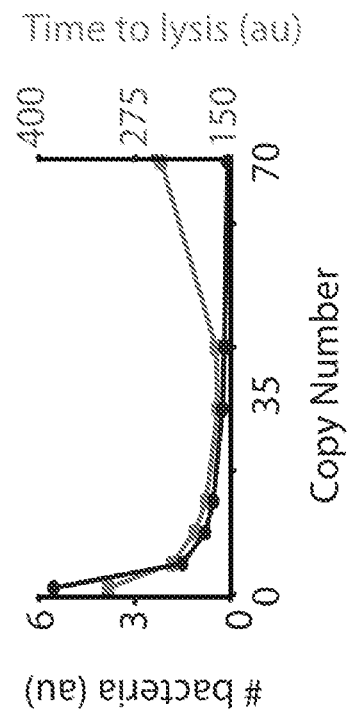
FIG. 2C shows the computational simulation of the number of bacteria needed to reach quorum as a function of copy number (left y axis: black) and time to first lysis event (right y axis: gray).
Figure 2D:
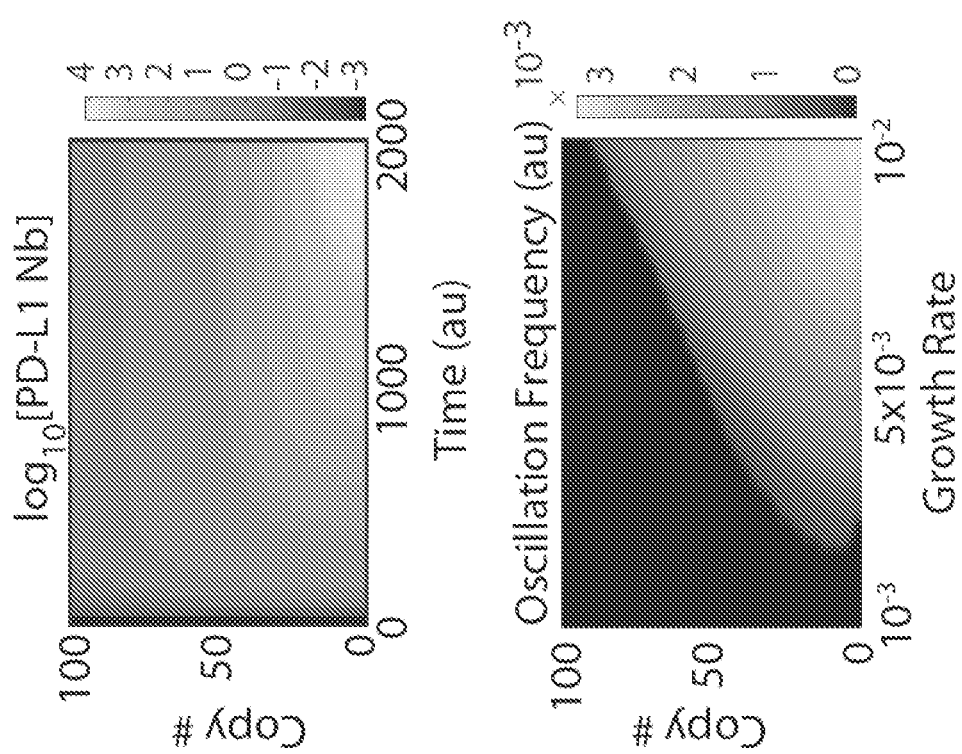
FIG. 2D (top panel) shows the simulated heatmap of the PD-L1 Nb protein produced (z-axis) as a function of both copy number (y-axis) and time (x-axis) and (bottom panel) the simulated heatmap of the oscillation frequency (z-axis) as a function of copy number (y-axis) and growth rate (x-axis).
Figure 2G:
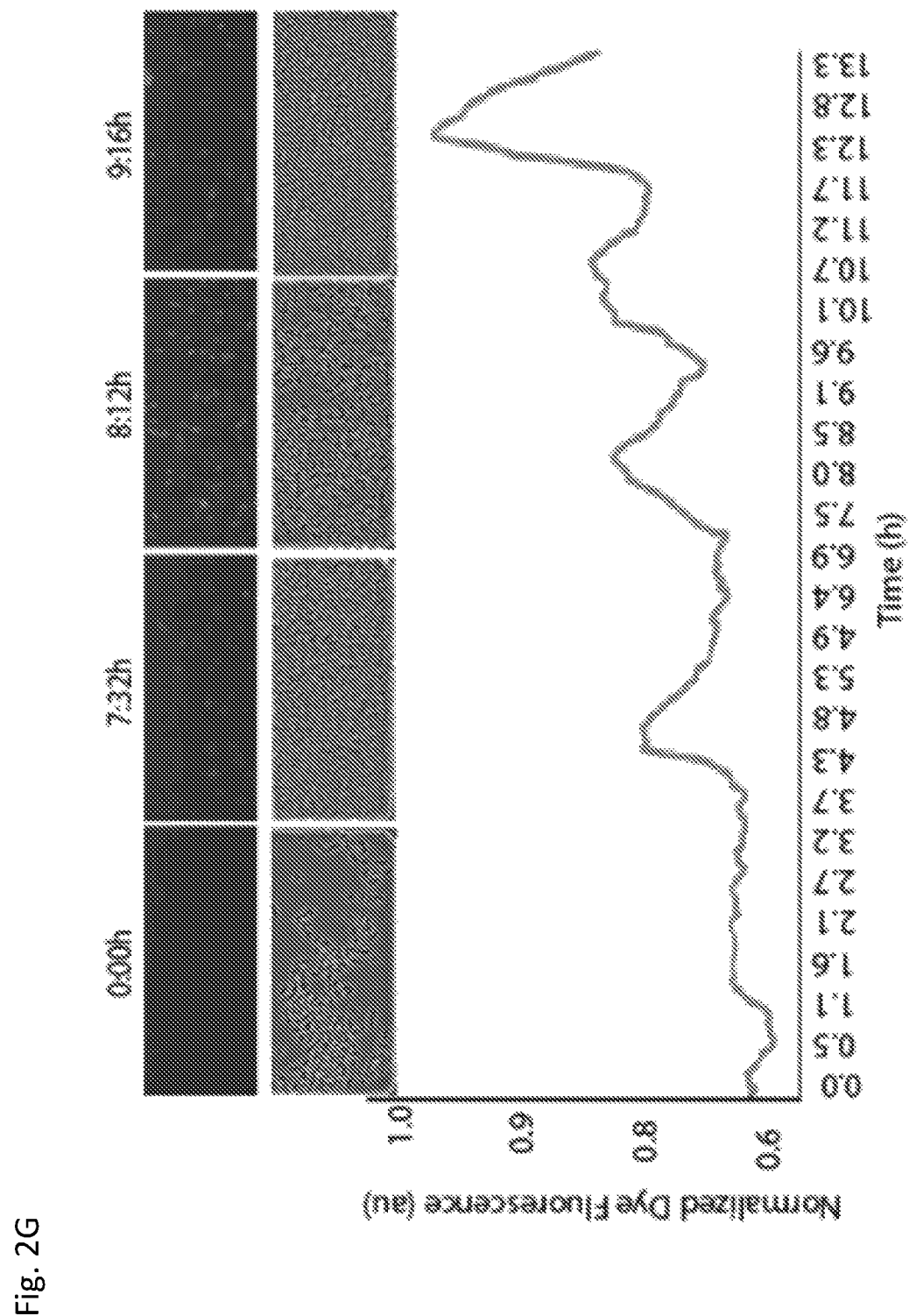
FIG. 2G shows the oscillatory behavior of the SLC-int strain in a microfluidic channel. The top panels show microscopy images from time-lapse microscopy of EcN-lux:SLC-int strain growing in a microfluidic device at different time points where fluorescence channel is shown on top and DIC channel is shown on bottom. The graph shows the fluorescence dynamics of a dye that binds to dead EcN-lux:SLC-int bacteria cells. Plot corresponds to dynamic behavior observed in the fluorescence channel of a time-lapse movie.

To explore the dynamics of our library of lysing variants, we iterated through a large range of copy numbers, CI and CL ranging from 1 to 100. Growth rate (μN) was experimentally-derived and the doubling time of approximately 30 minutes for SLC-int:PD-L1nb was used to calculate a growth rate of 0.023 min$^{-1}$ for in vitro plots (FIG. 2B, 2C, 2H, 2I, 2J, 2K) using the doubling time formula. Based on previous literature (Danino et al. 2012), the doubling time of bacteria increases to approximately 4 hours, which yielded a growth rate of 0.00289 min$^{-1}$ (FIG. 2D). Since growth rate and dilution due to cell growth was assumed to be equal μg was set equal to μN. Other parameter values include: α0=0.1; αH=50; h0=5; b=20; μg=1.5; L0=8; n=2; m=4; γL=1.5; K=0.05; γI=5; γC=12; and N0=10.

In Vivo Studies

Tumor Models

Animal experiments were performed on 6-8 week old female BALB/C mice from Taconic with bilateral subcutaneous hind flank tumors from an implanted mouse colorectal cancer cell line, CT26 or a mouse lymphoma cancer cell line, A20, or a mouse breast cancer cell line, 4T1. Tumor cells were prepared for implantation at a concentration of 5×10$^7$ cells/ml in RPMI without phenol red. Cells were implanted at 100 uL per flank, with each implant consisting of 5×10$^6$ cells. Tumors grew for approximately 10 days or until the diameter was 4-10 mm in diameter or volume was approximately 200 mm³ for CT26 and 4T1 tumors and approximately 150 mm³ for A20 tumors. All mice were randomized prior to treatment.

Bacteria Growth and Therapeutic Administration

Bacterial strains were grown overnight in LB media containing appropriate antibiotics and 0.2% glucose for less than 12 hours. The overnight was subcultured at a 1:100 dilution in 50 mL of fresh media with antibiotics and glucose and grown until an OD of approximately 0.05 to prevent bacteria containing SLC operon from reaching quorum. Bacteria were spun down at 3000 rcf and washed 3 times with sterile ice-cold PBS. Unless otherwise specified, bacteria were delivered intratumorally at a concentration of $5 \times 10^7$ cells/ml in PBS with a total of 30-40 uL injected per flank every 3-4 days (OD of 0.1 is equivalent to $1 \times 10^8$ cells/mL). The PD-L1 mAb and the CTLA4 mAb were injected intraperitoneally at a concentration of 200 ug/mouse and 100 ug/mouse, respectively.

Tumor and Bacteria Monitoring In Vivo

CT26 and 4T1 tumor volume was quantified using calipers to measure length, width, and height of each tumor with volumes being reported as L×W×H. A20 tumors were measured as (L×W)/2. Tumors were measured every 3 to 4 days and mouse weight was tracked to monitor overall mouse health. All bacterial strains used were luminescent, which could be measured with the In Vivo Imaging System (IVIS). Living Image software was used for luminescent quantification.

Statistical Analysis

Statistical tests were calculated in GraphPad Prism 7.0. The details of the statistical tests are indicated in the respective figure legends. Data was assumed to be normal and values were compared using a two-way ANOVA with appropriate correction applied for multiple comparisons.

Example 2—Construction and Characterization of a Probiotically-Expressed PD-L1 Nanobody A single-domain antibody, or nanobody (Nb), blocking PD-L1 was chosen from the RCSB Protein Data Bank as therapeutic cargo. Unlike antibodies with a molecular size of approximately 160 kDa, Nbs are only 15 kDa and lack an Fc region (which requires glycosylation by mammalian cells), and therefore Nbs can be produced recombinantly in bacteria (Bannas et al. 2017; Lee and Jeong 2015). Nbs provide multiple advantages, including their small size, which allows for increased diffusion within the tumor microenvironment and more rapid clearance from the bloodstream through glomerular filtration thereby reducing systemic toxicity (Hu et al. 2017). While faster blood clearance may suggest shorter therapeutic impact, the bacterial platform allows for continuous and intratumoral Nb production to improve upon this limitation.

The PD-L1 Nb sequence (SEQ ID NO: 1) as cloned downstream of a strong constitutive pTac promoter on a stabilized, high copy ColE1 origin or replication to allow for maximal gene expression. A human influenza hemagglutinin (HA) protein tag was added to 3' end of the Nb for in vitro visualization and an Axe/Txe stability mechanism was cloned into the vector to prevent plasmid loss during bacterial replication (FIG. 1A) (Fedorec et al. 2018). The plasmid was transformed into the probiotic strain, E. coli Nissle 1917, containing a genomically integrated luxCD-ABE cassette for bacterial tracking in vivo (EcN-Lux). E. coli Nissle 1917 was chosen as the therapeutic vehicle because of its proven safety, as it is currently prescribed for oral administration in humans, and for its easily manipulatable genome (Secher et al. 2017).

Figure 1C:
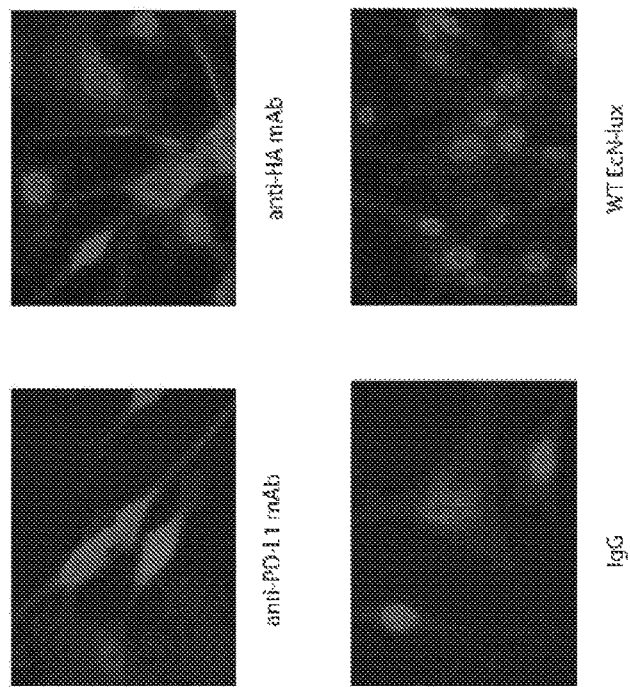
FIG. 1C shows immunofluorescence microscopy image of CT26 cells (purple: PD-L1, blue: nuclei). Left panel shows CT26 cells stained for PD-L1 expression with a flourescently-tagged 10F.9G2 mAb and its respective isotype. Right panel shows CT26 incubated with bacterial lysate containing PD-L1 Nb where the PD-L1 Nb is probed for using an anti-HA mAb.

Flow cytometry analysis (FIG. 1B) and immunofluorescence (FIG. 1C) were used to confirm PD-L1 expression on CT26 cells, a colorectal cell line that has a modest antitumor response to PD-L1 mAb (Sagiv-Barfi et al. 2015; Kim et al. 2014). To investigate the binding pattern of the probiotically-produced PD-L1 Nb, bacterial lysate containing the PD-L1 Nb was incubated on a monolayer of CT26 cells and an anti-HA mAb was used to probe for PD-L1 Nb binding. Imaging using fluorescence microscopy revealed a similar expression pattern to that of PD-L1 expression probed for by anti-PD-L1 mAb (FIG. 1C).

Figure 1E:
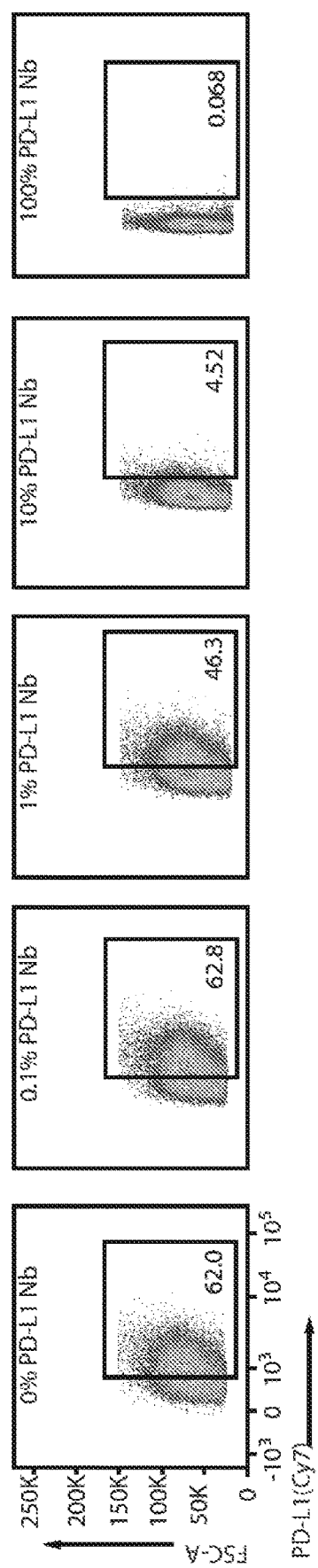
FIG. 1E are flow cytometry plots of CT26 populations, where CT26 cells were co-incubated with a constant concentration of Cy7-conjugated 10F.9G2 mAb and varying concentrations of bacterial lysates containing the PD-L1 Nb.

To quantify binding kinetics of the PD-L1 Nb, multiple dilutions of bacterial lysate containing the PD-L1 Nb were co-incubated on a monolayer of CT26 cells with a constant concentration of fluorescently-tagged anti-PD-L1 mAbs known to bind to either the 10F.9G2 or MIH7 epitope. It was observed that with a more diluted lysate concentration, an increase of the 10F.9G2 mAb fluorescence was observed (FIG. 1D, FIG. 1E). Notably, a very small fraction (approximately 5%) of the total lysate produced was needed to achieve binding to 50% of PD-L1+CT26 cells. However, no change in fluorescence of the MIH7 mAb was observed as a function of bacterial lysate (FIG. 1E), suggesting that the PD-L1 Nb therapeutic specifically binds to the 10F.9G2 epitope.

Example 3—Optimization of the Synchronized Lysis Circuit as a Controllable Release Mechanism Since a dose-dependent binding of the Nb to PD-L1 was observed, optimization of the therapeutic release was sought by building upon a recent synchronized lysis circuit (SLC), whereby a bacterial population lyses once a critical density is reached (Din et al. 2016). The SLC has been shown to aid in tumor-selective production, population limitation, and therapeutic release, serving multiple purposes critical for translational efforts. To make this circuit more stable, the original SLC two-plasmid system was combined into a single operon, one-plasmid system that then was genomically integrated into EcN-lux. In this optimized system, the quorum sensing plux promoter drives transcription of both quorum sensing genes, luxR and luxI, and the phage-derived lysis gene, φX174E (FIG. 2A). Use of only one promoter and one terminator allowed for this smaller module to be easily integrated and reduce repeated sequences that can lead to recombination.

Figure 2I:
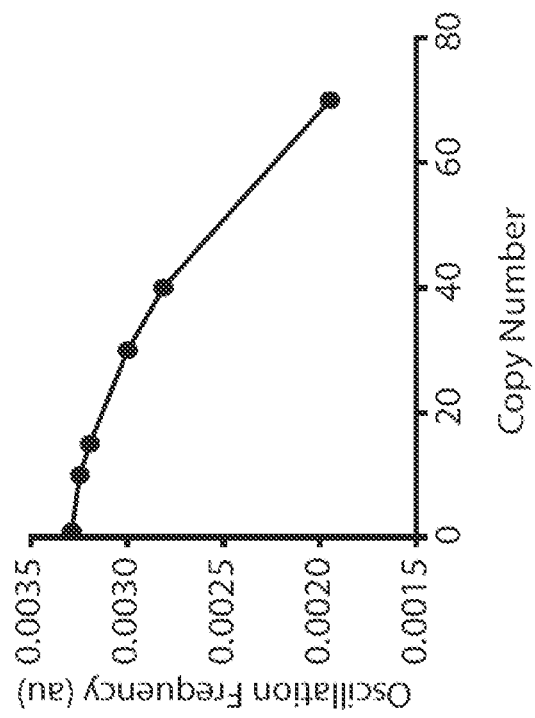
FIG. 2I shows the computational simulation of oscillation frequency over a given time frame as a function of copy number.
Figure 2H:
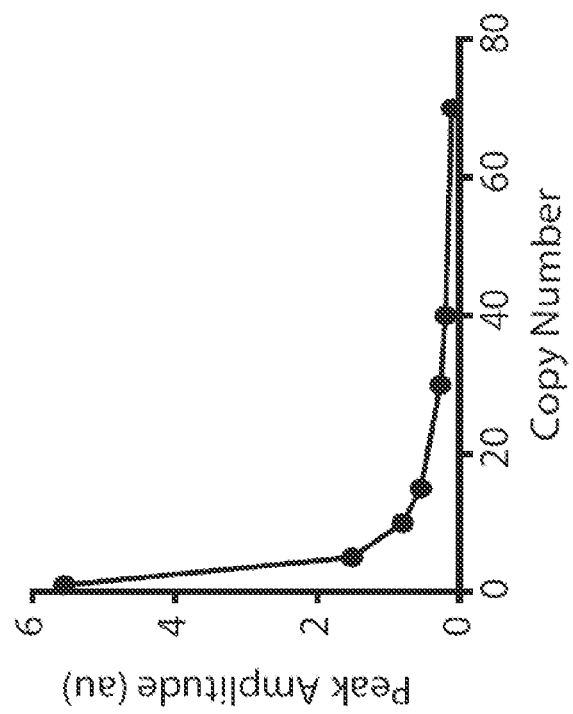
FIG. 2H shows the computational simulation of peak amplitude of bacterial population at quorum as a function of copy number.

While genomic integration of the SLC operon offers stability, it significantly reduces the copy number of quorum-sensing genes, prompting the exploration of how this reduction would affect therapeutic efficacy. Therefore, the behavior of each circuit variant was computationally modeled to further understand the effect of copy number of SLC dynamics. Using a system of ordinary differential equations (ODE), the dynamics of relevant variables in the lysing circuit was modeled, luxI, φ174E, bacteria number, the small molecule used for bacterial communication AHL (N-Acyl homoserine lactone), and therapeutic production. First the system was simulated to calculate two quantities: number of bacteria required for the first lysis event; and time required to reach lysis (FIG. 2B, FIG. 2C). It was observed that decreasing copy number of the SLC circuit monotonically increased the number of bacteria required to reach a quorum threshold before lysing. However, time to lysis displayed non-monotonic behavior, where the single copy variant produced a longer time to lysis than medium copy variants, but the high copy variant increased time to lysis again. The non-monotonic behavior was due to the higher level of basal lysis when high copies of the φ174E gene were present, resulting in slower growth and thus longer time to reach quorum. Further exploration of additional dynamic properties suggested that lower copy variants had a higher mean oscillation amplitude and frequency (FIG. 2H, FIG. 2I).

Figure 2K:
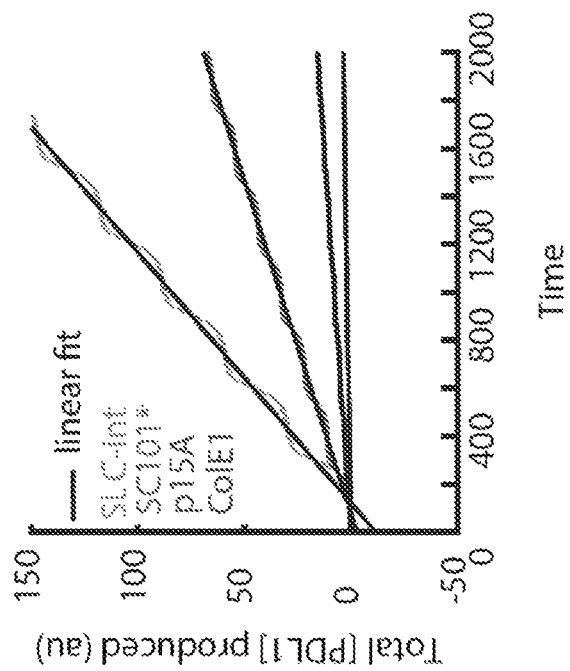
FIG. 2K shows computational simulation rate of PD-L1 Nb production for copy number variants.
Figure 2J:
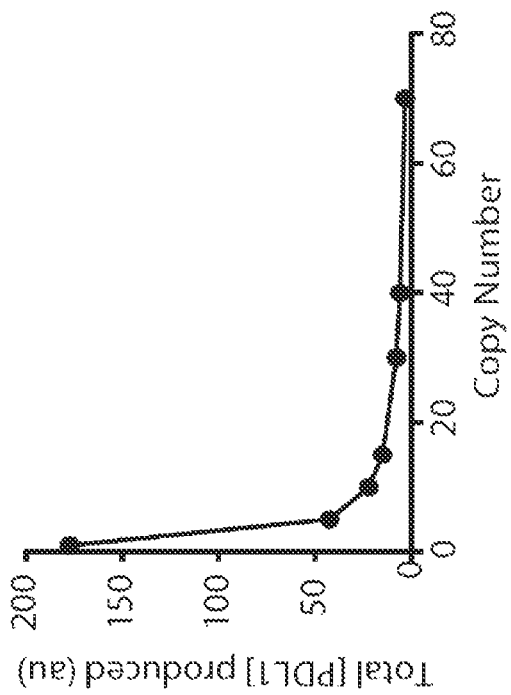
FIG. 2J shows the computational simulation of total PD-L1 Nb produced over a given time frame as a function of copy number.

The system's behavior at lower copy number variants motivated the exploration into the dynamics of therapeutic production as a direct function of population number over time, where it was found that lower copy variants produced more therapeutics in a given period of time and at a faster rate compared to higher copy variants (FIG. 2D, FIG. 2J, FIG. 2K). Furthermore, the rate of therapeutic production was time invariant, suggesting that this rate was a function of primarily copy number.

Next, it was sought to understand how the model could be used to predict bacterial dynamics in an in vivo setting. Previous studies have shown that bacterial growth kinetics are significantly slower in vivo, with the doubling time of the bacteria increasing from about 30 minutes in vitro to about 4 hours in vivo (Danino et al. 2012). Using the model, therapeutic production was simulated as a function of copy number and it was found that lower copy number variants were more robust to a changing growth rate parameter and produced relative more protein over a larger range of growth rate parameters compared to higher copy variants (FIG. 2D). Together these findings suggested that the SLC-int variant would result in maximal protein production across experimentally-relevant copy numbers.

To experimentally investigate system dynamics of the single operon SLC, a library of plasmid variants was built covering a range of copy numbers for the quorum sensing genes, including a single genomic integration of the operon into the φ80 site of the EcN-lux strain (SLC-int or EdN-Lux:SLC-int) (FIG. 2A).

Figure 2L:
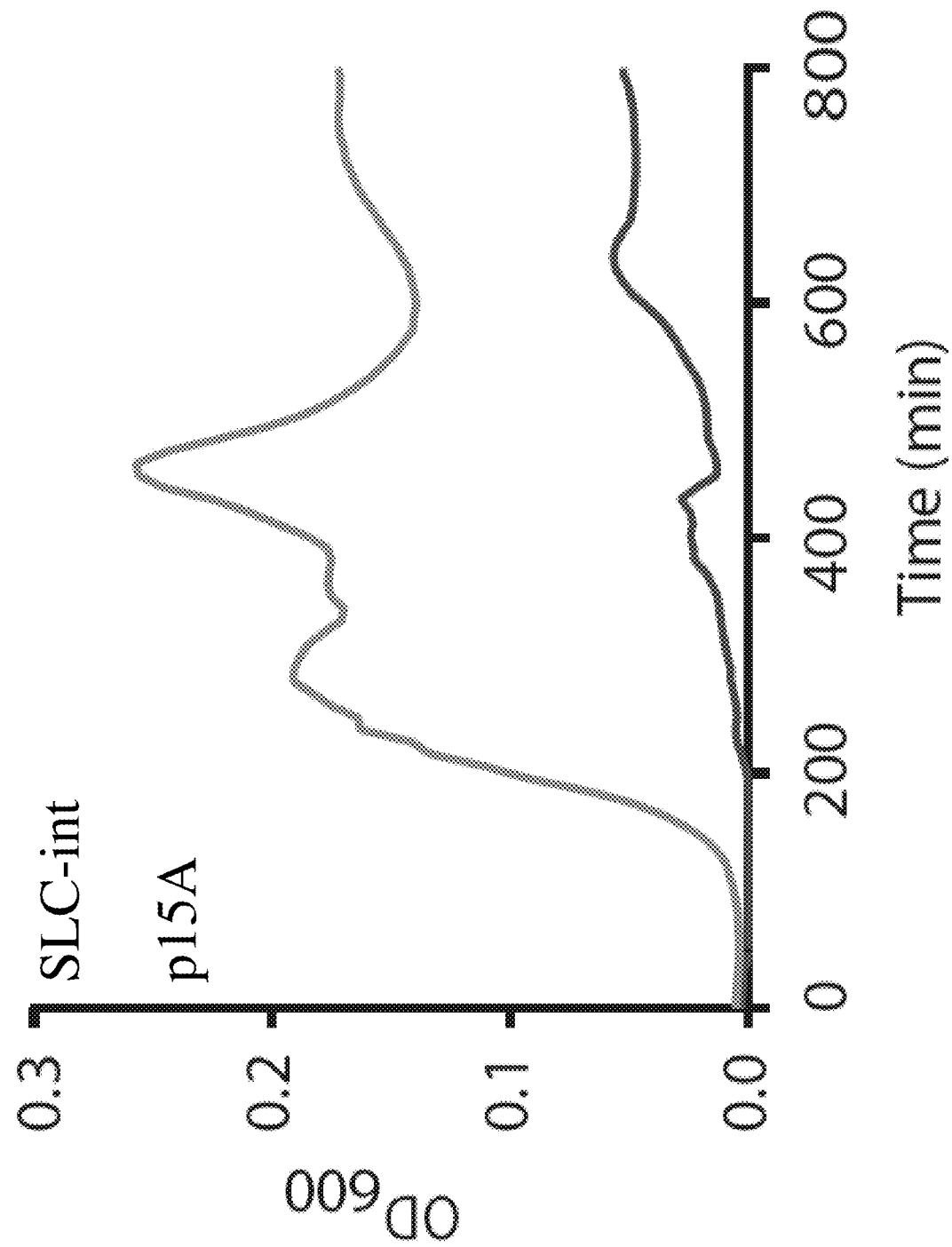
FIG. 2L shows experimental dynamics measured in a Tecan plate reader for SLC-int and p15A copy number variants showing multiple lysis events.

Tracking of bacteria concentration over time in 96 well plates suggested that more copies of the lysing circuit leads to lysis at a lower bacteria concentration with a rapid decay relationship relating these two variables (FIG. 2E, FIG. 2F). Furthermore, the time it took each variant to reach quorum generally suggested that a lower copy number required more time to reach a critical density and the relationship exhibited non-monotonic behavior, consistent with our simulations (FIG. 2F). To additionally visualize lysis events, the SLC-int variant was co-transformed with a constitutive plasmid (ptac:GFP) and imaged over time using fluorescence microscopy. Moreover, multiple oscillations for the SLC-int and SLC-P15A variants were observed by tracking the optical density over time in a plate reader (FIG. 2L).

Oscillatory dynamics of bacterial circuits are typically measured in microfluidic devices, where a constant flow of nutrients and removal of waste in a stable environment allows for clear observation and measurement of regular periodic oscillations. However, these experiments are low-throughput and are difficult to validate for multiple conditions, and do not necessarily represent the tumor environment. In this study, plate reader experiments were used, which allow for quick quantification of lysis along with determination of key features of the circuits, such as the time to lysis and OD at lysis. This allowed a quick development and comparison model and experimental conditions. These studies showed that periods, amplitudes, and total protein produced is decreased with increasing copy number.

Figure 2N:
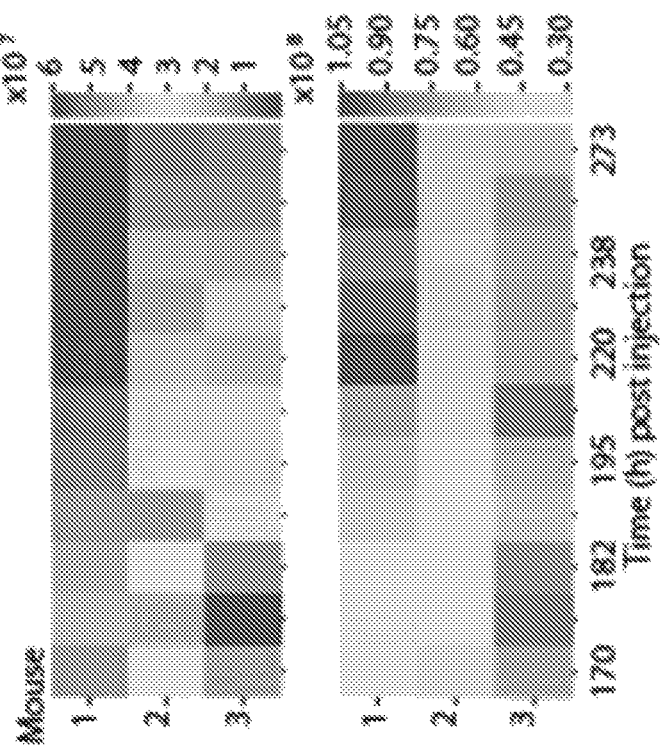
FIG. 2N are heatmaps showing total flux (in Radiance p/sec/cm2/sr) of the bacteria populations over time quantified from IVIS image.
Figure 2M:
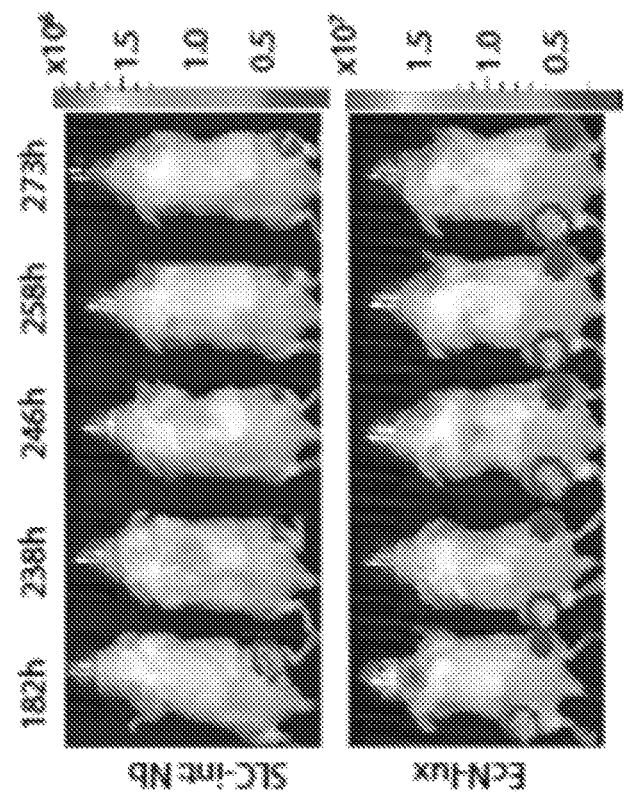
FIG. 2M show representative IVIS images from mice receiving the lysing SLC-int:Nb cocktail therapy (top panel) and non-lysing EcN-lux (bottom panel). Mice were implanted subcutaneously with $5 \times 10^6$ A20 cells on both hind flanks. When tumors reached approximately 150-200 mm$^3$, mice received one intratumoral injection of either EcN-lux or a combination of SLC-int:PD-L1nb+SLC-int:CTLA-4nb or one intraperitoneal injection of 200 ug/mouse anti-CTLA-4 mAb+ 100 ug/mouse anti-PD-L1 mAb.
Figure 20:
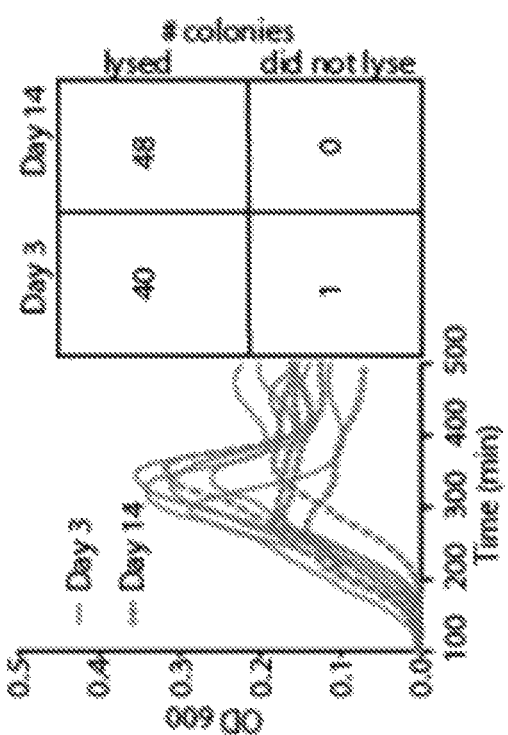

Next bacterial populations were tracked in vivo at longer time points and observed oscillations even as long as 2 weeks after a single bacterial injection (FIGS. 2M-2O). Over the course of treatment, robust oscillatory behavior was observed from the bacteria lysing treatment (SLC-int:Nb cocktail) using an In-vivo Imaging System (IVIS) and A20 mice treated with a cocktail or EcN-lux (FIG. 2M, FIG. 2N). This result was a very clear demonstration of the oscillatory behavior of the therapeutic system. Bacterial luminescence was low following bacterial lysis and the system was able to maintain robust oscillations over time. Additionally, 40-50 single colonies from tumors on day 3 and day 14 were tested, and 40/41 and 48/48 colonies were able to lyse in plate reader experiments (FIG. 2O).

Example 4—Determining the Optimal Release Mechanism for the PD-L1 Nanobody

Figure 3B:
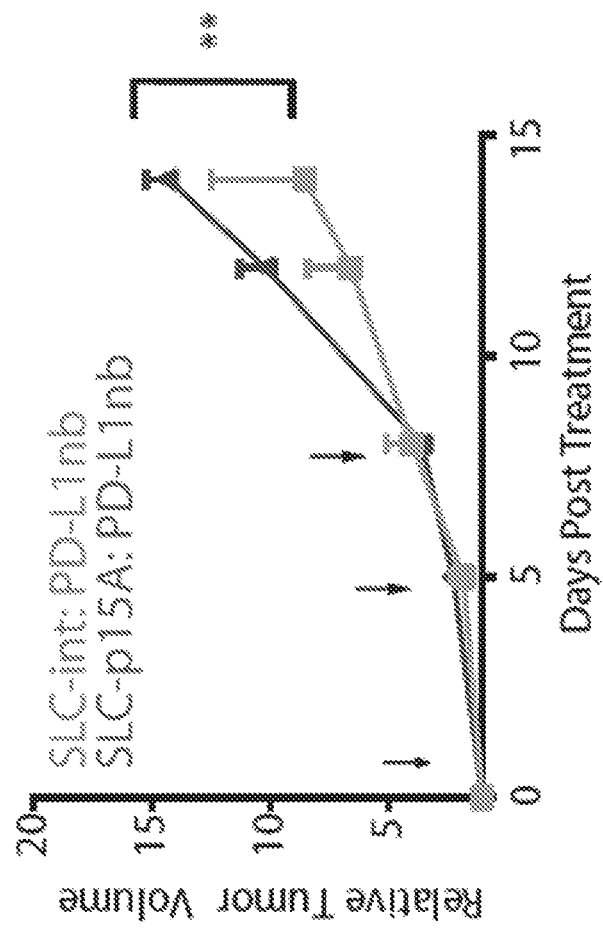
FIG. 3B shows a graph of mean relative tumor trajectory of mice receiving intratumoral injections of $5 \times 10^6$ bacteria of either SLC-int:PD-L1nb (light lines with squares) or SLC-p15A:PD-L1nb (dark lines with triangles). Arrows indicate days of intratumoral injection (N=6 tumors per group, ** $P=0.0065$, two-way ANOVA with Bonferroni post-test, error bars represent S.E.M)
Figure 3C:
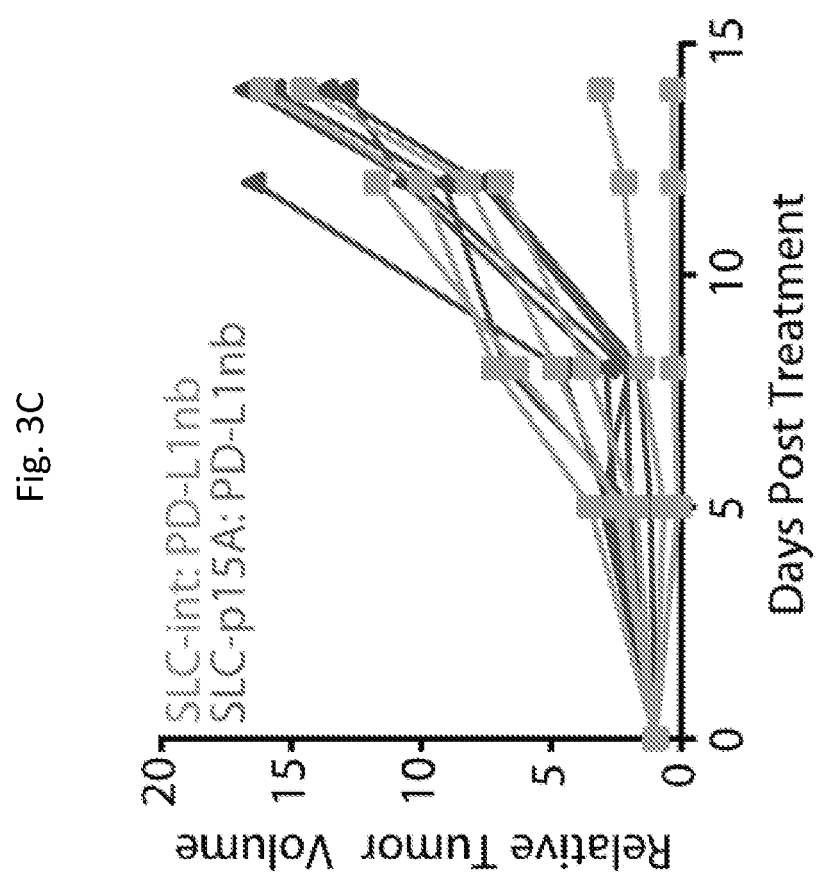
FIG. 3C is a graph of individual trajectories of mean tumor volume for CT26 tumor bearing BALB/c mice receiving injections of the SLC-int:PD-L1nb (light lines with squares) or SLC-p15A: PD-L1nb (dark lines with triangles) variant on day 0, 4 and 7 post treatment.
Figure 3E:
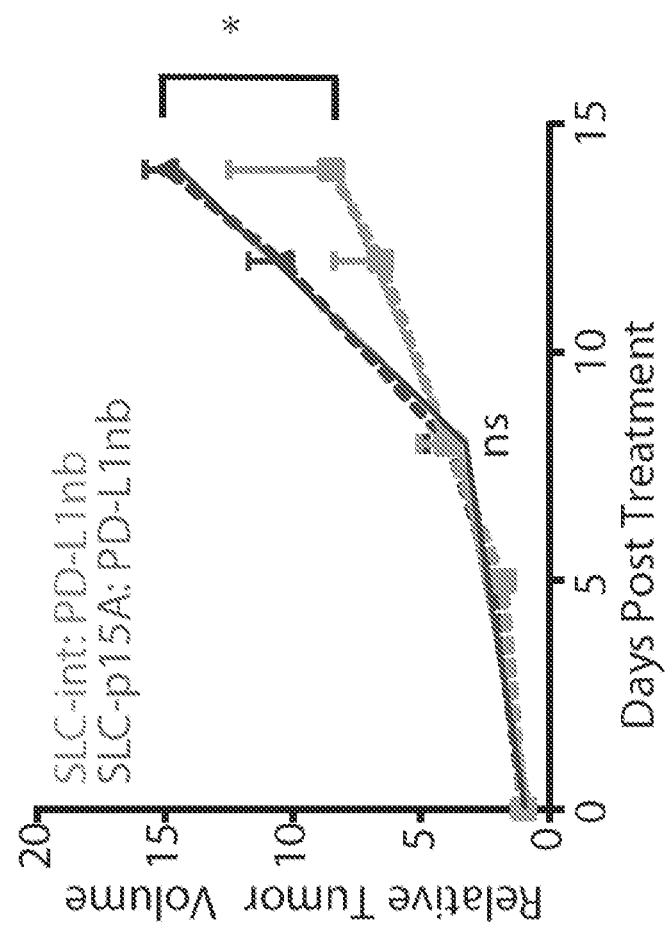
FIG. 3E shows the segmented linear regression (dotted lines) analysis of the relative tumor volume from 0-6 and 7-14 days for mice receiving injections of the SLC-int-PD-L1 Nb (light lines with squares) or SLC-p15A-PD-L1 Nb variant (dark lines with triangles) (* $P=0.0175$, error bars represent S.E.M of tumor volume measurements).

Considering the varying dynamics of the integrated and plasmid-based systems, both the SLC-int and p15A plasmid systems were engineered to produce the PD-L1 Nb. Production and release of the PD-L1 Nb was confirmed by western blot, and higher protein levels from the lowest copy SLC-int variant were observed as compared to the non-lysing EcN-lux strain transformed with the PD-L1 Nb plasmid at 16 hours (FIG. 3A). The therapeutic efficacy in vivo of both the SLC-int and p15A plasmid variants producing the PD-L1 Nb in a subcutaneous CT26 syngeneic mouse model were investigated. After 2 weeks, a moderate therapeutic difference was observed, with the SLC-int:PD-L1 Nb variant resulting in slower relative tumor growth (FIG. 3B). As previously reported, some tumors treated with an anti-PD-L1 monotherapy had a greater response than other tumors within the same treatment group. Therefore, individual mean trajectories were looked to, and found that for the SLC-int:PD-L1 Nb treated mice, 2 of the 6 tumors grew much slower, with 1 tumor trending towards complete regression (FIG. 3C). More interestingly, when therapeutic treatment ceased at day 7 and tumors were left untreated, the relative rate of growth for the p15A variant increased dramatically resulting in a significant difference in tumor growth rate (FIG. 3D, FIG. 3E). It was hypothesized that this difference in growth rate when treatment stopped was a result of a more stable SLC-int bacterial system with less plasmid burden. Previous research suggests that increasing bacterial plasmid burden may increase plasmid instability or lead to mutations, which could ultimately affect the therapeutic efficacy of the strain (Fedorec 2014).

Together these findings led to the use of the SLC-int strain as the release mechanism of the PD-L1 Nb therapeutic.

Example 5—Comparison of the SLC-Int:PD-L1 Nb System to a PD-L1 mAb

In the syngeneic mouse model of CT26, significant and comparable therapeutic efficacy was observed for both the 10F.9G2 mAb and SLC-int:PD-L1 Nb at day 4 (FIG. 4A). Analysis of individual mean tumor trajectories show that 1 out of 6 tumors in the 10F.9G2 mAb treated group showed minimal relative tumor growth, whereas at least 2 of the 8 tumors in the SLC-int:PD-L1nb treated group showed minimal growth or a reduction in tumor size (FIG. 4A). Furthermore, the distribution plot of the absolute tumor volumes for the 10F.9G2 mAb and the SLC-int:PD-L1nb were similar, with the average absolute tumor volume for the SLC-int: PD-L1 Nb treated group being slightly smaller than that of the 10F.9G2 mAb treated group (FIG. 4A). While there was no striking difference in tumor sizes between the two anti-PD-L1 treatment groups, histological analysis indicated a higher dirty necrosis score in bacteria-treated tumors, suggesting that tumors treated with the SLC-nt:PD-L1nb had less viable tissue and more neutrophils present in their tumor microenvironment compared to the anti-PD-L1 mAb group (FIG. 4B).

Figure 5D:
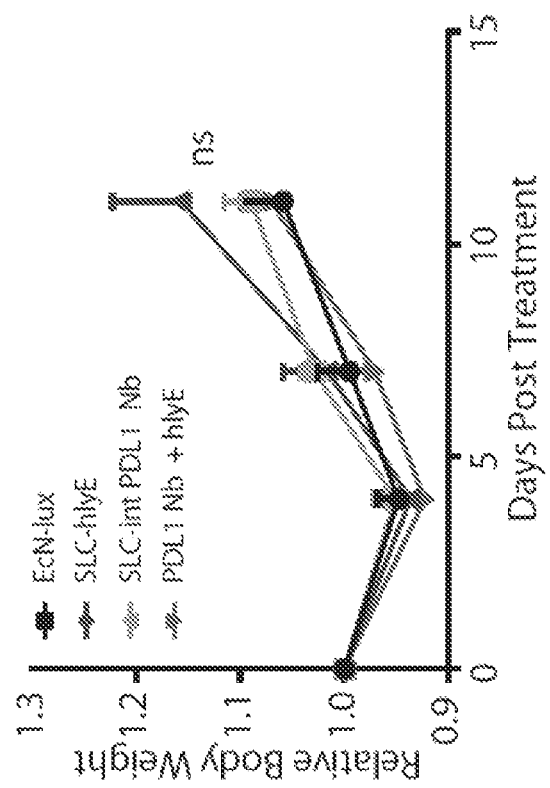
FIG. 5D is a graph of the mean relative body weight of CT26 tumor bearing BALB/c mice treated with EcN-SLC-hlyE (dark line with squares), SLC-int-PD-L1 Nb (light line with triangles), or an equal parts cocktail of EcN-SLC-hlyE and SLC-int-PD-L1 Nb strains (medium line with upside down triangles) over time (error bars represent S.E.M).
Figure 5E:
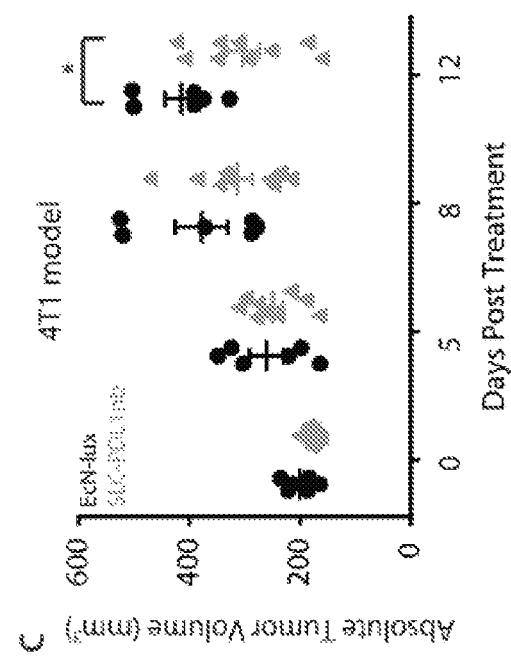
FIG. 5E shows graph of absolute tumor volumes of BALB/c mice implanted subcutaneously with $5 \times 10^6$ 4 T1 cells on both hind flanks. When tumors reached approximately 200 mm$^3$, mice received intratumoral injections of $5 \times 10^6$ bacteria every 3-4 days of either EcN-lux or SLC-PD-L1nb N=6-8 per group, *$P=0.0199$, two-way ANOVA with Bonferroni post-test, error bars represent S.E.M.
Figure 5F:
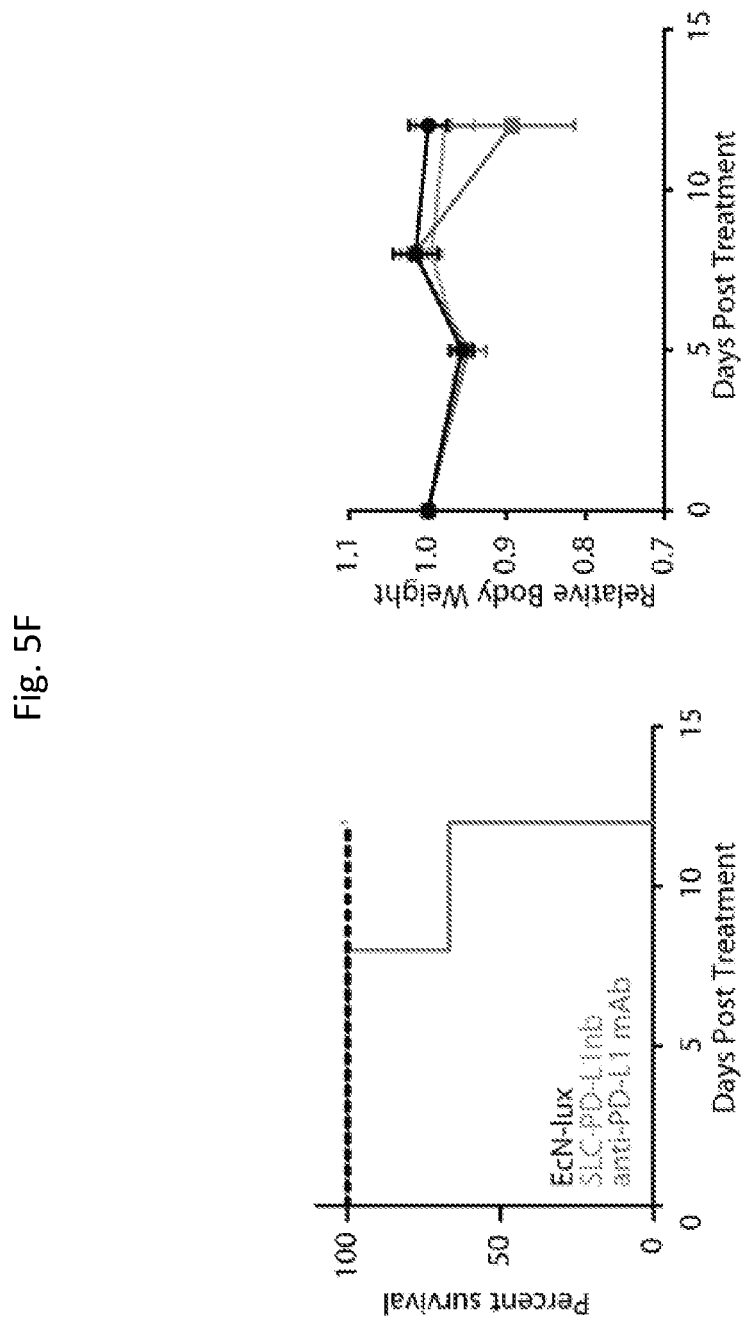
FIG. 5F shows graph of mouse survival and mean relative body weight following $5 \times 10^6$ bacteria (either EcN-lux or SLC-PD-L1nb) dosed on days 0, 5, and 8 days post treatment, and systemically delivery mAb dosed (200 ug 10F.9G2mAb/mouse) on days 0, 5, 8 and 12. Severe toxicities in weight and body conditions of antibody treated mice were observed, leading to death or required euthanasia of all mice within two weeks.

The versatility of the probiotic platform was explored by comparing the therapeutics effects of EcN-lux: SLC-PD-L1 Nb and the 10F.9G2 mAb on a syngeneic hind flank mouse model of triple negative breast cancer (Balb/c-4T1), where it was observed severe toxicity and animal death after only three PD-L1 mAb doses (FIG. 5F). After the second dose of the PD-L1 mAb, the body condition of the mice visibly deteriorated with one-third of the mice losing more than 10% of their weight and subsequently remained untreated for the rest of the trial. After the third dose, the mice with the continued treating with the PD-L1 mAB died and the remaining mice, having never recovered body condition after the second dose, were euthanized (FIG. 5F).

In contrast, mice receiving the EcN-lux control and EcN-lux-SLC:PD-L1nb had no change in body condition and appeared healthy throughout the trial (FIG. 5F). Toxicity to anti-PD-L1 monotherapy treatment has been previously reported in this breast cancer model, but here it was demonstrated that a probiotically-produced PD-L1 Nb mitigates this observed toxicity. Furthermore, the programmable bacteria demonstrated moderate efficacy when compared to the WT EcN-lux control, suggesting that programmable bacteria delivery maintained efficacy while reducing toxicity (FIG. 5E).

Example 6—Immunotherapeutic Combination Therapies

As seen in literature, anti-PD-L1 mAbs are not strikingly effective when used as just a monotherapy (Sagiv-Barfi et al. 2015; Kim et al. 2014). Therefore, combinations to enhance therapeutic efficacy of the engineered SLC-int:PD-L1 Nb probiotic therapy in the CT26 and A20 model were tested.

The bacterially-expressed hemolysin exotoxin (hlyE) was chosen for combination with SLC-int:PD-L1 Nb due to its ability to lyse mammalian cells and potentially release neoantigens that could then be recognized by infiltrating T cells. Furthermore, previous studies have demonstrated moderate efficacy of the hlyE as a monotherapy in mouse models of colorectal cancer (Din et al. 2016). The combination of SLC-int:PD-L1Nb and EcN-lux producing hlyE (EcN-SLC-hlyE) in equal parts significantly slowed tumor growth when compared to the individual therapies (FIG. 5A, FIG. 5B, FIG. 5C). A distribution plot of individual tumor volumes for each treatment group suggested that at the end of the treatment, the absolute tumor volumes for mice treated with the combination therapy were smaller (FIG. 5B). The overall effect of the combination therapy was more apparent in the individual trajectories, where more mice responded and grew slower over time (FIG. 5C). To quantify the therapeutic response of the combination therapy effect versus individual therapy effects, partial responders were considered as tumors with an absolute final volume less than that of the mean of absolute tumor volumes of the EcN-lux treated tumors on the final measurement day. About 2 weeks after treatment began, about 60% of the SLC-int:PD-L1 Nb treated tumor responded, about 25% of the EcN-SLC-hlyE treated tumors responded, and about 100% of the tumors treated with a combination of the therapies responded, suggesting an additive effect of the SLC-int:PD-L1 Nb and the EcN-SLC-hlyE (FIG. 5C). Lastly, since increased toxicity is observed when immunotherapeutics are used in combination, body weight of the mice was tracked throughout the trial and no significant changes in body weights between treatment groups were observed at the end of the trial (FIG. 5D).

Figure 5G:
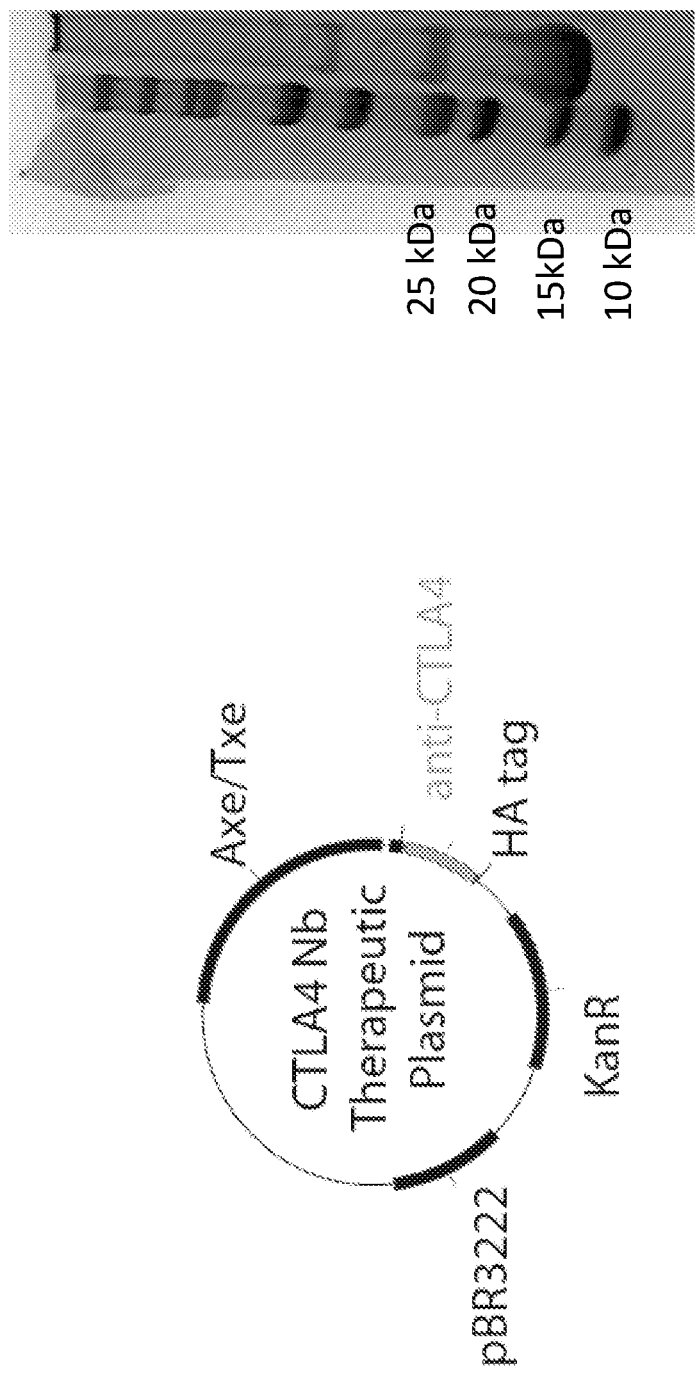
FIG. 5G shows a plasmid map of the CTLA4 Nb on a high copy plasmid and a gel showing the purification of the CTLA4 Nb.
Figure 5H:
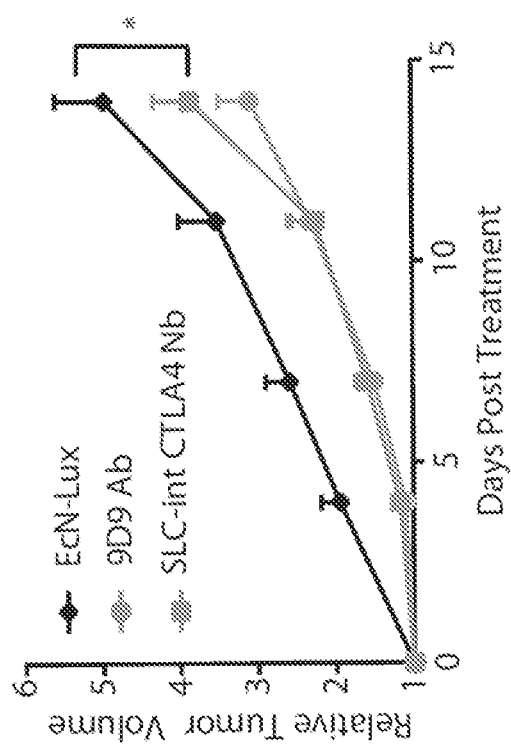
FIG. 5H is a graph of mean relative tumor trajectories of BALB/c mice implanted subcutaneously with 5×106 CT26 cells on both hind flanks. When tumors reached about 200 mm$^3$, mice received intratumoral injections every 3-4 days of either EcN-lux, SLC-int-CTLA4 Nb or intraperitoneal injections of a 9D9 mAb (100 ug/mouse).
Figure 5I:
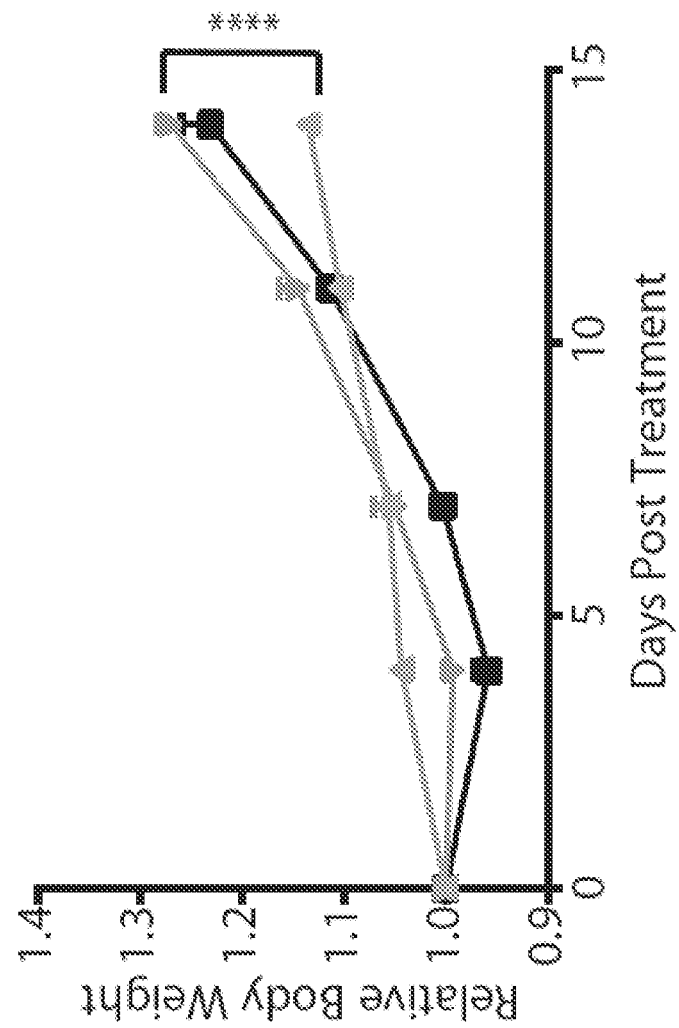
FIG. 5I is a graph of mean body weight of CT26 tumor bearing BALB/c mice treated with EcN-lux (dark lines with circles), SLC-int-CTLA4 Nb (light lines with square) or intraperitoneal injections of a 9D9 mAb (medium lines with circles).
Figure 5J:
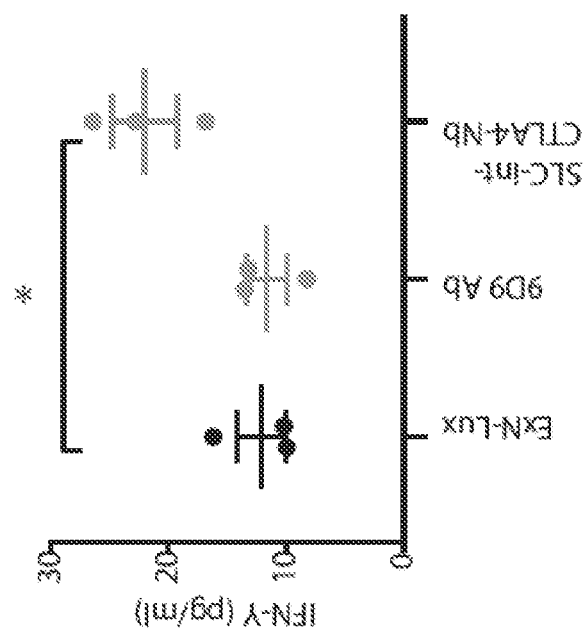
FIG. 5J shows a graph of interferon gamma cytokine levels of tumor lysates measured by Luminex Multiplex Assay of CT26 tumor bearing BALB/C mice treated with intratumoral injections of EcN-lux or SLC-int: CTLA-4nb or intraperitoneal injections of the 9D9 anti-CTLA-4mAb (200 ug/mouse) N=3 biological replicates per group, *$P=0.0224$, one-way ANOVA with Bonferroni post-test, error bars represent S.E.M.

Combination of the SLC:PD-L1 Nb and EcN-SLC-hlyE therapeutics suggested that the PD-L1 Nb therapeutic platform can be further maximized through combination therapy approaches. Clinically, anti-CTLA-4 mAbs are frequently used in combination with anti-PD-L1 mAbs. Therefore, to make the platform more generalizable as a checkpoint blockade nanobody treatment option, a microbial cocktail was engineered that could also block the interaction between CTLA4 and its associated ligands (Contardi et al. 2005). A Nb against CTLA-4 was obtained from the RCSB Protein Data Bank and its sequence was cloned onto the same plasmid vector used to express the PD-L1 Nb (FIG. 5G). BALB/c mice were implanted subcutaneously with $5 \times 10^6$ CT26 cells on both hind flanks. When tumors reached about 200 mm$^3$, mice received intratumoral injections every 3-4 days of either EcN-lux, SLC-int-CTLA4 Nb, SLC-int-PD-L1 Nb, or an equal parts cocktail of SLC-int-CTLA4 Nb and SLC-int-PD-L1 Nb strains. In the CT26 mouse model, the SLC-int:CTLA-4 Nb monotherapy was moderately efficacious and demonstrated similar efficacy to that of the anti-CTLA-4 mAb (FIG. 5H). While the therapeutic response for tumors treated with SLC-int:CTLA-4 Nb was only modest, significantly less toxicity was observed in these mice compared to the anti-CTLA-4 mAb group. Over the course of two weeks, the average weight of mice treated with the anti-CTLA-4 mAb had increased by about 10%, while the average weight of the SLC-int:CTLA-4 mice had increased by about 30% (FIG. 5I). In addition to fewer toxic effects, treatment with the SLC-int:CTLA-4 Nb induced the production of more IFNγ and IL-15 in the tumor microenvironment when compared to the anti-CTLA-4 mAb and the EcNlux control (FIG. 5J). An increase in pro-inflammatory cytokines suggested an increase in T cell infiltration and proliferation, thereby providing further rationale for combination of SLC-int-CTLA-4 Nb and SLC-int:PD-L1 Nb.

Figures 6, 6A:
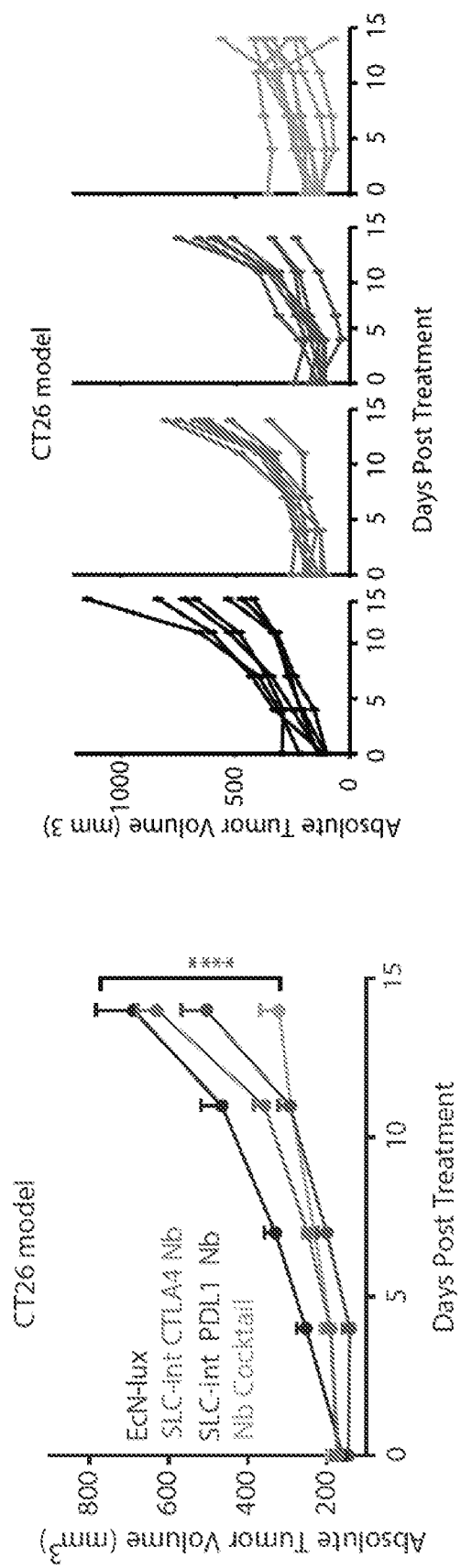
FIG. 6—Combination therapy of SLC-int:probiotics producing anti-PD-L1 or anti-CTLA-4 Nbs enhances therapeutic response characterized by a decrease in Treg cells and an increase in proliferative conventional CD4+ cells.
FIG. 6A shows mean absolute tumor trajectory (left panel) and individual trajectories (right panel) of mice (N=6-8 tumors per group, ** $P<0.0001$, two way-ANOVA with Bonferroni post-test, error bars represent S.E.M) where BALB/c mice were implanted subcutaneously with $5 \times 10^6$ CT26 cells on both hind flanks. When tumors reached approximately 200 mm$^3$, mice received intratumoral injections every 3-4 days of either EcN-lux, SLC-int:CTLA-4nb, SLC-int:PD-L1nb, or an equal parts Nb cocktail.
Figure 6B:
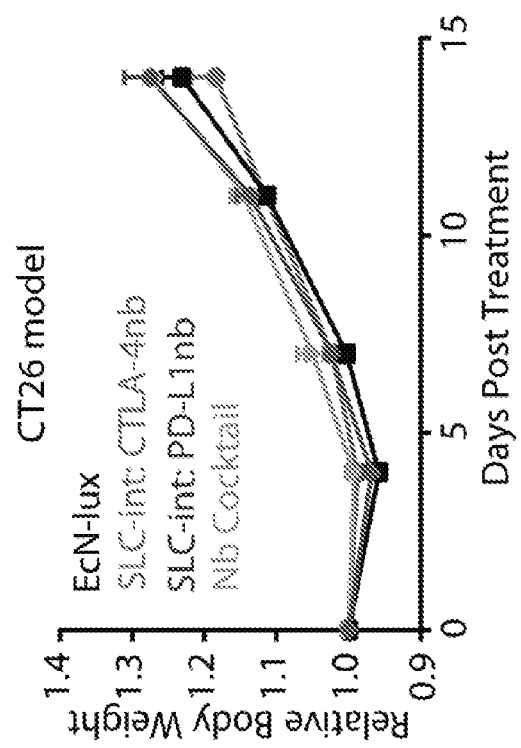
FIG. 6B is a graph showing mean relative body weight of CT26 tumor bearing BALB/c mice over time in each treatment group (error bars represent S.E.M).

Treatment with a combination of the checkpoint blockade nanobodies for PD-L1 and CTLA-4 significantly reduced the mean tumor volume compared to the monotherapies (FIG. 6A). The distribution of individual tumor volumes for each treatment group suggested that the average absolute volumes for mice treated with the combination therapy were smaller by the end of treatment (FIG. 6A). Similar to the EcN-SLC-hlyE combination trial, a partial response was calculated to quantify the therapeutic response of the combination therapy. About 2 weeks after treatment began, about 60% of the SLC-int:PD-L1 Nb treated tumors responded, about 20% of the SLC-int:CTLA-4 Nb treated tumors responded, and about 100% of the tumors treated with the nanobody cocktail responded (FIG. 6A). Furthermore, mouse body weight was tracked throughout the trial and no significant weight changes were observed (FIG. 6B).

Figure 6D:
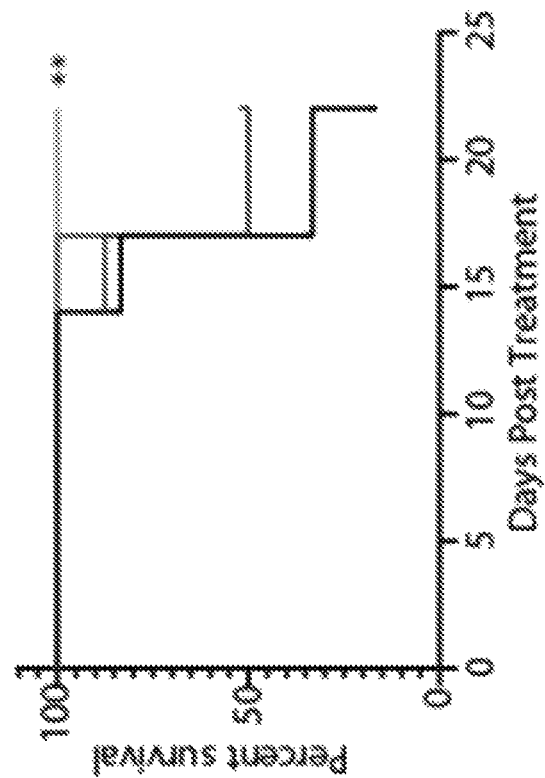
FIG. 6D is a survival curve of the treated mice. For FIGS. 6C and 6D,  P<0.0001, 2-way ANOVA, N=8-10 tumors per group.
Figure 6C:
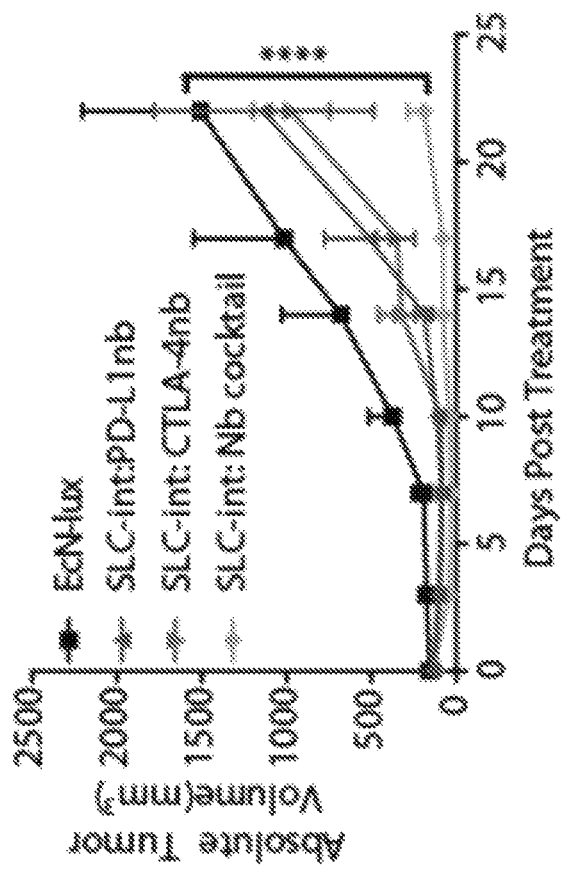
FIG. 6C shows a graph of absolute tumor volume in BALB/c mice implanted subcutaneously with $5 \times 10^6$ A20 cells on both hind flanks. When tumors reached approximately 150-200 mm³ A20 mice receiving intratumoral injections every 3-4 days of either EcN-lux, SLC-int: PD-L1nb, SLC-int:CTLA-4nb, or an equal parts cocktail combination (SLC-int: Nb cocktail) for about 3 weeks.

Experiments were repeated using an A20 mouse model. The first experiments done with the A20 mouse included treatment through 23 days. BALB/c mice were implanted subcutaneously with $5 \times 10^6$ A20 cells on both hind flanks. When tumors reached approximately 150-200 mm$^3$, mice received intratumoral injections every 3-4 days of either EcN-lux, SLC-int:PD-L1nb, SLC-int:CTLA-4nb, or an equal parts cocktail combination. Treatment with a combination of the checkpoint blockade nanobodies for PD-L1 and CTLA-4 significantly reduced the mean tumor volume compared to the monotherapies and greatly increased survival (FIGS. 6C, 6D).

Figure 6E:
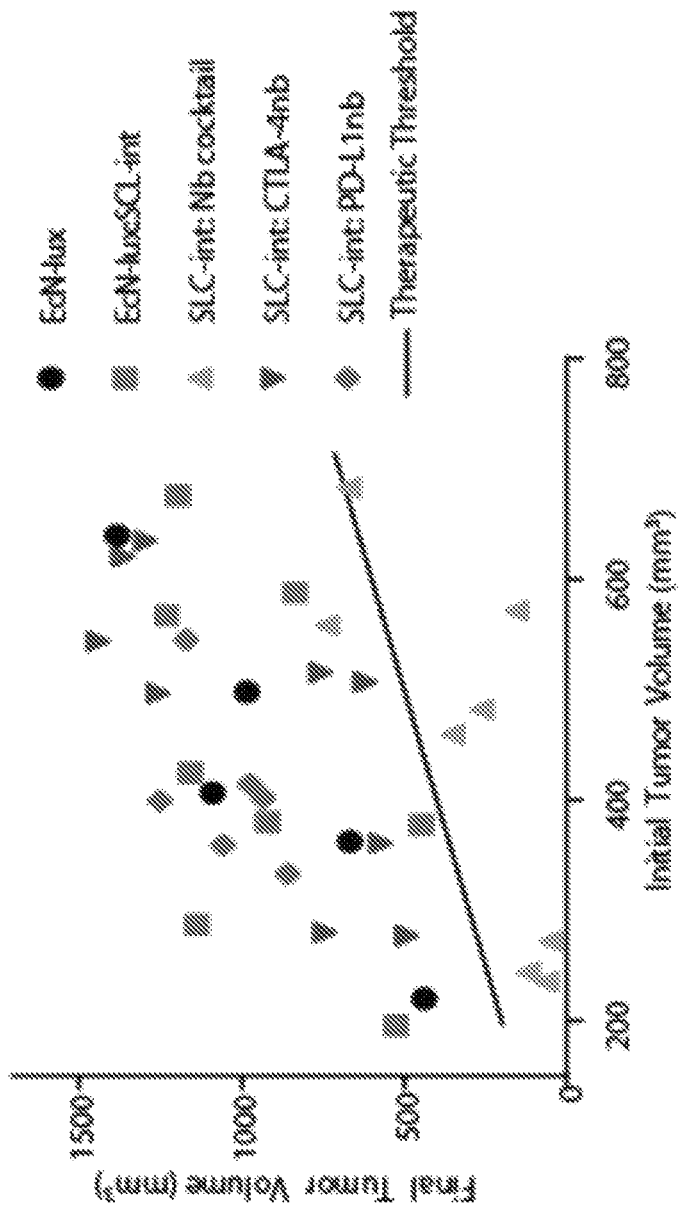
FIG. 6E shows that treatment with the bacteria-produced checkpoint nanobody combination can shrink large tumors. BALB/c mice were implanted subcutaneously with $5 \times 10^6$ A20 cells on both hind flanks. When tumors reached approximately 200-700 mm³, mice received intratumoral injections every 3-4 days of either EcN-lux, EcN-lux:SLC-int, SLC-int:PD-L1nb, SLC-int:CTLA-4nb, or an equal parts SLC-int:Nb cocktail combination. The scatter plot shows each tumor's final volume plotted against its initial tumor volume. A y=x line is drawn (black) as a therapeutic threshold where points below the line indicate tumor regression and above the line indicates tumor growth.

Additionally, the combination treatment was used to treat large tumors in the A20 mice. BALB/c mice were implanted subcutaneously with $5\times10^6$ A20 cells on both hind flanks. When tumors reached approximately 200-700 mm³, mice received intratumoral injections every 3-4 days of either EcN-lux, EcN-lux:SLC-int, SLC-int:PD-L1nb, SLC-int:CTLA-4nb, or an equal parts SLC-int:Nb cocktail combination. Treatment with a combination of the checkpoint blockade nanobodies for PD-L1 and CTLA-4 significantly reduced the initial tumor volume compared to the monotherapies (FIG. 6E).

Figure 6F:
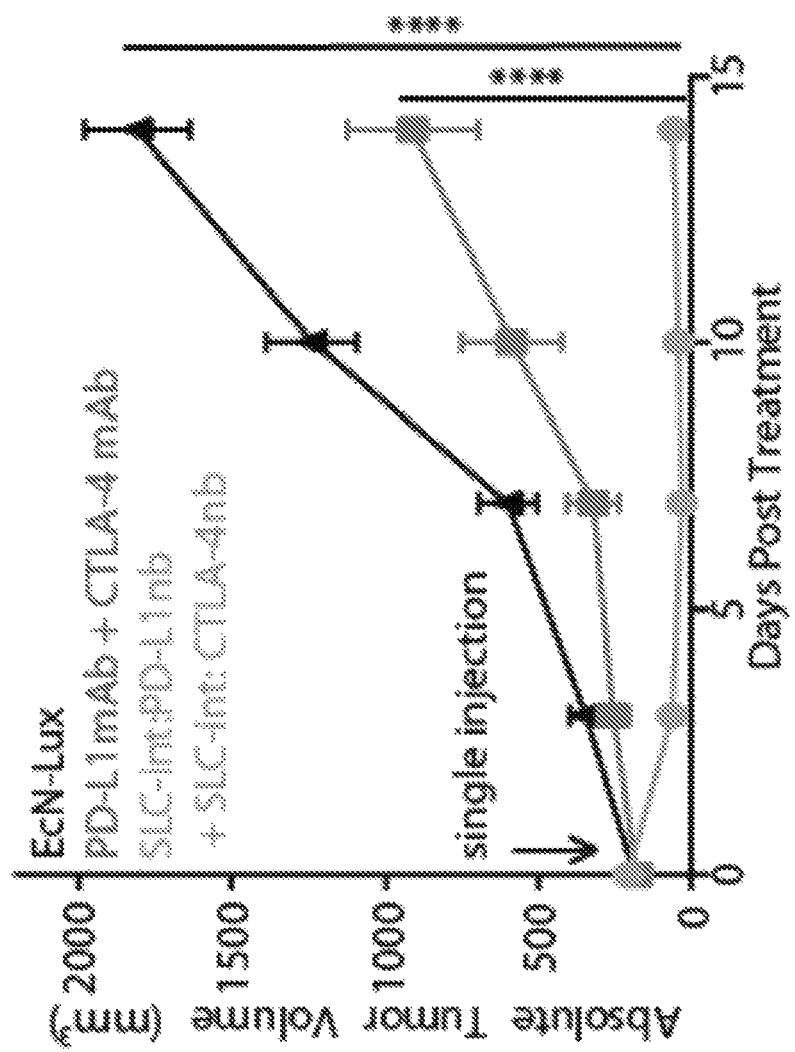
FIG. 6F is a graph of absolute tumor volume of A20 mice receiving one intratumoral injection of either EcN-lux or a combination of SLC-int:PD-L1nb+SLC-int:CTLA-4nb or one intraperitoneal injection of 200 ug/mouse anti-CTLA-4 mAb+100 ug/mouse anti-PD-L1 mAb. Plot shows mean absolute tumor trajectory of tumors (N=8-10 tumors per group, 2-way ANOVA, ** P<0.0001).

In further studies, BALB/c mice were implanted subcutaneously with $5\times10^6$ A20 cells on both hind flanks. When tumors reached approximately 150-200 mm³, mice received one intratumoral injection of either EcN-lux or a combination of SLC-int:PD-L1nb+SLC-int:CTLA-4nb or one intraperitoneal injection of 100 ug/mouse anti-CTLA-4 mAb+ 200 ug/mouse anti-PD-L1 mAb. A sustained response and tumor clearance was observed only for mice treated with the combination of bacterially-produced Nbs (SLC-int:PD-L1nb+SLC-int:CTLA-4nb) (FIG. 6F). Mice treated with a single injection of the combination of SLC-int-CTLA-4 Nb and SLC-int:PD-L1 Nb had lower systemic inflammation as measured by TNF-α levels in their serum than mice treated with a PDL1-mAb+CTLA-4 mAb (FIG. 6G).

Figure 6H:
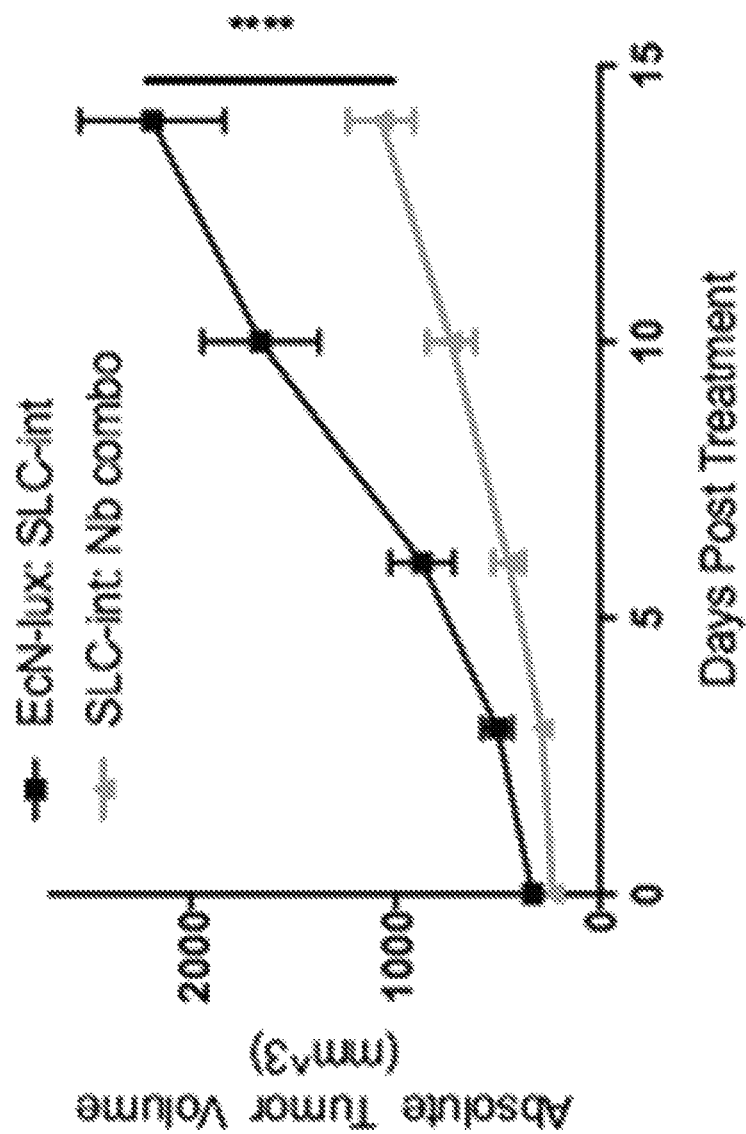
FIG. 6H is a graph of absolute tumor volume in BALB/c mice implanted subcutaneously with $5 \times 10^6$ A20 cells on both hind flanks. When tumors reached approximately 150-200 mm³, mice received one intravenous injection of SLC-int: PD-L1nb+SLC-int:CTLA-4nb or EcN-lux. Plot shows mean absolute tumor trajectory. (N=10-15 tumors per group, 2-way ANOVA, ** P<0.0001, error bars represent SEM).
Figure 6J:
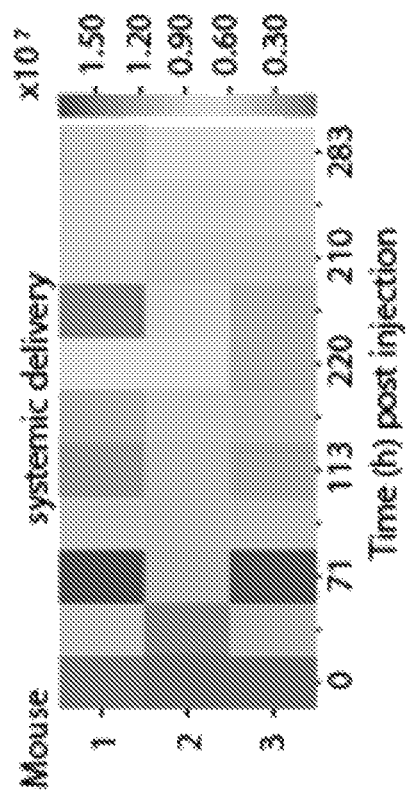
FIG. 6J is a heatmap showing total flux (in Radiance p/sec/cm2/sr) of the bacteria populations over time quantified from IVIS images in FIG. 6I.
Figure 6I:
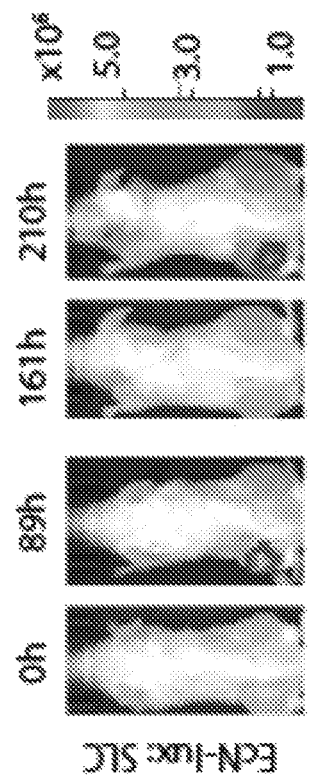
FIG. 6I are representative IVIS images from the mice receiving the one intravenous injection of SLC-int:PD-L1nb+SLC-int:CTLA-4nb.
Figure 6K:
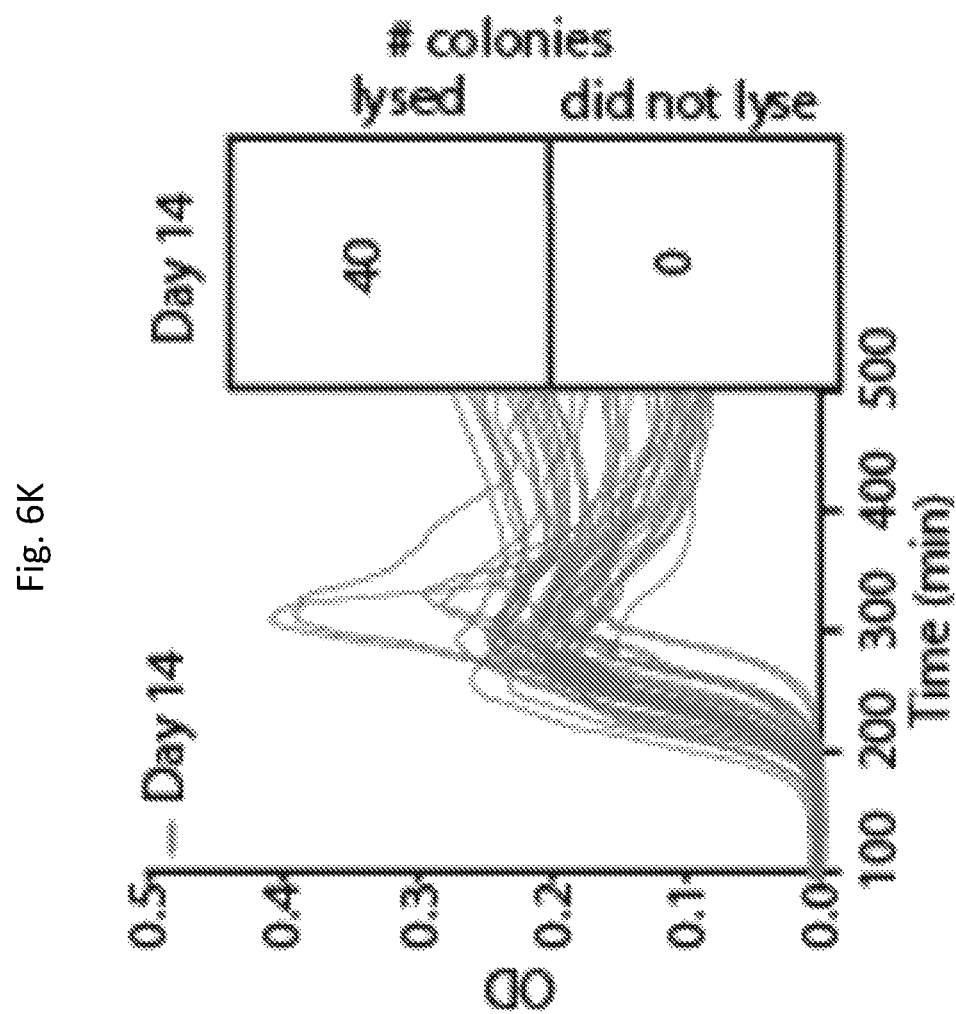
FIG. 6K is a plot of the plate reader experiment showing the oscillations of colonies plated from tumors harvested on day 14 and a grid showing the number of successful lysis events.
Figure 6L:
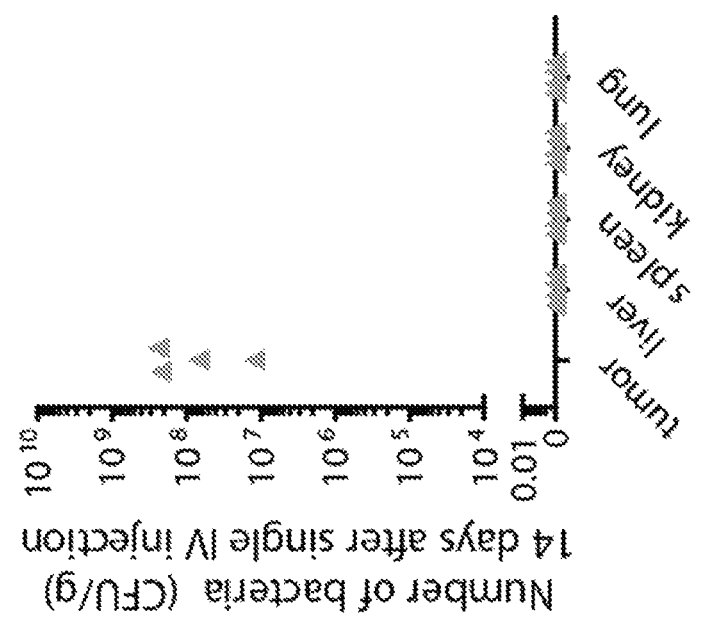
FIG. 6L are the number of bacteria in tumors, livers, kidneys, lungs, and spleens harvested from A20-bearing mice 14 days after one intravenous injection of SLC-int: PD-L1nb+SLC-int:CTLA-4nb or EcN-lux. The CFU/g was calculated for organs harvested from SLCint: PD-L1nb+SLC-int:CTLA-4nb treated mice.

In yet a further study using the A20 mice, it was shown that a single intravenous injection of the programmable bacteria resulted in a sustained therapeutic response. In these studies, BALB/c mice were implanted subcutaneously with $5\times10^6$ A20 cells on both hind flanks. When tumors reached approximately 150-200 mm³, mice received one intravenous injection of SLC-int:PD-L1nb+SLC-int:CTLA-4nb. The one injection resulted in reduced tumor volume for 15 days (FIG. 6H). Moreover, using IVIS, it was shown that a single intravenous dosage of the programmable bacteria produced the nanobodies in robust oscillations in vivo (FIGS. 6I-6K). Biodistribution showed that the bacteria were not measured at detectable levels in peripheral organs like the liver and spleen, and instead remain localized at the tumor site, suggesting that the nanobody will not be released elsewhere (FIG. 6L).

Figure 6M:
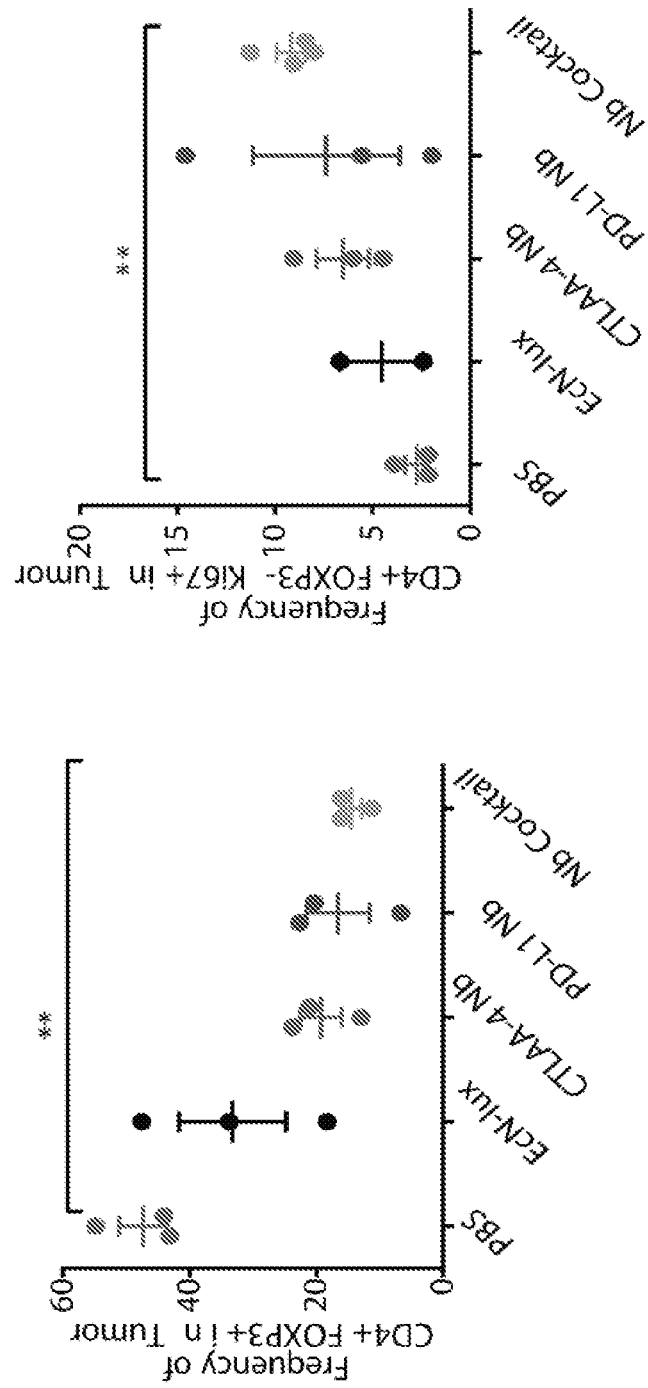
FIG. 6M are flow cytometry graphs depicting frequencies of CD4+FOXP3+ regulatory T cells (left panel) (N=3, unpaired t test between PBS and Nb cocktail,  P=0.0013) and (right panel) proliferating CD4+FOXP3-Ki67+ conventional T cells (N=2-3, unpaired t test between PBS and Nb cocktail,  P=0.0013) of A20-bearing BALB/C mice where tumor-infiltrating lymphocytes were isolated on day 8 after initial intratumoral treatment with PBS, EcN-lux, SLC-int:PD-L1nb, SLC-int:CTLA-4nb or an equal parts cocktail combination of SLC-int:PD-L1nb and SLC-int-CTLA-4nb.
Figure 6N:
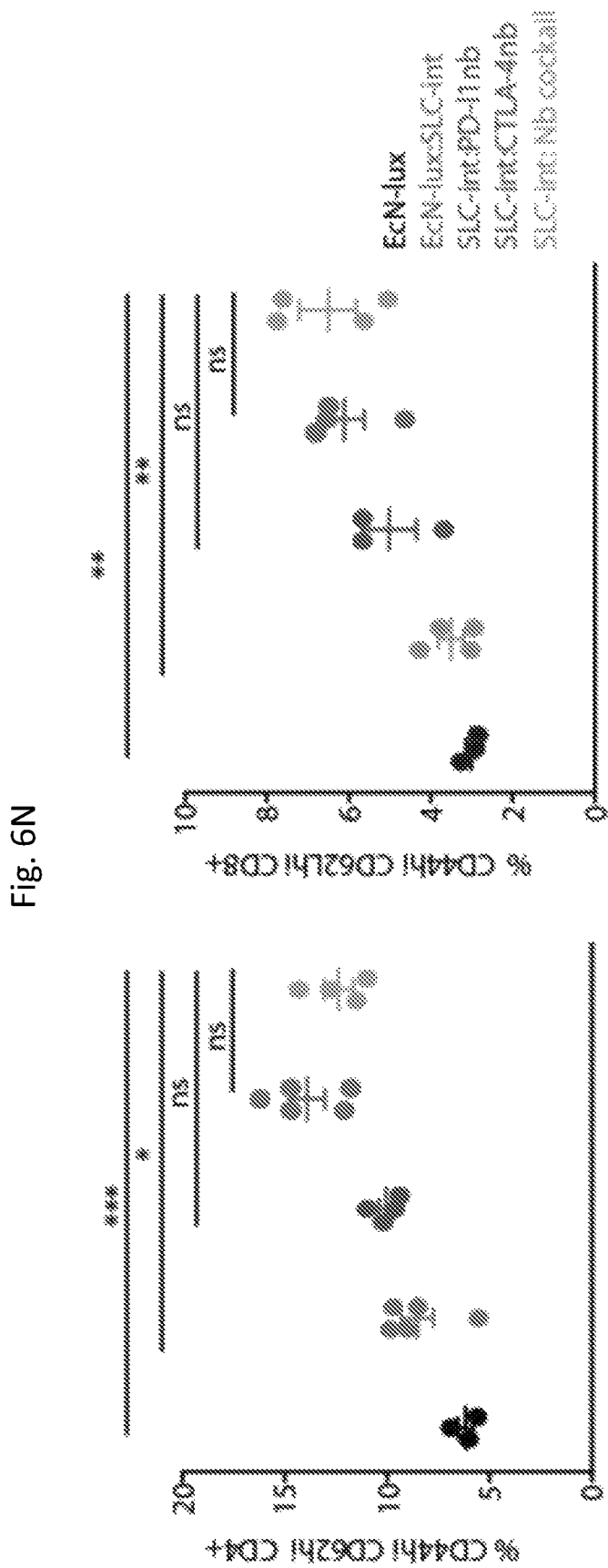
FIG. 6N shows graphs of CD4+ cells and CD8+ cells in BALB/c mice implanted subcutaneously with $5 \times 10^6$ A20 cells on both hind flanks. When tumors reached approximately 200 mm³, mice received intratumoral injections every 3-4 days of either EcN-lux, EcN-lux:SLC-int, SLC-int:PD-L1nb, SLC-int:CTLA-4nb, or an equal parts SLC-int:Nb cocktail combination. Spleenocytes were isolated on day 8 after initial treatment and analyzed by flow cytometry for frequencies of CD44hi CD62Lhi central memory CD4+ cells and CD8+ T cells (* P<0.001, ** P<0.01, *P<0.05, Ordinary 1-way ANOVA, N=3-5 per group).

Further in depth immunophenotyping of splenic and tumor-infiltrating lymphocytes in the A20 model was performed to assess the induction of systemic antitumor immunity. FIG. 6N shows an increased frequency of CD4– and CD8+ memory T cell populations in the spleen, suggesting the establishment of central memory in mice treated with a combination of the bacterially-produced checkpoint Nbs. These data suggested enhanced tumor-specific T cell responses, which could mediate protection in a rechallenge scenario. Additionally, as shown in FIG. 6O, increased frequencies of tumor-infiltrating IFNg+CD4+, IFNg+CD8+ cells, and double positive IFNg+TNFα+CD8+ cells were observed cells following ex vivo stimulation, suggesting enhanced activation of cytotoxic CD8+ and conventional CD4+ cells at the tumor site. Also there was a decrease in the population of regulatory T cells (Tregs, CD4+FOXP3+) in tumors treated with the Nb cocktail (FIG. 6M). Furthermore, there was an increase in the proliferation of conventional CD4+ cells (CD4+FOXP3-Ki67+) in the Nb cocktail-treated tumors, suggesting that the shift in favor of responsive T cells and decrease in immunosuppressive Tregs may result in a more robust immune response and mediate the therapeutic effect observed (FIG. 6M).

These data showed that the administration of the programmable bacteria activated both the local immunity in the tumor as well as systemic immunity.

Example 7—Bacteria Containing CD47 Nanobody as the Deliverable Therapeutic Agent—Materials and Methods for Examples 8-11

Strains and Plasmids

Plasmids were constructed using Gibson assembly or standard restriction enzyme-mediated cloning methods. The pSC01 SLC plasmid was constructed by first amplifying a region containing the constitutively expressed luxR gene and phage lysis gene, φx174E under the control of luxI promoter from a pZA35E plasmid (Din et al. 2016). Next, this was cloned into a pTD103-luxI plasmid (Danino et al. 2010) using the AvrII site. The pSC02 therapeutic plasmid was constructed by cloning a gBlock (IDT) encoding a tac promoter and an *E. coli* codon-optimized sequence for the A4 anti-CD47 nanobody (Sockolosky et al. 2016) with an C-terminal hemagglutinin tag into the multiple cloning site of a pAH162 plasmid (Haldimann and Wanner 2001). Additionally, two stabilizing elements, the hok/sok system (Gerdes et al. 1986) and alp7 partitioning system (Derman et al. 2012) were introduced into pSC02 to minimize plasmid loss in vivo. pSC01 and pSC02 were transformed into chemically competent *E. coli* Pir1⁺ (Invitrogen). eSLC strains were grown in LB media with 50 µg/mL kanamycin (pSC01) and 100 µg/mL tetracycline (pSC02) along with 0.2% glucose at 37° C. for under 12 hours in a shaking incubator. Glucose was added to reduce expression from the Lux promoter and prevent lysis in vitro. The pSC04 protein expression plasmid was constructed by cloning a gBlock (IDT) encoding an *E. coli* codon-optimized sequence for the A4 anti-CD47 nanobody (Sockolosky et al. 2016) with a C-terminal 6x-Histidine tag into the multiple cloning site of an IPTG inducible pET vector under ampicillin resistance (100 µg/mL). pSC04 was transformed into NiCo21(DE3) *E. coli* (NEB).

Synchronized Lysis Circuit (SLC) Characterization

To validate SLC function, SLC⁺ and SLC⁻ *E. coli* were inoculated into LB media containing appropriate antibiotics and diluted 1:10. Samples were grown at 37° C. in a round bottom 96 well plate in a shaking Tecan plate reader. $OD_{600}$ was recorded every 10 minutes for 20 hours. Agar pads were prepared according to previous protocols (Skinner et al. 2013). SLC⁺ and SLC⁻ *E. coli* were inoculated into LB media containing appropriate antibiotics and grown to mid-log phase. They were diluted 1:100 and grown under agar pads at 37° C. and imaged using a Nikon Ti-E microscope equipped with an Okolab stage top incubator.

Bacterial Nanobody Characterization

For purification of programmable CD47nb (rCD47nb), pSC04 containing NiCo21(DE3) *E. coli* were grown at 37° C. to approximately 0.8 $OD_{600}$ and induced with 1 mM IPTG for 20 hours at 30° C. Cells were centrifuged at 4000 rpm for 10 minutes. After resuspension in lysis buffer (50 mM $NaH_2PO_4$, 300 mM NaCl, pH 8.0) and sonication, lysates were spun at 10000 rpm for 30 minutes at 4° C. The supernatant was loaded on to Ni-NTA (Qiagen) resin and washed in wash buffer (35 mM imidazole) followed by elution in 250 mM imidazole. The elutions were then dialyzed in PBS using regenerated cellulose dialysis tubing (3500 Da MWCO), and the solution was filtered through a 0.2 µm filter to remove any residual debris and stored at −80° C.

Overnight cultures of *E. coli* containing pSC01 and pSC02 were grown in appropriate antibiotics and 0.2% glucose. A 1:100 dilution into LB with antibiotics was made the following day and bacteria were grown in a shaking incubator at 37° C. Optical Density (OD) was measured every 30 minutes until the OD of lysing strains began to fall, indicating lysis. At this point OD normalized bacteria were spun down at 3000 rcf and supernatants were filtered through a 0.2 μm filter. Cell pellets were mechanically lysed by 3-4 freeze-thaw cycles. Supernatants and lysates were separated by SDS-PAGE followed by immunoblotting with rat anti-HA (Sigma) antibody to evaluate the presence of programmable CD47nb (rCD47nb) protein in culture fractions. To verify binding of bacterially produced nanobody to CD47 on tumor cells, serial dilutions of bacterial supernatants from SLC bacteria with or without pSC02 or rCD47nb were co-incubated with FITC-labeled anti-CD47 antibody in the presence of A20 tumor cells for 1 hour and FITC fluorescence was measured by flow cytometry.

In Vitro Phagocytosis

Overnight cultures of *E. coli* containing pSC01 and pSC02 were grown in appropriate antibiotics and 0.2% glucose. A 1:100 dilution into LB with antibiotics was made the following day and bacteria were grown to mid-log phase in a shaking incubator at 37° C. Bacteria were pelleted at 3000 rcf and lysed by sonication. To obtain eSLC and eSLC-CD47nb lysates, sonicates were spun at 10000 rpm for 5 minutes and supernatants were filtered through a 0.2 μm filter to remove any residual debris. Harvested bone marrow-derived macrophages (BMDMs) were detached and seeded on to a transparent 96-well tissue culture plate at $5 \times 10^4$ cells per well. A20 tumor cells were incubated for 10 minutes with 5 μM Vybrant DiI solution (Invitrogen). Labeled A20 cells were pre-treated with serial dilutions of bacterial lysates (eSLC or eSLC-CD47nb) or with anti-CD47 mAb, isotype or PBS. Following 3.5 hour coincubation of labeled, pre-treated A20 cells and BMDMs, residual A20 cells were washed and BMDMs were stained with NucBlue. Multiple random fields were imaged for each replicate using a Nikon Ti-E microscope. The ratio of $DiI^+$ BMDMs to total $NucBlue^+$ BMDMs was counted for each field to score phagocytosis.

Animal Models

All animal experiments were approved by the Institutional Animal Care and Use Committee. The protocol requires animals to be euthanized when tumor burden reaches 2 cm in diameter or under veterinary staff recommendation. Mice were blindly randomized into various groups. Animal experiments were performed on 4-8 week-old female BALB/c mice or C57BL/6 (Taconic Biosciences) with bilateral subcutaneous hind flank tumors from A20 murine lymphoma cells (ATCC), 4T1-luciferase mammary carcinoma cells (ATCC, luciferized by stable plasmid transfection), or B16-F10 melanoma cells. Unless otherwise specified, cells were injected subcutaneously at a volume of 100 μl per flank, with each implant consisting of $5 \times 10^6$ cells (BALB/c, A20), $10^6$ cells (BALBc, 4T1), or $5 \times 10^5$ (C57BL/6, B16-F10). Tumors were grown to an average volume of approximately 100-200 mm³ before treatment with bacterial strains. Tumor volume was calculated by measuring the length and width of each tumor using calipers, where V=length×width²×0.5 as previously calculated (Lin et al. 2015). The growth in mm/day was computed by taking the difference between tumor volumes at adjacent time points for a particular animal. Values were computed as the mean with standard error plotted.

Bacterial Administration for In Vivo Experiments

Bacterial strains were grown overnight in LB media containing appropriate antibiotics and 0.2% glucose. A 1:100 dilution into media with antibiotics was started the day of injection and grown to an $OD_{600}$ of approximately 0.1. Bacteria were spun down and washed 3 times with sterile PBS before injection into mice. Intratumoral injections of bacteria were performed at a concentration of $5 \times 10^8$ CFU per ml in PBS with a total volume of 20-40 μl injected per tumor.

Biodistribution and In Vivo Bacterial Dynamics

Following treatment with $10^7$ $SLC^+$ *E. coli*, tumors, spleen and liver were weighed and homogenized using a gentle MACS tissue dissociator (Miltenyi Biotec) (C-tubes). Homogenates were serially diluted and plated on LB-agar plates at 37° C. overnight. Colonies were counted (limit-of-detection $10^3$ CFU/g) and computed as CFU/g of tissue. To determine in vivo dynamics of SLC and $SLC^+$ *E. coli*, $10^7$ SLC or $SLC^-$ *E. coli* Nislux (genomic expression of luxCDABE cassette) were injected unilaterally into hind-flank tumors. Luminescent signal was measured at multiple timepoints over 4 days with an In vivo imaging system (IVIS) following bacterial injection to follow dynamics Flow Cytometry Tumors were extracted for immunophenotyping on day 3 or day 8 following commencement of bacterial therapy. Myeloid and lymphoid subsets were isolated from tumor tissue by mechanical homogenization of tumor tissue followed and digestion with collagenase A (1 mg/ml; Roche) and DNase I (0.5 μg/ml; Roche) in isolation buffer (RPMI 1640 supplemented with 5% FBS, 1% 1-glutamine, 1% pen-strep and 10 mM Hepes) for 1 hour at 37° C. Cells were filtered through 100 μm cell strainers, washed in isolation buffer and stained. Dead cells were excluded by staining with Ghost Dye cell viability reagent. Extracellular antibodies used included anti-B220 (BD), anti-CD4 (Tonbo), anti-CD8 (eBioscience) anti-NKp46 (BD), anti-Gr-1 (Tonbo) anti-CD11b (BD), anti-F4/80 (eBioscience) anti-SIRPα (BioLegend) and anti-MHC Class II (Tonbo). To measure T cell production of cytokines, cells were stimulated for 2 hours with PMA (50 ng/ml Sigma), and ionomycin (1 nM; Calbiochem) in the presence of GolgiPlug (brefeldin A). Following extracellular staining with the aforementioned antibodies, intracellular staining was performed using anti-CD3 (Tonbo), anti-TCRβ (BD), anti-CTLA4 (eBioscience), anti-Foxp3 (eBioscience), anti-Ki-67 (Thermo), anti-Granzyme-B (Biolegend) and cytokines (anti-IL-17 (eBioscience), anti-TNF-α (eBioscience), and anti-IFN-γ (Tonbo). Cells were fixed using Foxp3/transcription factor staining buffer set (Tonbo) as per manufacturer's protocol. Samples were analyzed using a BD LSRFortessa cell analyzer.

Statistical Analysis

Statistical tests were calculated in GraphPad Prism 7.0 (Student's t-test and ANOVA). The details of the statistical tests carried out are indicated in the respective figure legends. Where data were approximately normally distributed, values were compared using either a Student's t-test or one-way ANOVA for single variable, or a two-way ANOVA for two variables with Tukey's correction for multiple comparisons. For Kaplan-Meier survival experiments, a Log-rank (Mantel-Cox) test was performed. Mice were randomized in different groups before experiments.

Figures 7, 7A:
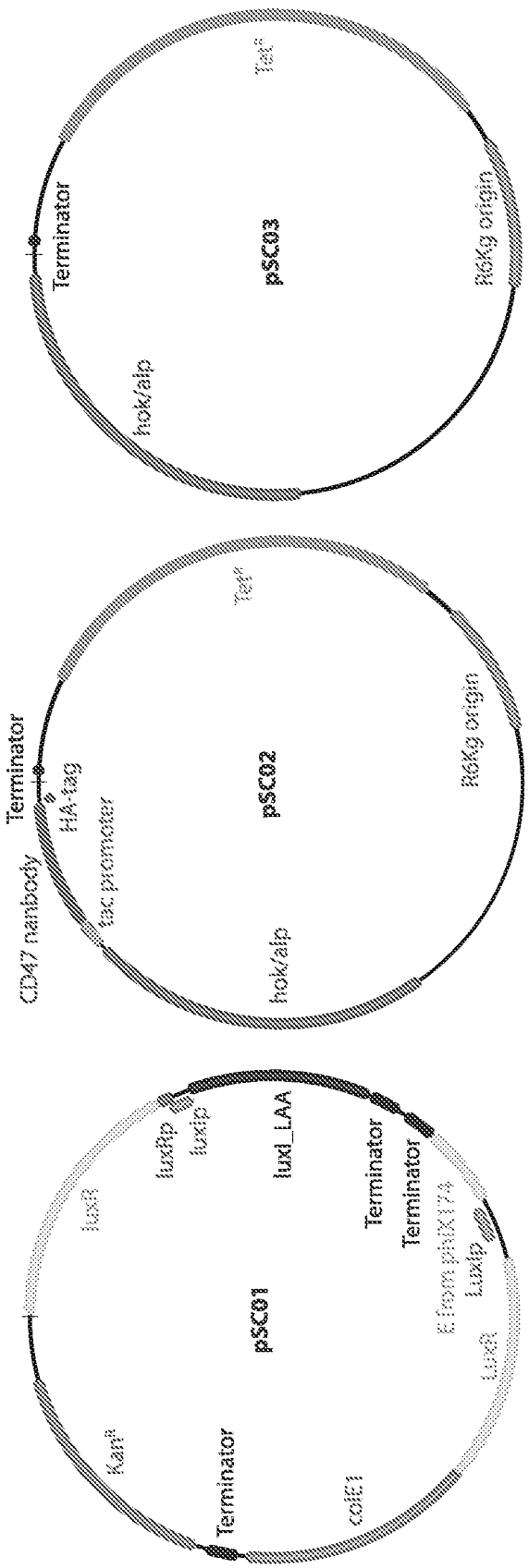
FIG. 7—Design of a cancer therapy system for release of a functional anti-CD47 blocking nanobody (nb) by programmable bacteria encoding a synchronized lysis circuit (SLC).
FIG. 7A is a map of the plasmids: pSC01, single plasmid synchronized lysis circuit; pSC02, stabilized plasmid driving constitutive expression of HA-tagged anti-CD47 nanobody; and pSC03 empty vector control.
Figure 7D:
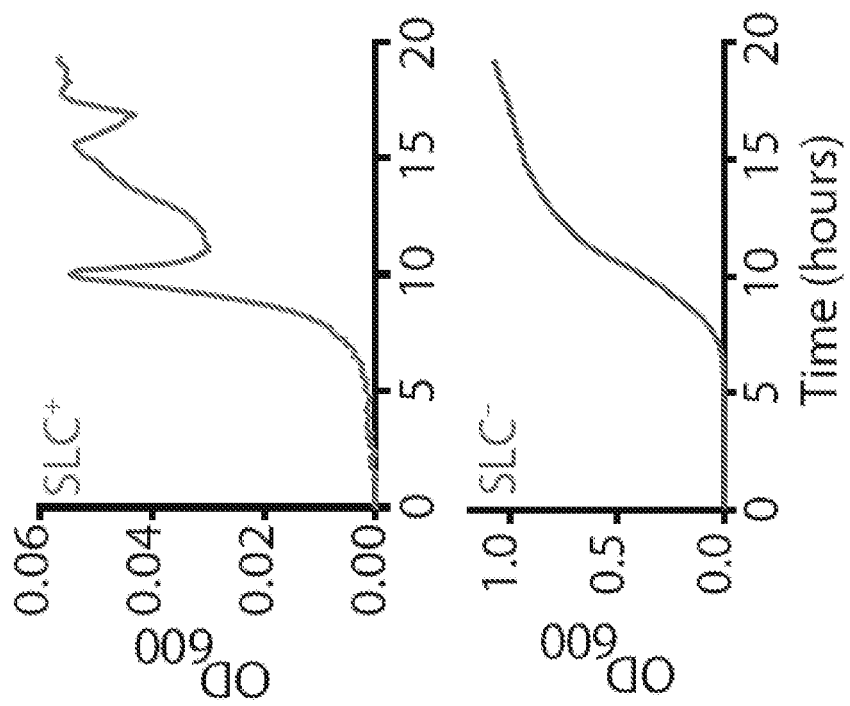
FIG. 7D are graphs of bacterial growth dynamics over time of SLC+ and SLC− *E. coli* in batch liquid culture.
Figure 7C:
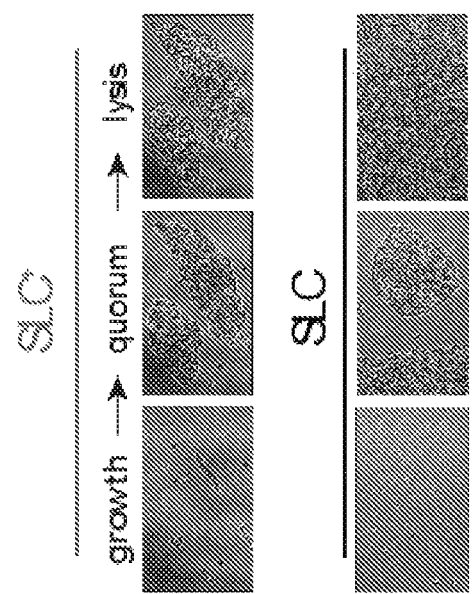
FIG. 7C are images of the bacterial growth dynamics of SLC+ and SLC− *E. coli* over time in agar-pad microscope experiments.
Figure 7E:
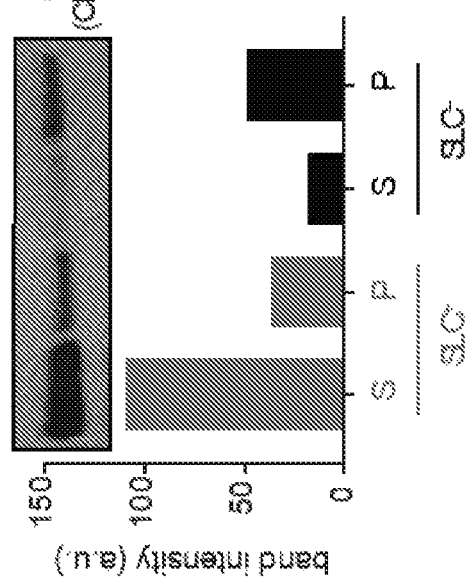
FIG. 7E is an immunoblot (upper panel) and graph (lower panel) of quantitation of bacterial culture supernatants (S) and cell pellets (P) in strains with and without SLC designed to constitutively produce HA-tagged CD47 nanobody.

Example 8—In Vitro Confirmation of Expression and Lysis-Dependent Release of CD47nb from the eSLC-CD47nb Bacteria To confirm expression and lysis-dependent release of CD47nb, a non-pathogenic *E. coli* was transformed with a single plasmid encoding the synchronized lysis circuit (eSLC), as well as a stabilized plasmid driving constitutive expression of a hemagglutinin (HA)-tagged variant of CD47nb (FIG. 7A). The SLC strain grows and produces the quorum-sensing molecule acylhomoserine lactone (AHL) via expression of luxI, then lyses at a critical threshold due to the production of a bacteriophage lysis protein (θ×174E), resulting in bacterial death and therapeutic release (FIG. 7B). Since this gene circuit was previously tested using two plasmids of differing copy numbers (Din et al. 2016), an SLC-mediated lysis of eSLC-CD47nb E. coli was assessed by time-lapse microscopy of bacteria using an agar pad (Skinner et al. 2013). eSLC-CD47nb grew, reached quorum and lysed over a 20-hour time course, in contrast to non-SLC E. coli (SLC$^-$) which continuously grew and filled the field of view (FIG. 7C). SLC$^+$ and SLC$^-$ E. coli was cultured in LB broth in a 96-well plate and optical density ($OD_{600}$) measured over time. eSLC-CD47nb (SLC$^+$) exhibited multiple periodic dips in $OD_{600}$, indicating rounds of synchronized lysis, whereas SLC$^-$ E. coli exhibited normal bacterial growth kinetics (FIG. 7D). Upon verifying synchronized lysis behavior, the lysis-mediated release of CD47nb in batch cultures was evaluated Immunoblots of log-phase bacterial cultures indicated that eSLC-CD47nb bacteria released significantly higher levels of HA-tagged CD47nb into culture supernatants than control CD47nb-HA bacteria without SLC (FIG. 7E), indicating that CD47nb release was enhanced by eSLC.

Figure 7F:
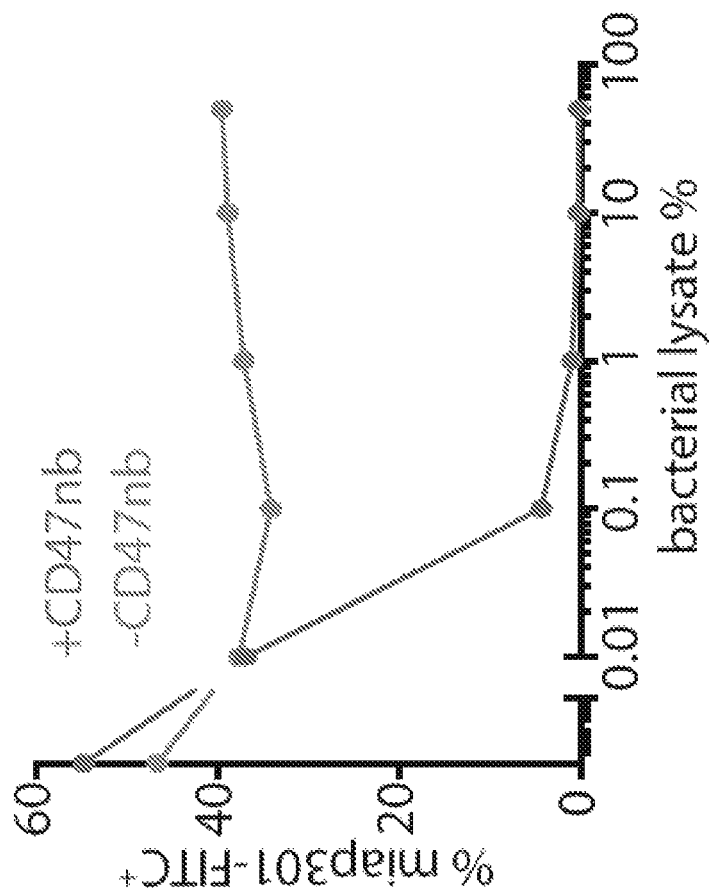
FIG. 7F is a graph of A20 cells co-incubated with constant concentration of FITC conjugated CD47 monoclonal antibody (FITC-miap301) along with varying concentrations of bacterial lysates containing constitutively expressed CD47nb (+CD47 nb, pSC02) or empty vector (−CD47 nb, pSC03).
Figure 7H:
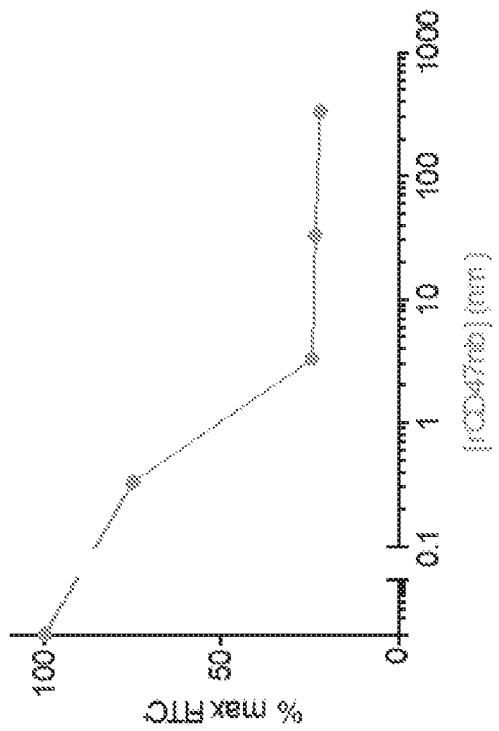
FIG. 7H shows a graph of A20 cells co-incubated with a fixed concentration of FITC-conjugated anti-CD47 (miap301) antibody along with serial dilutions of programmable 6×His-tagged CD47nb (rCD47nb).
Figure 7G:
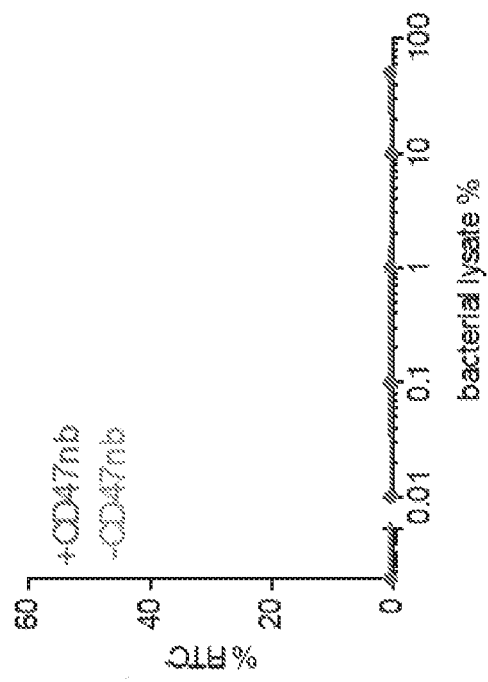
FIG. 7G is a graph of A20 cells co-incubated with a fixed concentration of FITC conjugated IgG2a-FITC isotype control along with varying concentrations of bacterial lysates containing constitutively expressed CD47nb or empty vector.

To verify that bacterially-produced nanobody functionally binds CD47, A20 murine lymphoma cells, known to express CD47 (Liu et al. 2015), were incubated with a fixed concentration of FITC-labeled anti-mouse CD47 mAb (clone miap301) and varying dilutions of bacterial lysate from eSLC-CD47nb or eSLC expressing an empty vector (FIG. 7F, FIG. 7G). A progressive reduction in CD47 staining was observed when cells were incubated with lysates from bacteria expressing CD47nb, suggesting that bacterially produced CD47nb effectively outcompeted miap301 binding to CD47 on the surface of A20 cells. Additionally, a C-terminal 6x-His tagged variant of CD47nb was cloned and purified programmable CD47nb (rCD47nb) by Nickel-affinity chromatography. Similarly, a progressive reduction in FITC fluorescence was observed when A20 cells were co-incubated with increasing concentrations of rCD47nb and a fixed concentration of FITC-labeled miap301 (FIG. 7H).

Figure 7J:
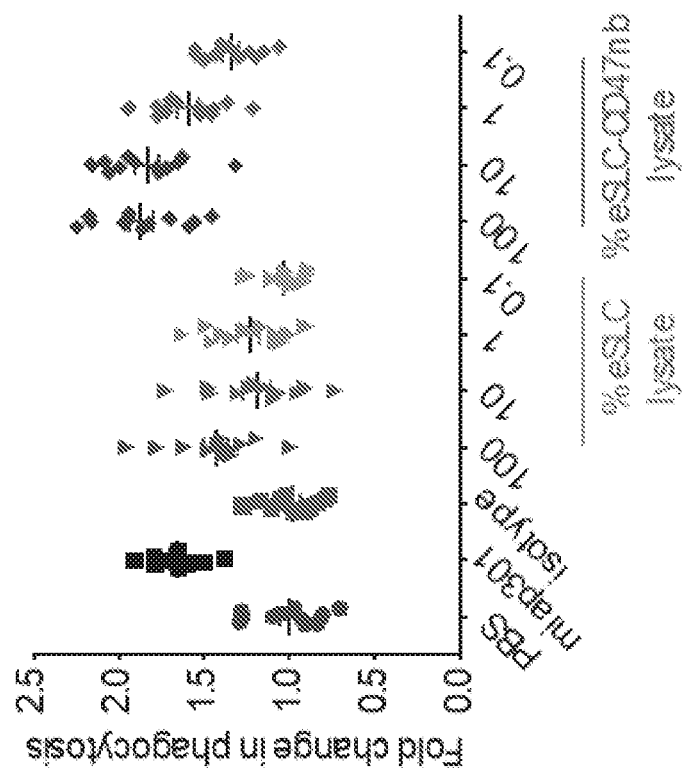
FIG. 7J is a scatter plot showing in vitro phagocytosis of DiI labeled A20 cells pretreated with PBS, miap301, IgG2a isotype control, or serial dilutions of eSLC or eSLC-CD47nb lysate in PBS by bone-marrow derived macrophages (n=4 fields of view×3 replicates, * P<0.001, one-way ANOVA with Bonferroni's multiple comparisons test).
Figure 7I:
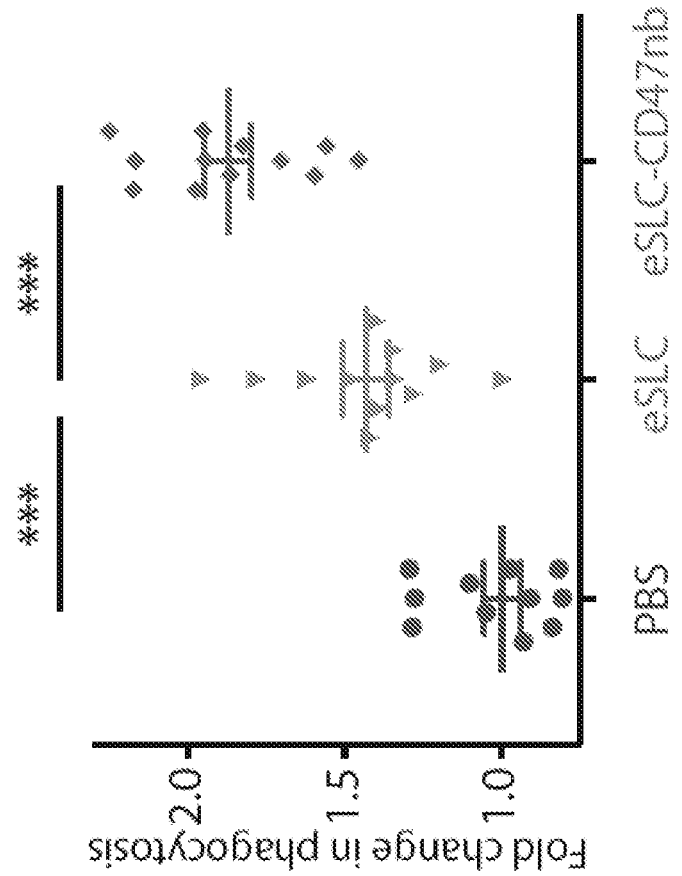
FIG. 7I is a scatter plot showing in vitro phagocytosis of DiI labeled A20 cells pretreated with PBS, SLC+bacteria lysate or SLC+CD47nb+bacteria lysate by bone-marrow derived macrophages (n=4 fields of view×3 replicates, * P<0.001, one-way ANOVA with Bonferroni's multiple comparisons test).

The ability of eSLC-CD47nb to induce A20 tumor cell phagocytosis by bone marrow-derived macrophages (BMDMs) was also evaluated (FIG. 7I, FIG. 7J). As expected, treatment with anti-CD47 mAb resulted in a 60% increase in phagocytosis (FIG. 7J) and treatment with eSLC lysate alone led to an increase in phagocytosis of tumor cells by 50%. Notably, eSLC-CD47nb treatment led to a 90% increase in phagocytosis compared to baseline, indicating that eSLC-CD47nb enhances phagocytosis of tumor cells by macrophages in a combinatorial, dose-dependent manner—via CD47 blockade and TLR agonism due to bacterial lysis adjuvants (FIG. 7I, FIG. 7J).

Overall, these results indicated that eSLC-CD47nb released CD47nb in a lysis-dependent manner and that CD47nb induced phagocytosis of tumor cells by BMDMs in vitro.

Figures 8, 8A:
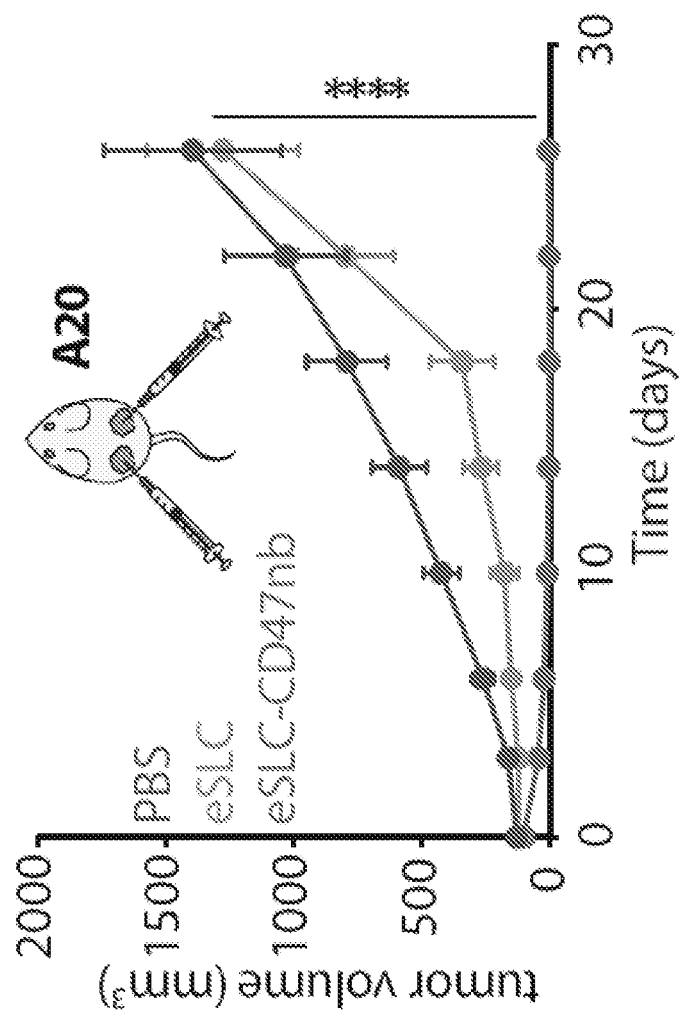
FIG. 8—Intratumoral production of CD47 nanobody by eSLC elicited antitumor responses in multiple syngeneic murine tumor models.
FIG. 8A is a graph of tumor volumes in BALB/c mice (n=7 per group) implanted subcutaneously with $5 \times 10^6$ A20 B-cell lymphoma cells on both hind flanks. When tumor volumes were 100-150 mm³, mice received intratumoral injections every 3-4 days with PBS, eSLC or eSLC-CD47nb in both tumors. Tumor growth curves (**** P<0.0001, two-way ANOVA with Tukey's multiple comparisons test, error bars represent s.e.m.).
Figure 8B:
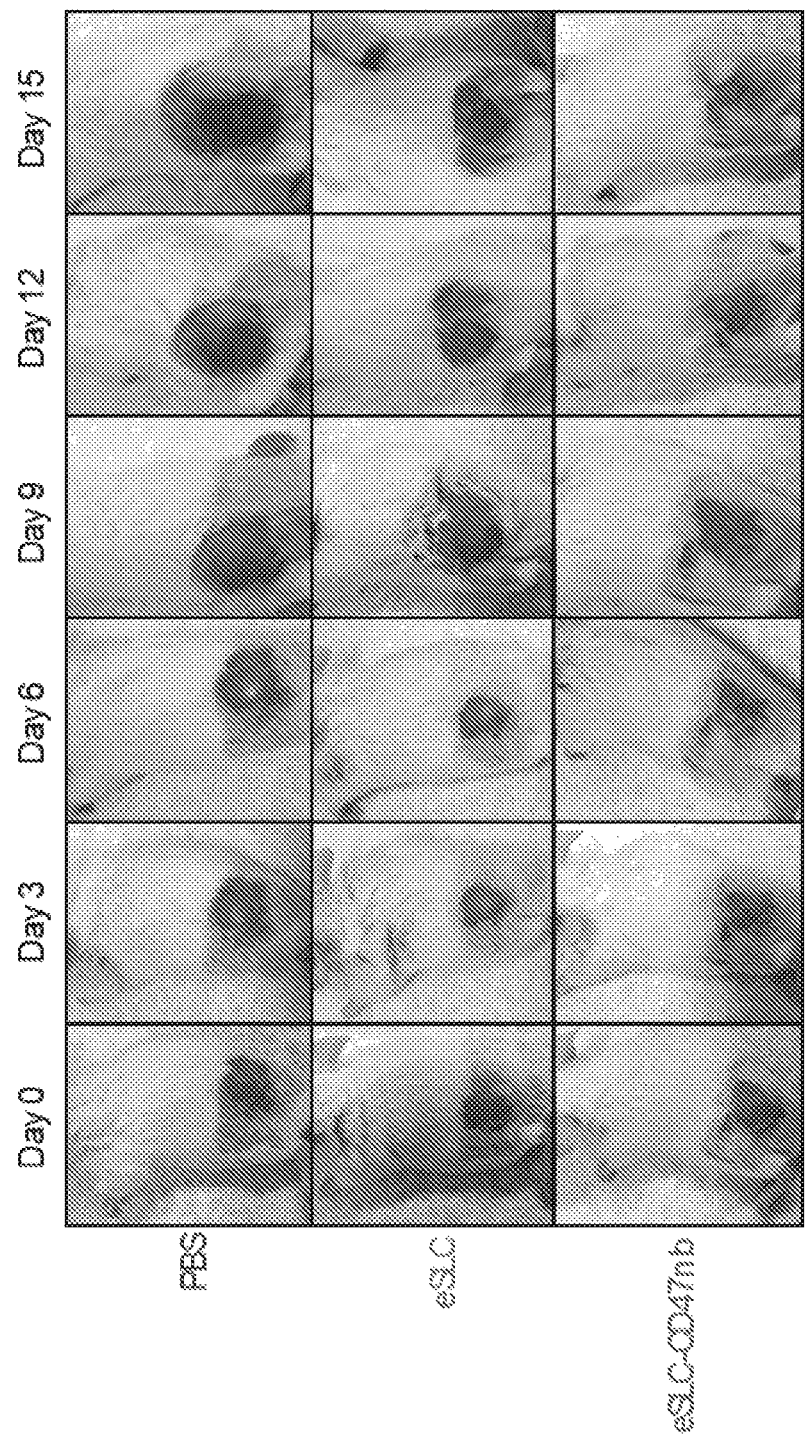
FIG. 8B are representative images of subcutaneous A20 tumor bearing BALB/c mice treated with PBS, eSLC, or eSLC-CD47nb.
Figure 8D:
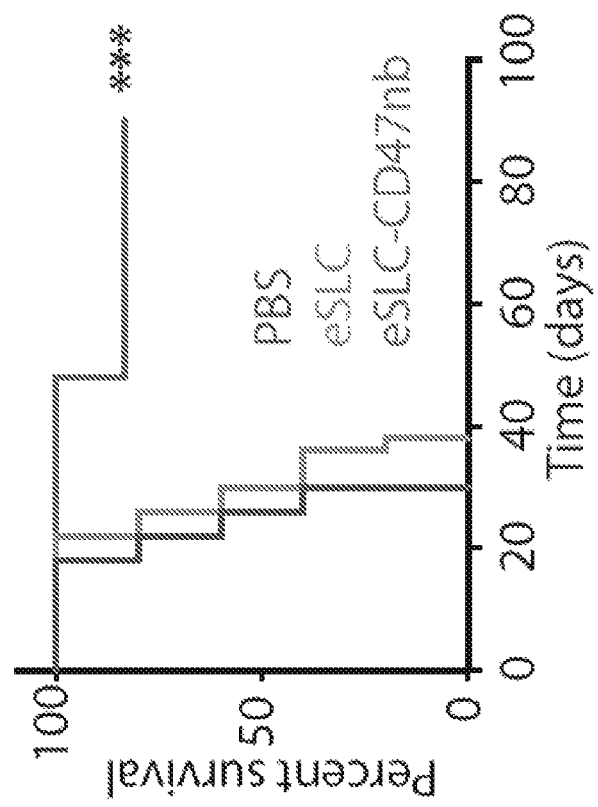
FIG. 8D is a Kaplan-Meier survival curves for A20 tumor bearing mice in each treatment group (n=5 per group, *P<0.001, Log-rank (Mantel-Cox test)).
Figure 8C:
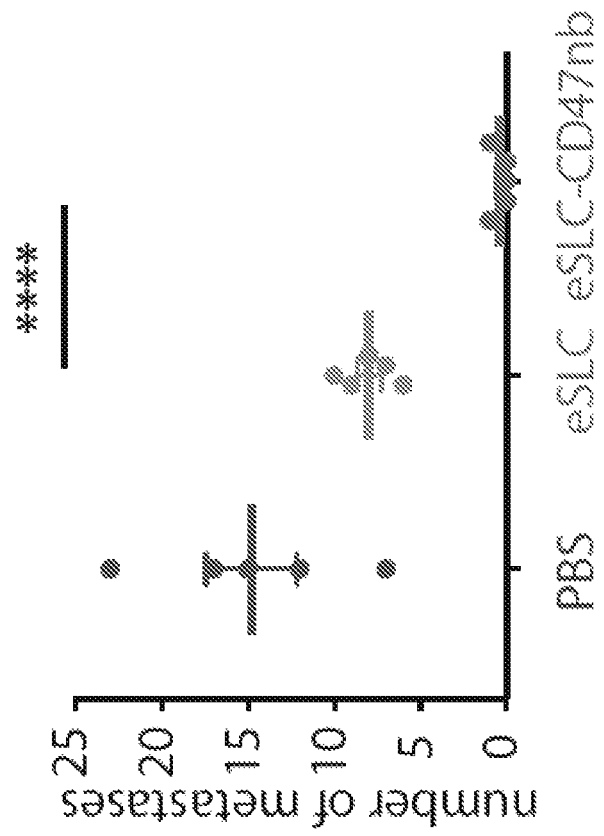
FIG. 8C is a graph of quantification of metastatic nodules present in livers on day 30 in each treatment group (n=5 per group, ** P<0.0001, unpaired t-test).

Example 9—In Vitro Confirmation of Expression and Lysis-Dependent Release of CD47nb Next the clinical efficacy of eSLC-CD47nb bacteria in a syngeneic mouse model was evaluated. BALB/c mice were implanted with $5 \times 10^6$ A20 cells in both hind flanks. When tumors reached 100-150 mm$^3$ in volume, mice were randomly divided into three groups (PBS, eSLC, eSLC-CD47nb) and received intratumoral injections of PBS, or $10^7$ colony forming units (CFU) of eSLC or eSLC-CD47nb bacteria resuspended in PBS, every 3-4 days for a total of 4 doses. While administration of control eSLC alone initially slowed tumor growth, likely due to the activation of innate immune cells by bacterial products released upon quorum-lysis, final tumor volumes were not statistically different from PBS treated mice. In contrast, administration of eSLC-CD47nb resulted in rapid and durable clearance of established A20 tumors within about 10 days of commencing therapy (FIG. 8A, FIG. 8B). Importantly, unlike in animals receiving intratumoral injections of PBS or control eSLC bacteria, liver metastases were rarely observable in mice treated with eSLC-CD47nb at 30 days post-treatment (FIG. 8C). Of note, about 80% of mice treated with eSLC-CD47nb survived greater than 90 days (FIG. 8D) and surviving mice were resistant to rechallenge by subcutaneous injection of $10 \times 10^6$ A20 cells (FIG. 8E), while naïve mice receiving the same batch of A20 cells developed tumors within a week of injection.

Figure 8F:
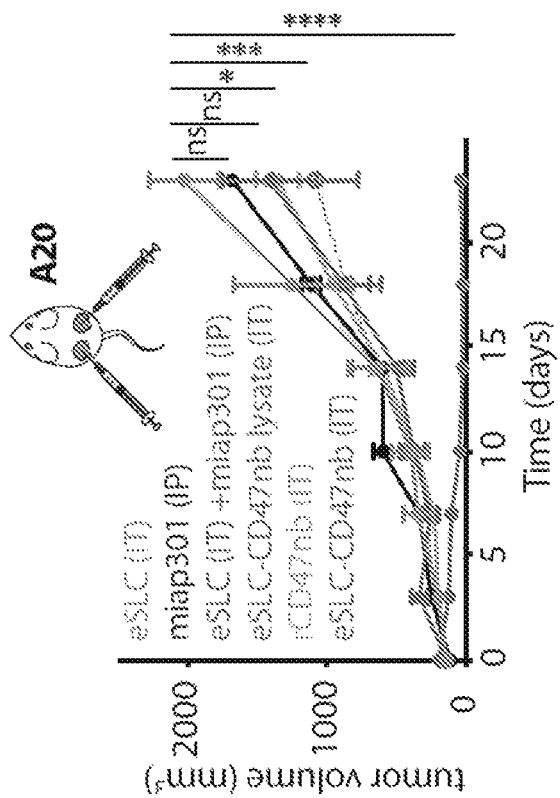
FIG. 8F is a tumor growth curve showing mice which when A20 tumor volume reached 100-150 mm³ received intratumoral injections of eSLC, eSLC-CD47nb bacterial lysate, recombinant CD47nb (rCD47nb, 50 µg) and eSLC-CD47nb, or intraperitoneal injections of anti-CD47 mAb (clone miap-301, 400 µg) alone or in combination with intratumoral eSLC for a total of 4 doses every 3-4 days. Tumor growth curves (n=4-8 mice per group, ** P<0.0001, * P<0.001, two-way ANOVA with Tukey's multiple comparisons test, error bars represent s.e.m.).
Figure 8E:
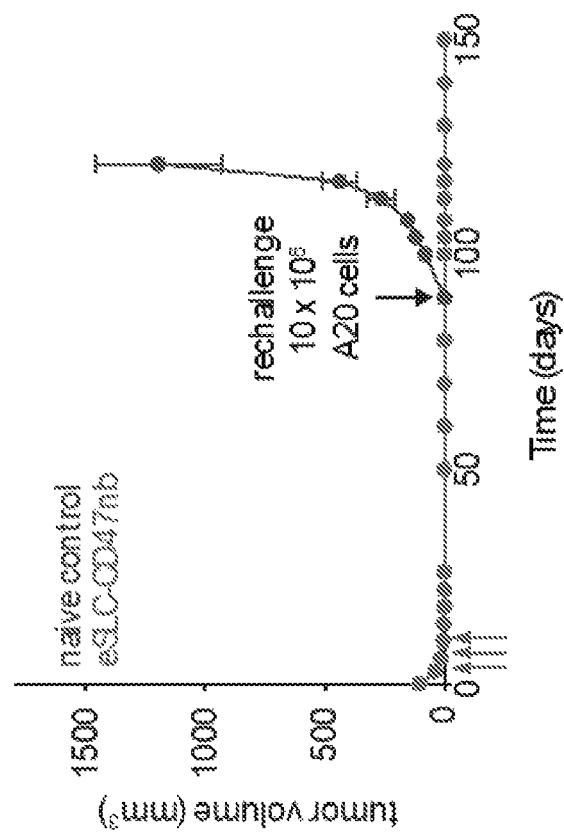
FIG. 8E is a tumor growth curve of mice that had completely cleared A20 tumors re-challenged with $10 \times 10^6$ A20 cells on day 90 following initial treatment. Naive mice received $5 \times 10^6$ A20 cells in each flank (n=4 mice per group).

Subsequently, the importance of therapeutic delivery by the individual components of the engineered, quorum-lysis system was evaluated (FIG. 8F). First, the efficacy of CD47 blockade via intraperitoneal delivery of anti-CD47 monoclonal antibody (miap301) with or without intratumoral injection of eSLC was evaluated. Neither group demonstrated significant efficacy in comparison to treatment of eSLC alone in an A20 mouse model. While mice treated intratumorally with programmable CD47nb (rCD47nb) or sonicated eSLC-CD47nb lysate exhibited slower tumor growth in comparison to mice treated with eSLC, complete tumor regression was only observed upon treatment with live, eSLC-CD47nb bacteria (FIG. 8F). These data collectively suggested that continuous SLC-mediated intratumoral release of CD47nb is essential to therapeutic efficacy.

Figure 8H:
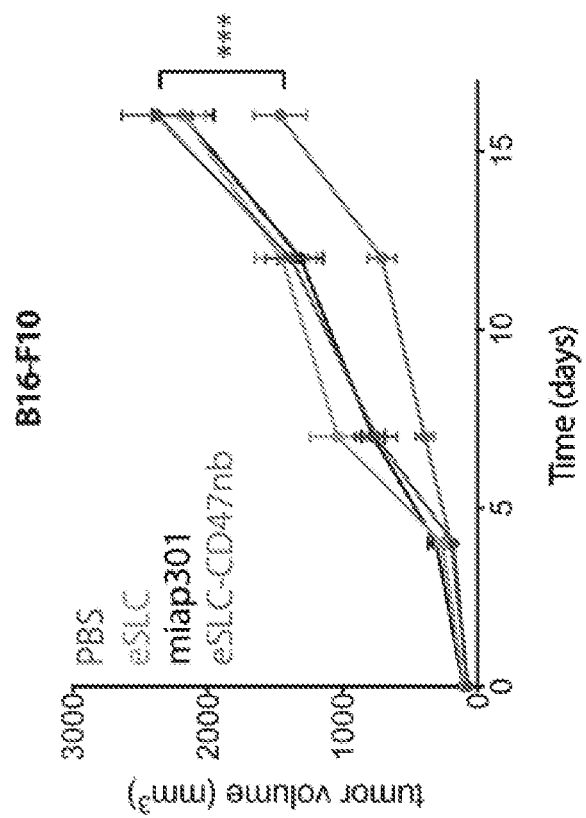
FIG. 8H are tumor growth curves from 7-week-old C57BL/6 mice subcutaneously injected with $5 \times 10^5$ B16-F10 melanoma cells into the hind flank. When tumors reached a volume of about 50-150 mm³ mice were randomized and received intraperitoneal injections of miap301 (400 µg) or intratumoral injections of PBS, eSLC, or eSLC-CD47nb every 3 days for a total of 4 doses. n=8-12 per group. P<0.001, two-way ANOVA with Tukey's multiple comparisons test, error bars represent s.e.m.
Figure 8G:
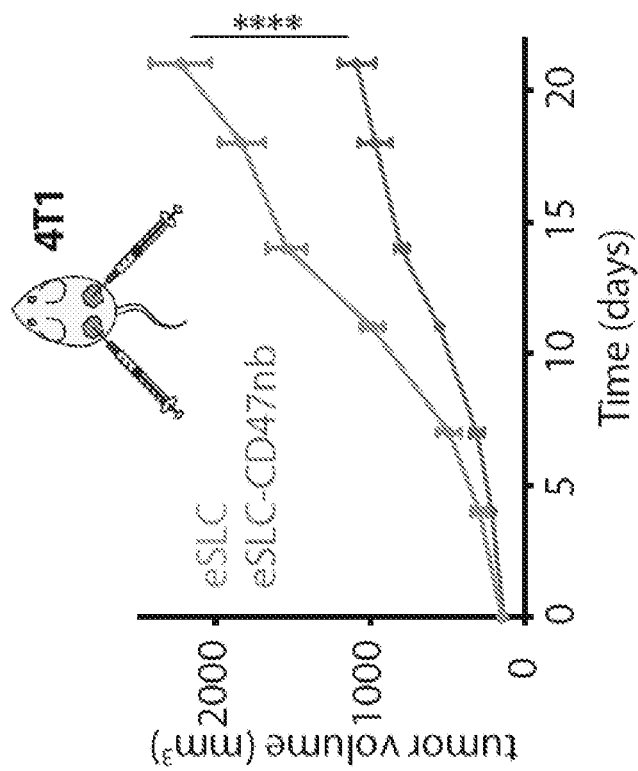
FIG. 8G are tumor growth curves of BALB/c mice (n=6-8 per group) implanted subcutaneously with $10^6$ 4T1-Luciferase mammary carcinoma cells. When tumors reached a volume of 200 mm³ mice were randomized and received intratumoral injections of PBS, eSLC, or eSLC-CD47nb every 3 days for a total of 4 doses (** P<0.0001, two-way ANOVA with Tukey's multiple comparisons test, error bars represent s.e.m.).
Figure 8J:
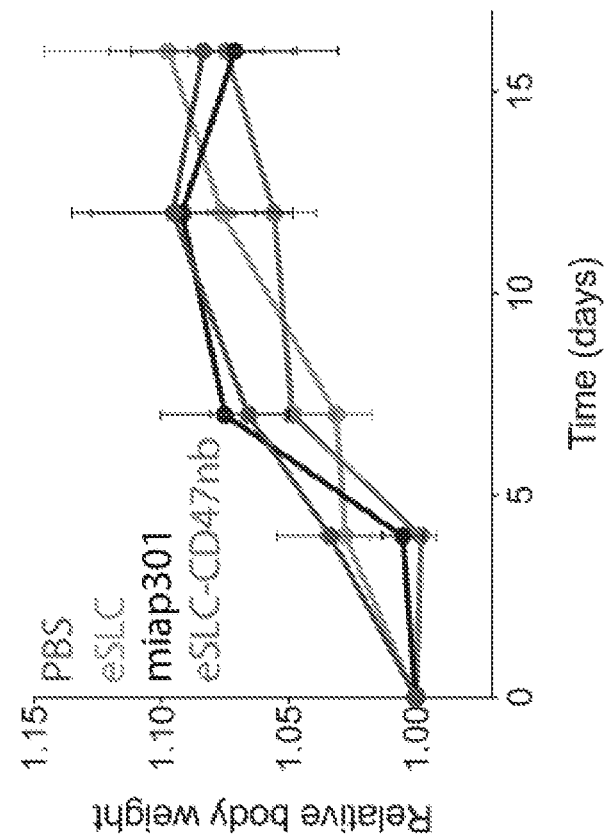
FIG. 8J is a graph of relative body weight of B16-F10 bearing C57BL/6 mice in each treatment group over time (ns, two-way ANOVA with Tukey's multiple comparisons test).
Figure 8I:
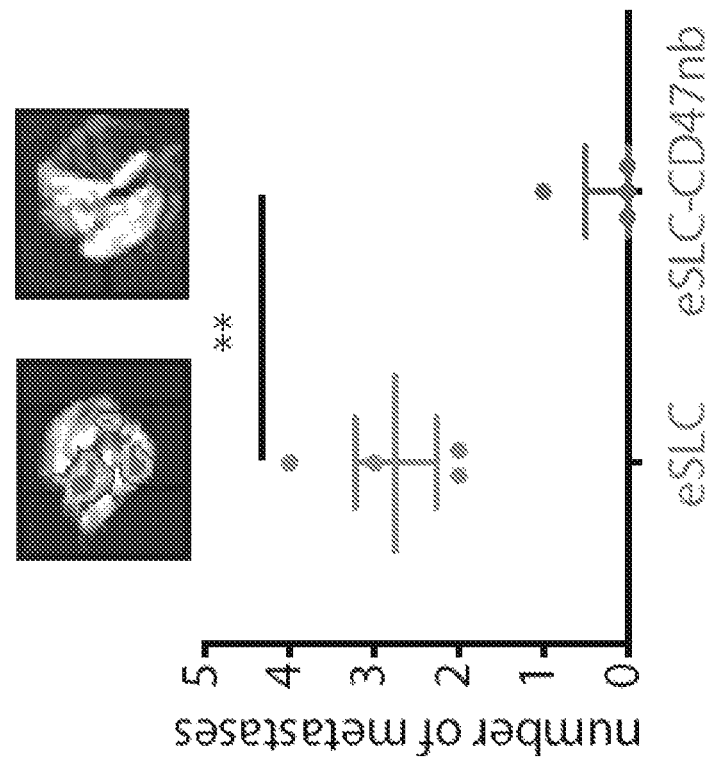
FIG. 8I are IVIS images of lungs extracted from 4T1-Luciferase hind-flank tumors (upper panel) and a graph (lower panel) of quantification of number of 4T1-Luciferase metastatic foci in lungs of mice treated with PBS, eSLC or eSLC-CD47nb ( P<0.01, unpaired t-test).

To assess the broader applicability of the approach, efficacy by intravenous administration was evaluated, and using additional murine tumor models. Significant therapeutic efficacy was also observed when eSLC-CD47nb was intratumorally injected in other syngeneic murine models, such as triple negative breast cancer (4T1, FIG. 8G) and melanoma (B16F10, FIG. 8H). Lung metastases were notably reduced in mice receiving eSLC-CD47nb in the 4T1 triple-negative breast cancer model (FIG. 8I). No changes in body weight were seen between the different treatments in the murine melanoma models (FIG. 8J).

Figures 9C, 9D:
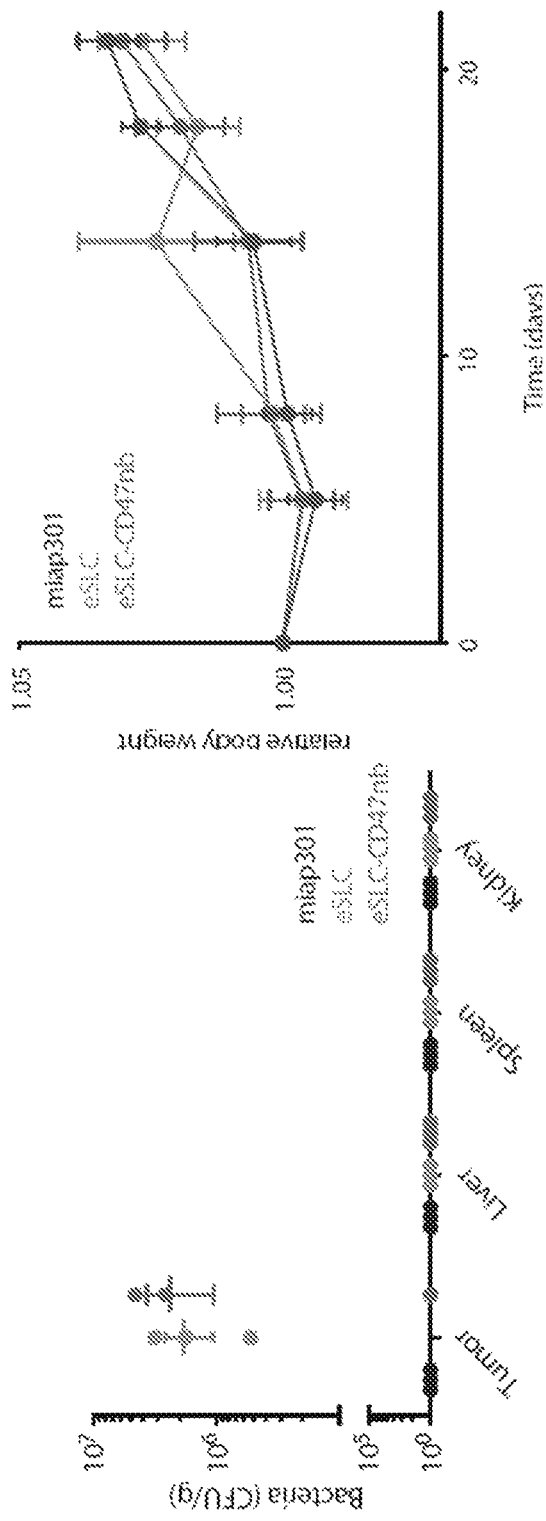
FIG. 9C shows the biodistribution of eSLC-CD47nb E. coli on day 8 following final intravenous bacterial treatment. Excised tumors, livers, spleens and kidneys were homogenized, serially diluted and plated on LB agar plates. Colonies were counted to determine CFU/g of tissue.
FIG. 9D is a graph of relative body weight of A20 tumor bearing BALB/c mice receiving intravenous bacterial injections or intraperitoneal injections of miap301 (ns, two-way ANOVA with Tukey's multiple comparisons test).

The ability of eSLC-CD47nb to safely target and treat tumors via systemic intravenous delivery was also explored (FIG. 9A). In comparison to systemically delivered CD47 antibody (miap301), intravenous eSLC-CD47nb showed significantly slower tumor growth (FIG. 9B). Following treatment, bacteria appeared to be exclusively localized within tumors as compared to the liver, spleen, and kidney (FIG. 9C). Bacterial therapy was well-tolerated by animals, with no changes in body weight observed over the course of treatment or throughout the observation period by both intratumoral and intravenous delivery routes (FIG. 9D).

Overall, these results indicated that eSLC-CD47nb safely promoted local tumor regression while also preventing metastasis, suggesting the induction of systemic antitumor immunity that is likely mediated by tumor-specific T cells.

Example 10—Treatment with eSLC-CD47nb Activated T Cell Response

Figure 10D:
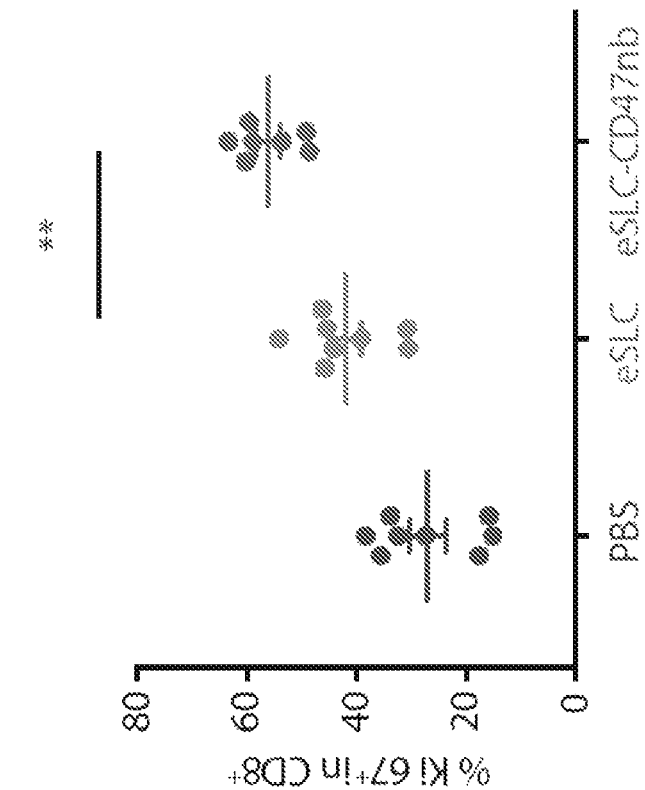
FIG. 10D is a graph of the percent of isolated intratumoral Ki-67+ in CD8+ cells in each group of treated mice.
Figure 10C:
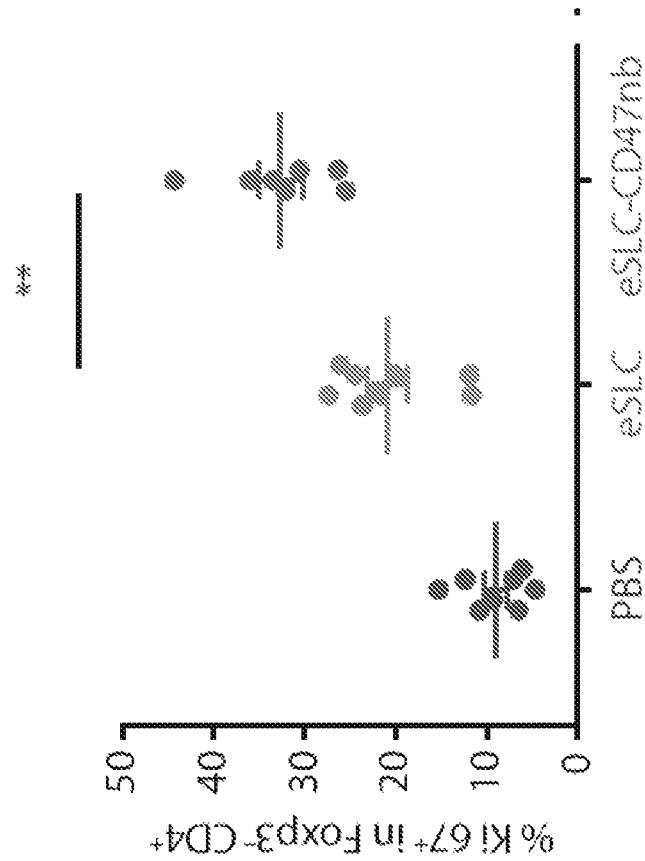
FIG. 10C is a graph of the percent of isolated intratumoral Ki-67+ in Foxp3-CD4+ cells in each group of treated mice.
Figures 10E, 10F:
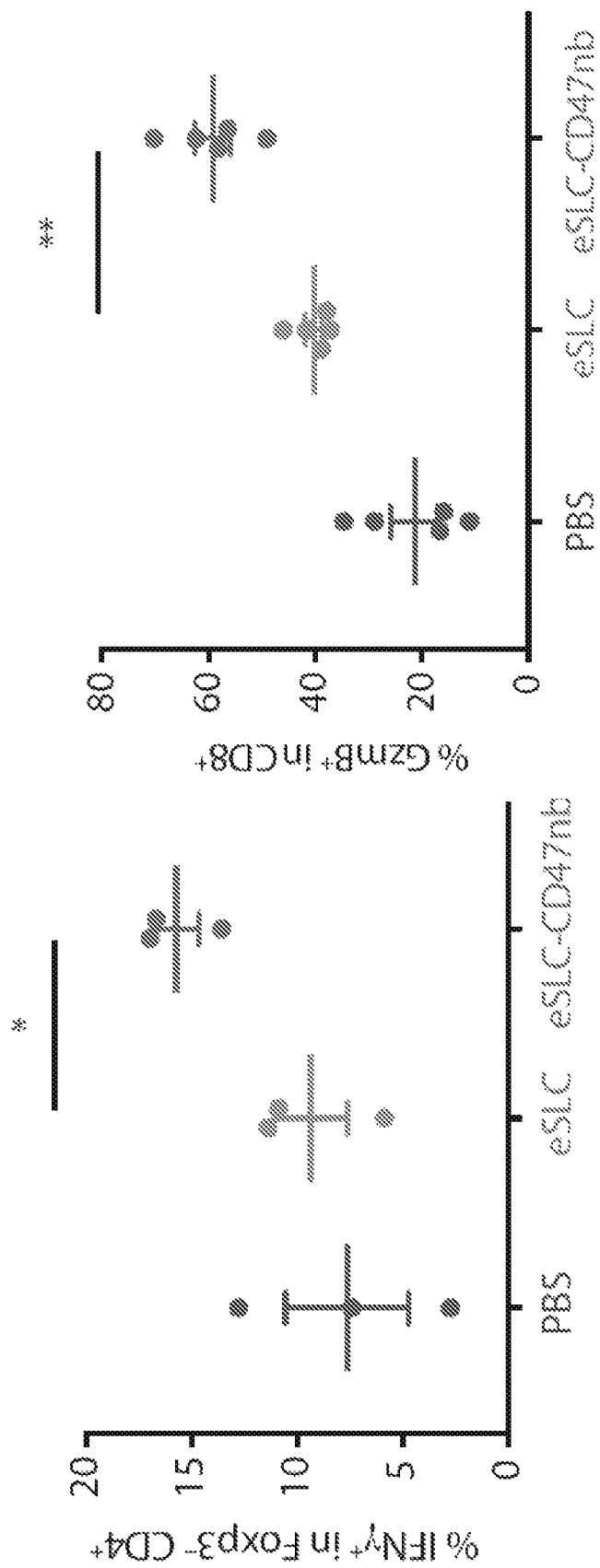
FIG. 10E is a graph of the percent of isolated intratumoral IFN-γ$^+$ in Fox3-CD4+ cells in each group of treated mice.
FIG. 10F is a graph of the percent of intratumoral Granzyme-B positive CD8+ cells.

Recent studies have highlighted the importance of antigen presenting cells and effector T cells as being indispensable for anti-CD47-mediated clinical responses (Liu et al. 2015; Kauder et al. 2018). It was reasoned that local inflammation induced by bacterial lysis coupled with localized blockade of CD47 on tumor cells would increase tumor cell phagocytosis and tumor antigen presentation, and thereby enhance the priming of antitumor T cells. Immunophenotyping of A20 tumors treated with eSLC-CD47nb revealed increased frequencies of MHCII$^{hi}$ CD11b$^+$F4/80$^+$ macrophages 3 days after commencing therapy (FIG. 10A), suggesting an increase in the antigen presentation ability of tumor macrophages at early time points. Additionally, on day 8, a decline in SIRPα$^+$ macrophages within the tumor was observed (FIG. 10B). Past studies have shown that LPS exposure may lead to SIRPα downregulation in vitro (Kong et al. 2007). It was hypothesized that combined release of lysis adjuvants and a lack of SIRPα downstream signaling following CD47 blockade may lead to reduced surface expression of SIRPα on tumor-associated macrophages. Additionally, immunophenotyping of A20 tumors treated with eSLC-CD47nb revealed increased proliferation of both Foxp3$^-$CD4$^+$ and CD8$^+$ T cells in comparison to tumor bearing mice treated with eSLC bacteria (FIG. 10C, FIG. 10D). Furthermore, tumor-infiltrating Foxp3$^-$CD4$^+$ T cells from eSLC-CD47nb-treated tumors produced significantly higher levels of IFN-γ following ex vivo restimulation with PMA and ionomycin (FIG. 10E). While eSLC-CD47nb did not lead to significant changes in IFN-γ levels in CD8$^+$ T cells (results not shown), markedly elevated levels of intratumoral Granzyme B$^+$ CD8$^+$ T cells were observed (FIG. 10F) as well as other parameters of adaptive immune activation (FIGS. 10H-10L).

Figure 10G:
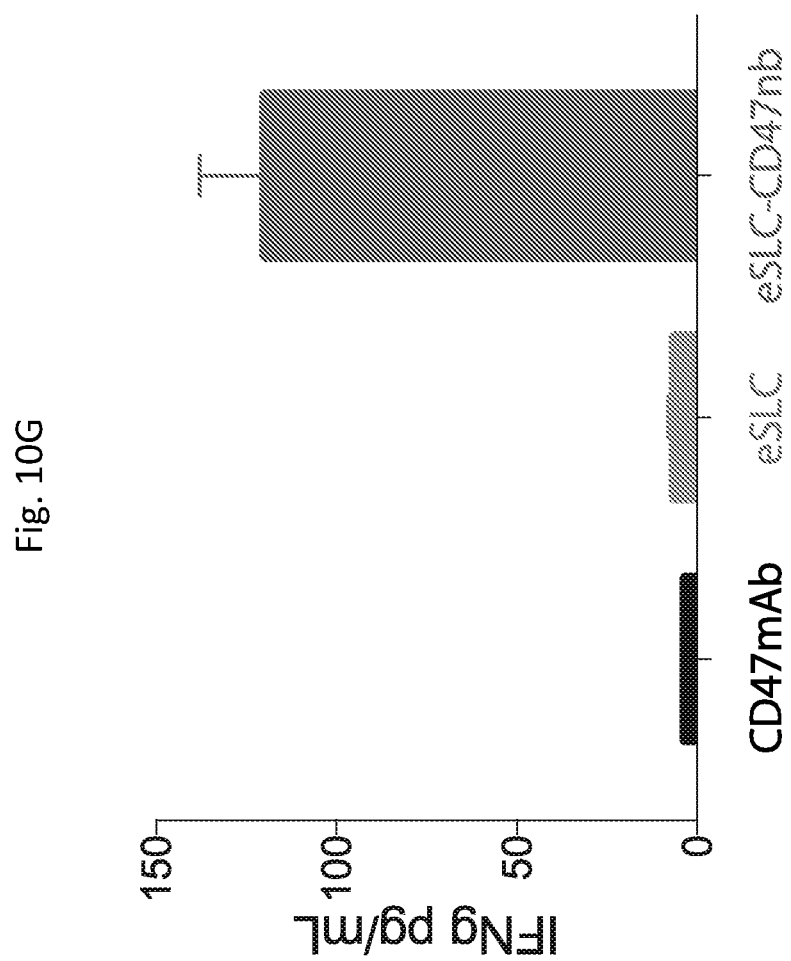
FIG. 10G is a graph showing IFNγ production by splenic T cells in each group of treated mice. (n=2 mice, 3 technical replicates).
Figure 10H:
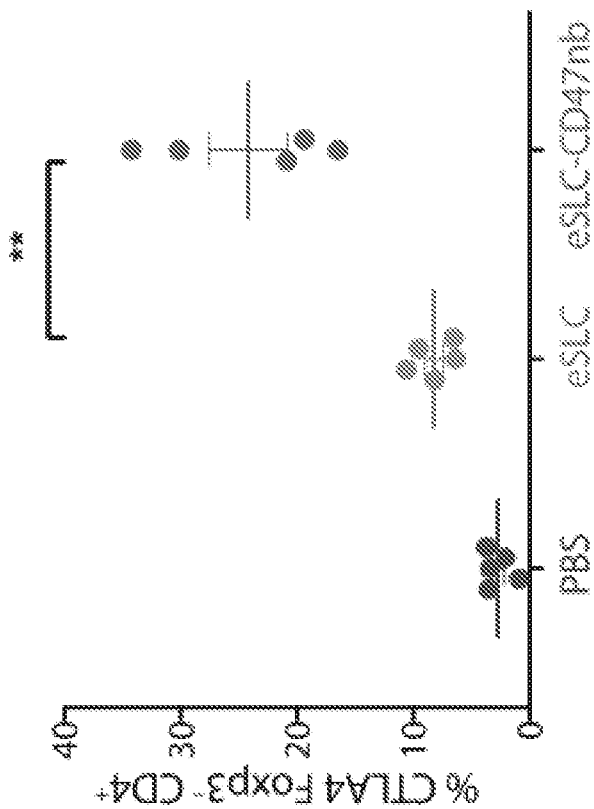
FIG. 10H is a graph of the frequencies of CTLA4+ within Foxp3-CD4+ in each group of treated mice.
Figure 10I:
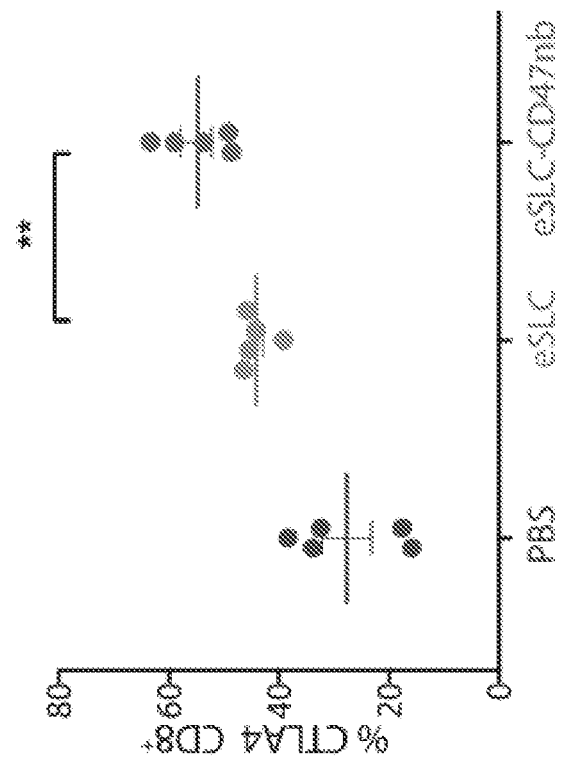
FIG. 10I is a graph of the frequencies of CTLA4+ within CD8+ cells in each group of treated mice.
Figure 10J:
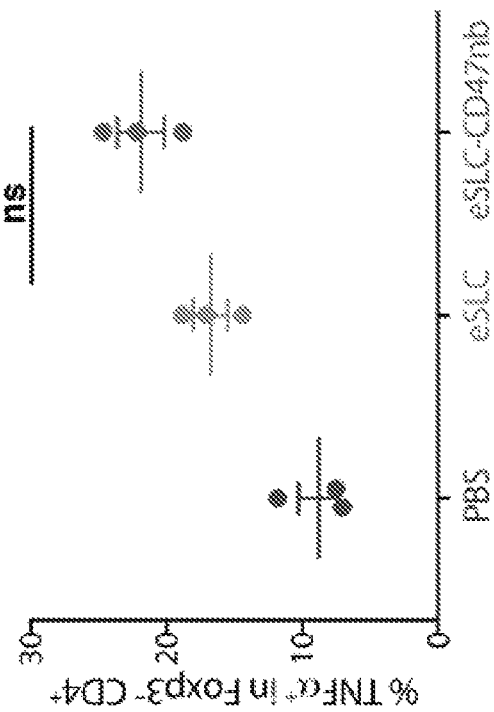
FIG. 10J is a graph of frequencies of TNFα+ cells within FOXP3-CD4+ T cell populations following ex vivo stimulation in each group of treated mice (ns, not significant (P>0.05), n=3 tumors per group, unpaired two-tailed t-test).
Figure 10K:
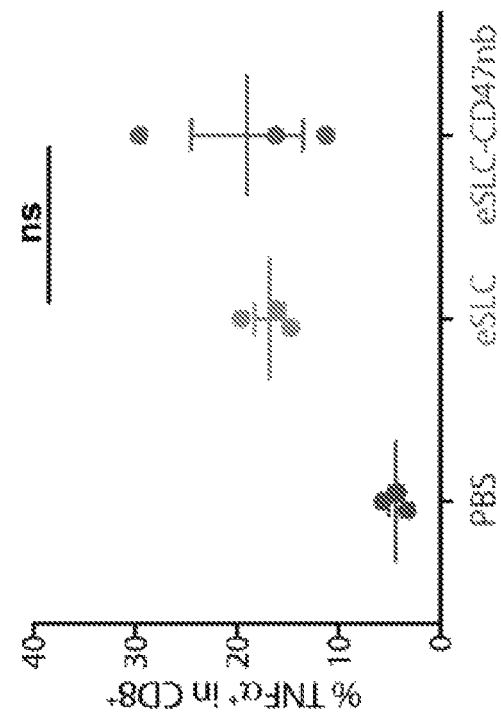
FIG. 10K is a graph of frequencies of TNFα+ CD8+ cell populations following ex vivo stimulation in each group of treated mice (ns, not significant (P>0.05), n=3 tumors per group, unpaired two-tailed t-test).
Figure 10L:
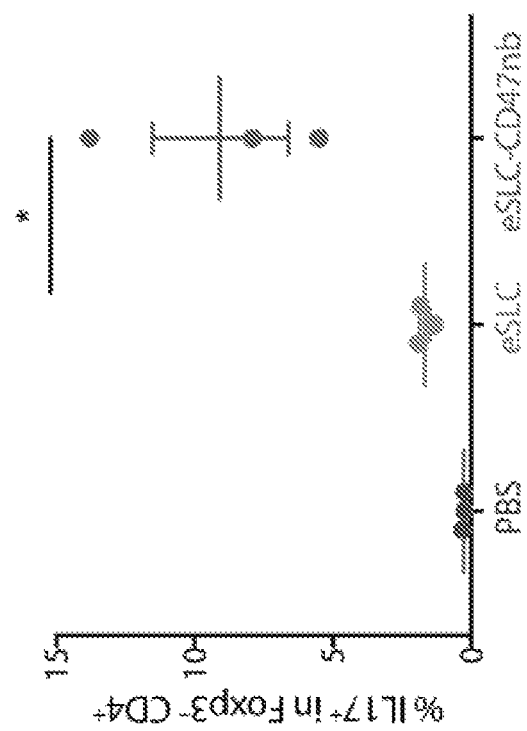
FIG. 10L is a graph of frequency of IL-17+ cells within the FOXP3-CD4+ cell population following ex vivo stimulation (*P=0.0402, n=3 tumors per group, unpaired two-tailed t-test).

Additionally, these T cell responses appeared to be tumor antigen—specific as overnight in vitro co-culture of irradiated A20 cells with splenocytes derived from mice treated with eSLC-CD47nb led to robust secretion of IFN-γ (FIG. 10G). Interestingly, mice treated with miap301 exhibited no elevated IFN-γ response in comparison to those receiving eSLC-CD47nb. These data suggested that eSLC-CD47nb not only supported the activation and proliferation of intratumoral T cells, but also lead to the induction of systemic anti-A20 memory T cell responses.

Example 11—Abscopal Effect of the Treatment with eSLC-CD47nb

Figure 11C:
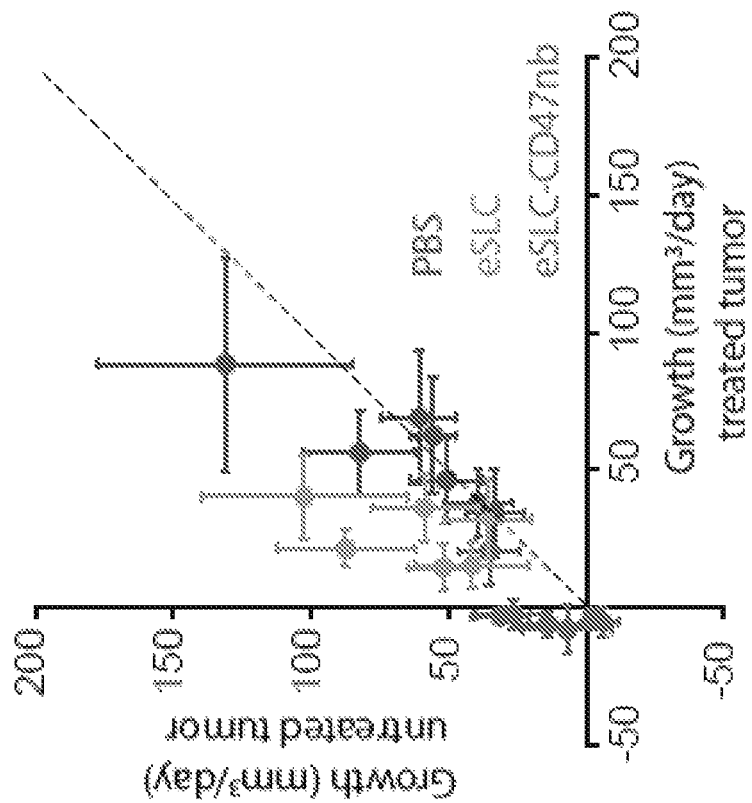
FIG. 11C is a tumor growth curves of untreated tumors (** P<0.0001, two-way ANOVA with Tukey's multiple comparisons test, error bars represent s.e.m.).
Figure 11D:
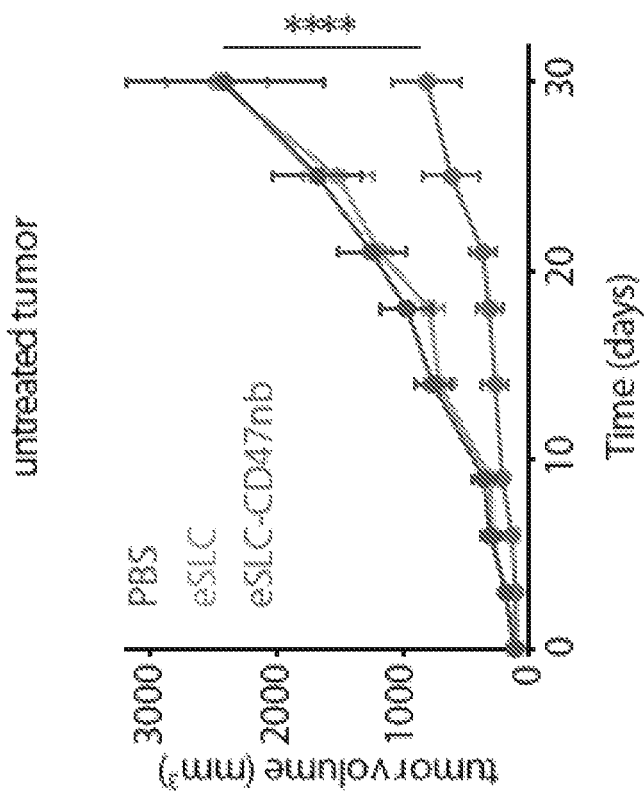
FIG. 11D is a plot of untreated tumor growth rate (mm³/day) vs. treated tumor growth rate (mm³/day) for each mouse. Dotted line indicates slope=1, points represent means, error bars represent s.e.m.

Durable remission from cancer requires not only elimination of treated tumors but also systemic antitumor immunity for the clearance of distant metastases. Based on the observation that eSLC-CD47nb enhances the effector function of tumor-infiltrating T cells within treated tumors, it was examined whether SLC-CD47nb could delay growth of untreated tumors. Mice injected with A20 tumors on both flanks were treated with eSLC-CD47nb in a unilateral fashion (FIG. 11A). While control eSLC bacteria had no effect on the growth of untreated tumors, treatment of the primary tumor with eSLC-CD47nb substantially slowed the growth of untreated tumors on the opposing flank (FIG. 11B, FIG. 11C). To further quantify this effect, the mean growth rates (mm/day) of treated vs. untreated tumors was calculated by calculating the slopes in tumor volume trajectories for each mouse (FIG. 11D). These data indicated that eSLC-CD47nb treated mice showed decreased growth rates in both treated and untreated tumors compared to controls.

Figure 11E:
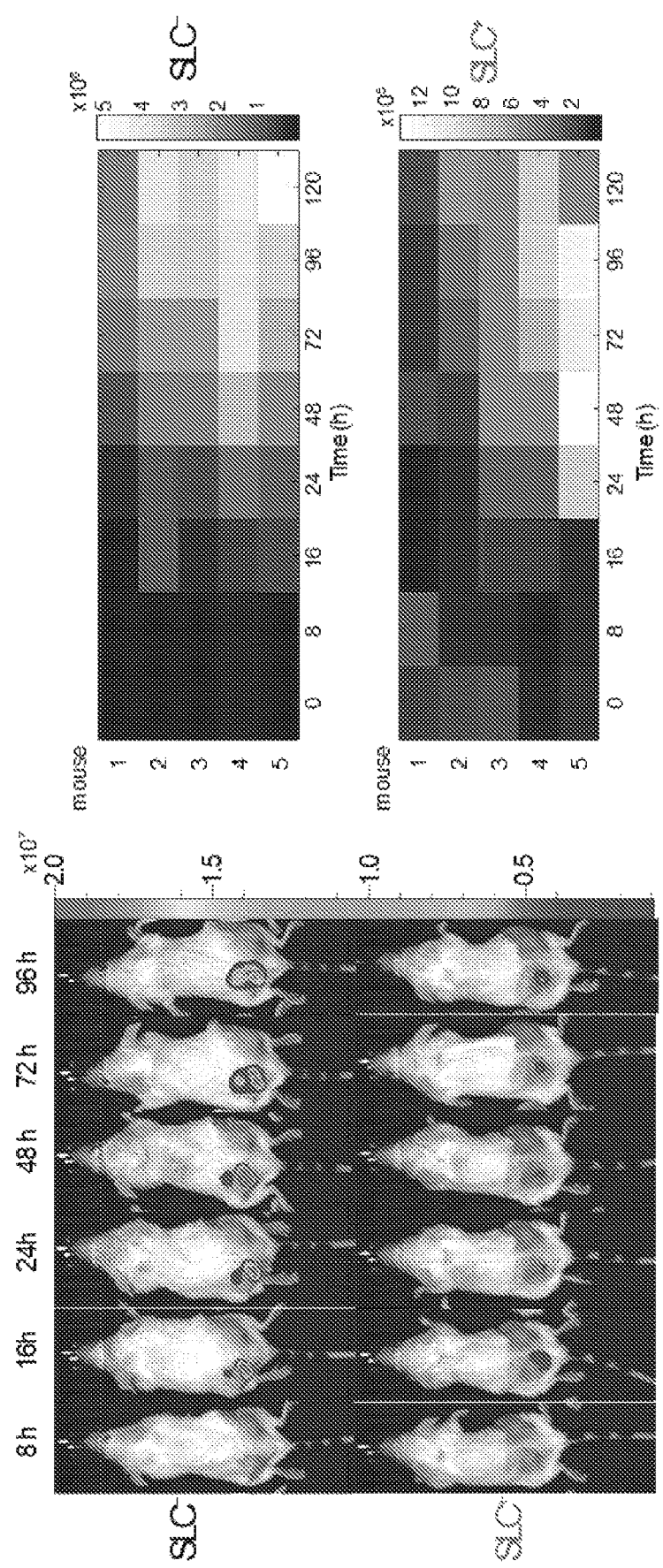
FIG. 11E are representative IVIS images of A20 tumor bearing mice intratumorally injected with SLC– and SLC+ EcNisLux (scale represents radiance (p/s/cm2/sr) (left panel), and luminescence heat maps over time (right panel). Luminescence was measured over time via IVIS. (n=5 mice per group). Colors represent average radiance (p/s/cm2/sr).

The possibility that SLC-CD47nb bacteria injected into the primary tumor migrated via systemic circulation to seed the untreated lesion was considered. A luminescent strain of SLC E. coli (EcNisLux$^{39}$) was intratumorally injected into a single tumor and IVIS imaging performed over 5 days. In comparison to a SLC$^-$ strain where luminescence continuously increased over time, SLC EcNisLux exhibited fluctuations in luminescence indicating in vivo lysis behavior (FIG. 11E). Importantly, luminescent signal was limited to the injected lesion and no signal was detected in the untreated tumor or other organs, indicating that an adaptive immune response may be mediating this abscopal effect.

Figures 11F, 11G:
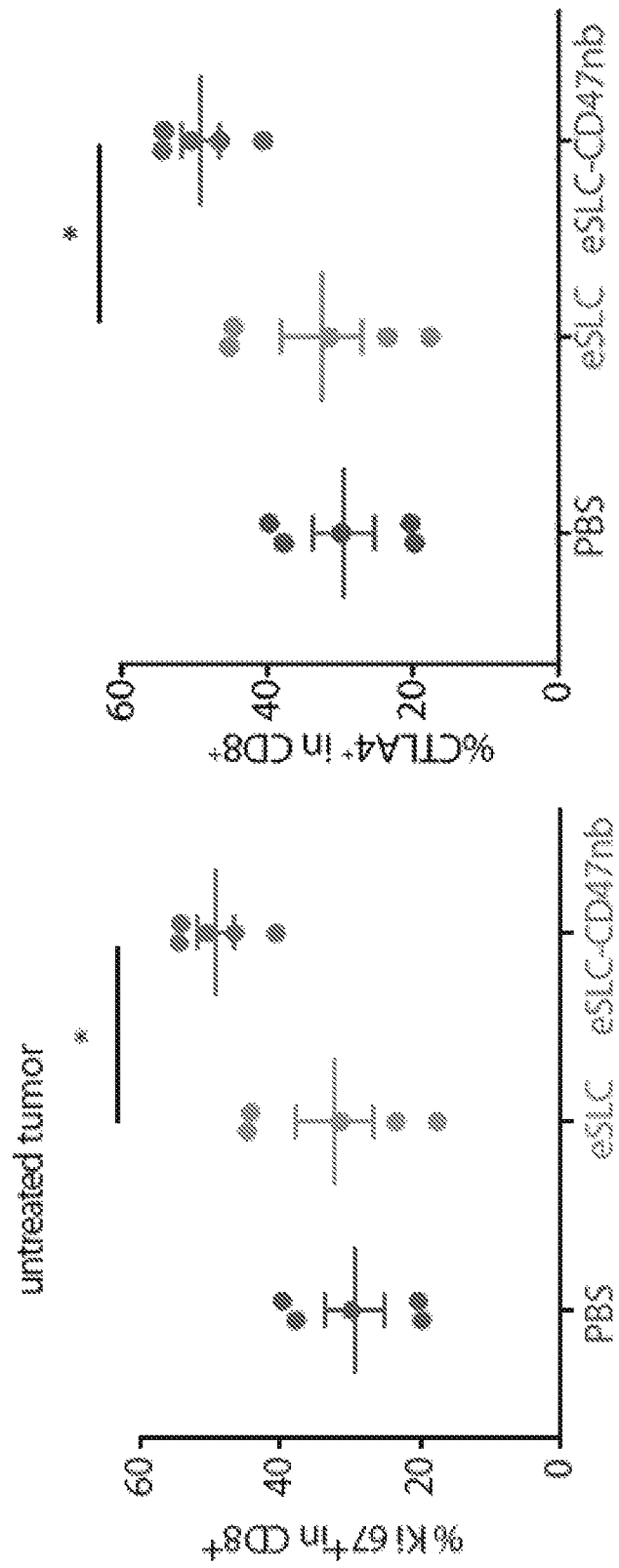
FIG. 11F is a graph of frequency of KI67+ in CD8+ cells in untreated tumors.
FIG. 11G is a graph of the frequencies of CTLA4– cells within the FOXP3-CD8+ cell population in untreated tumors (*P=0.0259, unpaired two-tailed t-test).
Figure 11I:
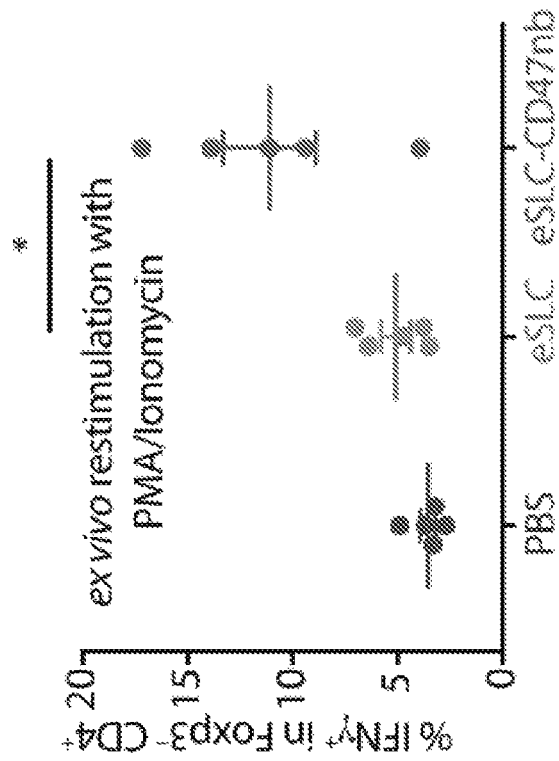
FIG. 11I is a graph of frequency of tumor infiltrating IFNγ+ cells within the FOXP3-CD4+ cell population following ex vivo stimulation with PMA and ionomycin in the presence of brefeldin A. (*P=0.0327, unpaired two-tailed t-test).
Figure 11H:
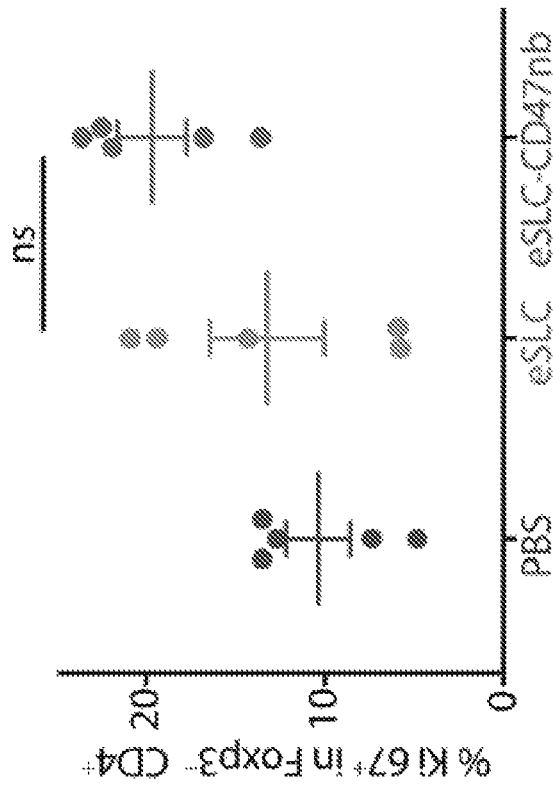
FIG. 11H is a graph of the frequency of Ki-67+ cells within the FOXP3-CD4+ cell population following ex vivo stimulation with PMA and ionomycin in the presence of brefeldin A. (P>0.05, unpaired two-tailed t-test).
Figure 11J:
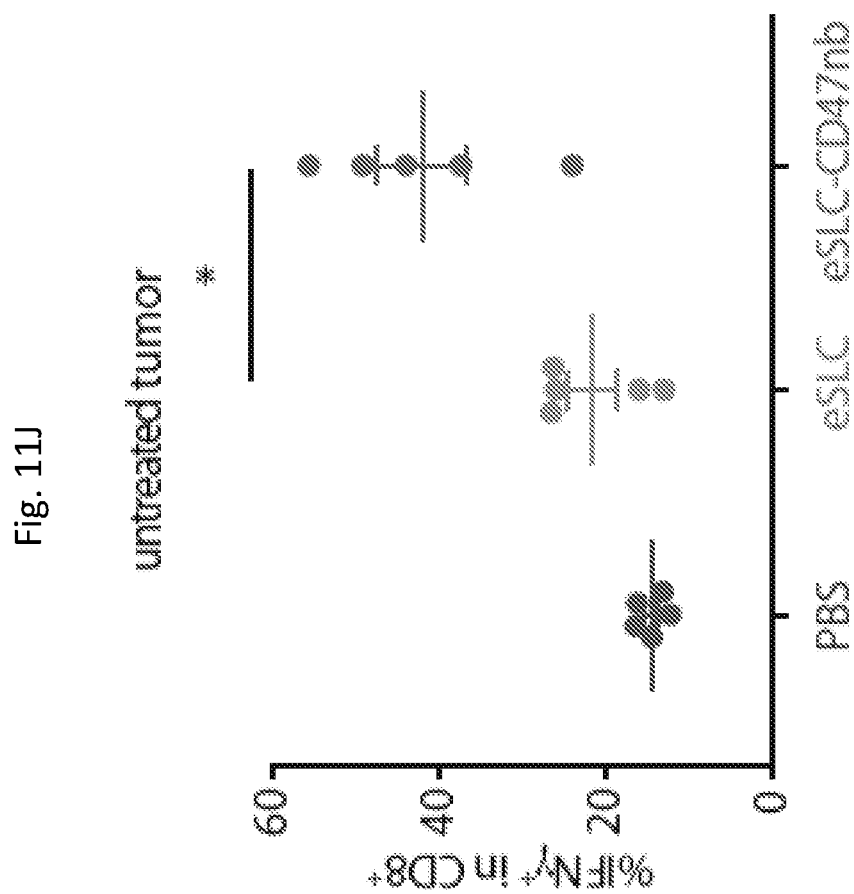
FIG. 11J is a graph of frequencies of intratumoral IFN-γ+ in CD8+ tumor infiltrating T cells in untreated tumor cells following ex vivo stimulation with PMA and ionomycin in the presence of brefeldin A. (*P=0.0104, unpaired two-tailed t-test).

In support of this hypothesis, flow cytometric analysis of lymphocytes isolated from untreated tumors of mice whose primary tumors were injected with eSLC-CD47nb showed increased frequencies of activated (FIG. 11G) and proliferating CD+8 T cells (FIG. 11F) as well as a trend towards increased frequencies of proliferating FOXP3-CD4+ cells (FIG. 11H). Additionally, a significantly higher percentage of FOXP3-CD4+ and CD8+ T cells producing IFNγ following ex vivo restimulation with PMA and ionomycin was observed (FIG. 11I, 11J).

Figure 11K:
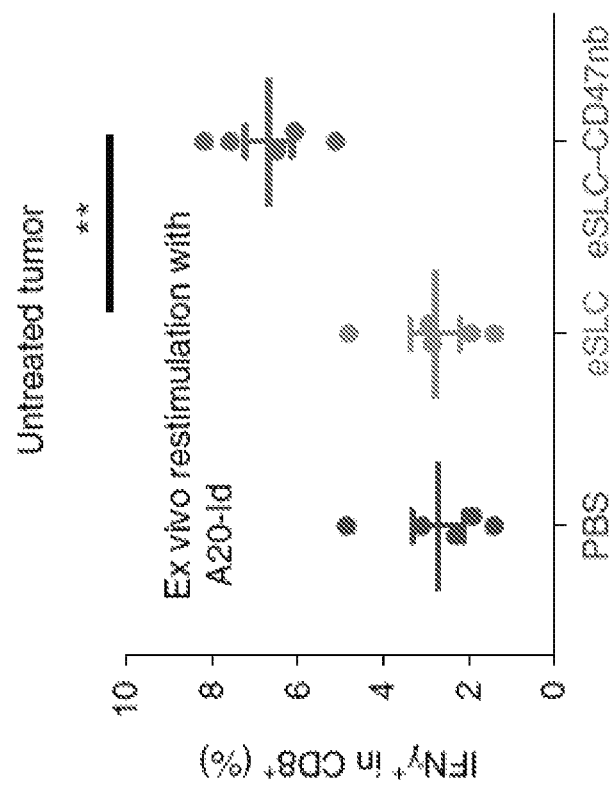
FIG. 11K is a graph of frequencies of intratumoral IFNγ+CD8+ after ex vivo stimulation with A20-Id peptide n the presence of brefeldin A. (n=5 per group, **P=0.0012, unpaired t-test).

In order to directly assess the reactivity of T cells in untreated tumors to an endogenous tumor antigen, tumor-infiltrating lymphocytes were stimulated with an H-2Kd-restricted peptide (A20-Id, DYWGQGTEL (SEQ ID NO: 2)), corresponding to the unique idiotype of the antibody expressed by A20 lymphoma cells, which has previously been shown to activate tumor-antigen-specific CD8+ T cells (Armstrong et al. 2002). Following ex vivo stimulation with A20-Id peptide, a significant observation in a higher frequency of IFNγ+CD8+ T cells in mice treated with eSLC-CD47nb in comparison to mice treated with eSLC or PBS was made (FIG. 11K). As further confirmation of the specificity of this assay, the frequency of IFNγ+FOXP3-CD4+ cells (FIG. 11L) was unchanged—consistent with this peptide being MHC class I restricted. These data suggest that treatment with eSLC-CD47nb enhances tumor-antigen-specific CD8+ T cell activity in the untreated tumor.

Figure 11N:
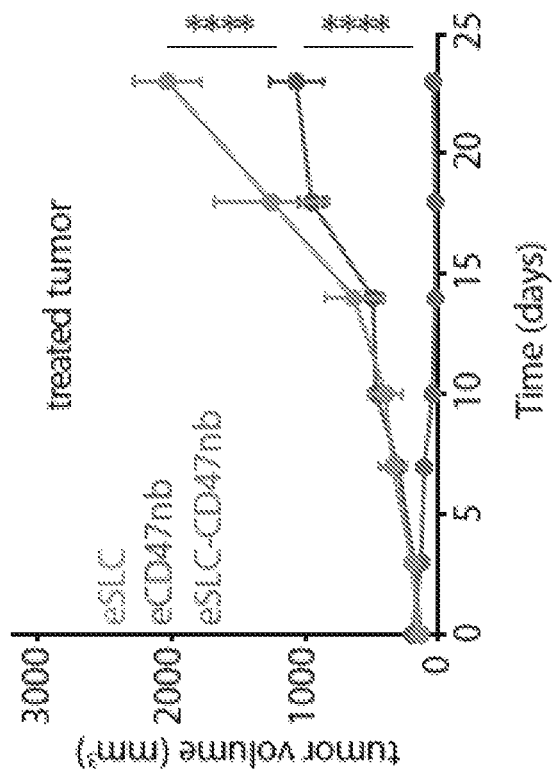
FIG. 11N is a tumor growth curves of treated A20 tumors following unilateral intratumoral injections of eSLC, eCD47nb or eSLC-CD47nb every 3-4 days for a total of 4 doses (n=4 per group, * P<0.001,  P<0.0001, two-way ANOVA with Tukey's multiple comparisons test, error bars represent s.e.m.).
Figure 11M:
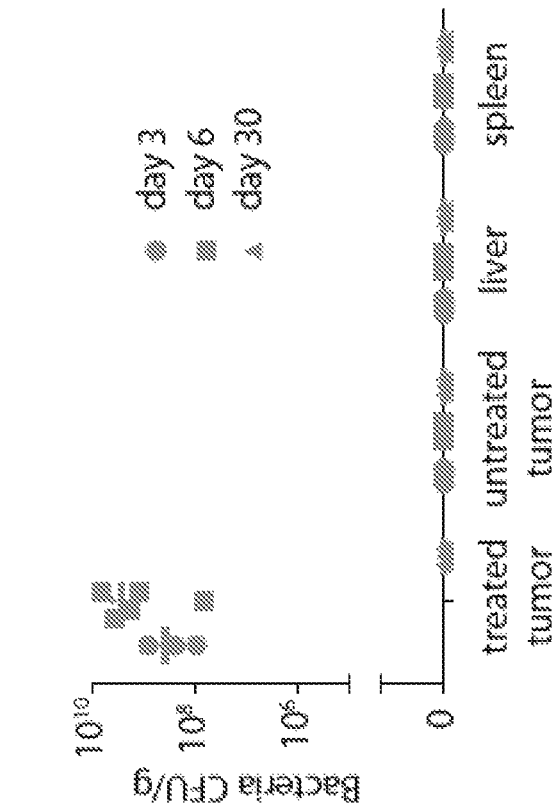
FIG. 11M shows the biodistribution of SLC *E. coli* on day 3, 6 and 30 following intratumoral bacterial injection. Excised tumors, livers and spleens were homogenized and plated on LB agar plates. Colonies were counted to determine CFU/g of tissue. Limit of detection $10^3$ CFU/g.
Figure 11O:
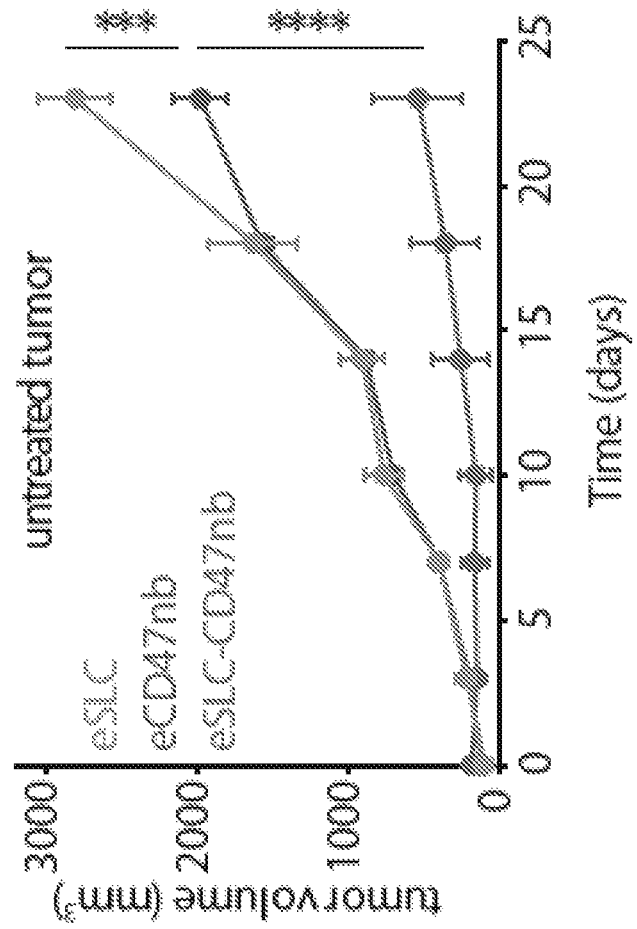
FIG. 11O is a tumor growth curves of untreated A20 tumors following unilateral intratumoral injections of eSLC, eCD47nb or eSLC-CD47nb every 3-4 days for a total of 4 doses (n=4 per group, * P<0.001, **** P<0.0001, two-way ANOVA with Tukey's multiple comparisons test, error bars represent s.e.m.).

To further exclude the possibility of bacterial trafficking, the biodistribution of SLC+E. coli at 3 separate time points following unilateral intratumoral injection was assessed. Plating of homogenized tumors and organs revealed that bacterial growth remained restricted to treated tumors and no bacteria could be cultured from untreated tumors or livers and spleens of treated mice above the limit of detection (about 1×10$^3$ CFU) (FIG. 11M). Additionally, SLC mediated release of CD47nb appeared to be necessary for inducing a potent abscopal effect. While eCD47nb (SLC$^-$ strain constitutively producing CD47nb) administration slowed the growth of treated lesions in comparison to treatment with eSLC (FIG. 11N), it exhibited a much weaker effect on untreated tumors in comparison to eSLC-CD47nb (FIG. 11O).

Taken together, these results clearly demonstrated that the engineered quorum-lysis immunotherapeutic delivery system generated potent, tumor-specific adaptive immune responses that operate systemically to clear distant tumor lesions including those at untreated or remote sites ("abscopal effect").

Example 12—Bacteria Containing High Affinity SIRPα Variants as the Deliverable Therapeutic Agent Further studies were conducted using the E. coli Nislux bacteria with the integrated synchronized lysis circuit described in Example 3 (EcN-SLC) further engineered anti-CD47 nanobody described in Example 7 (CD47nb) and two different high-affinity SIRP α variants, CV1 and FD6.

CV1 and FD6 high-affinity human SIRPα variants that bind CD47 with a higher affinity than endogenous SIRPα and hence antagonize the interaction between CD47 and SIRPα. The sequences were obtained from the literature (Weislopf et al. 2013). Additionally, data therein has suggested that FD6 and CV1 both also bind mouse CD47, albeit with a lower affinity than human. The results herein suggested EcN-SLC-int mediated delivery of CV1 has a stronger therapeutic effect than that of FD6.

The EcN-SLC were transformed with the p246_AT containing CD47nb (as described in Examples 1 and 6) plasmid. In a similar way, the EcN-SLC were transformed with plasmids encoding CV1 and FD6.

A scrambled nanobody control EcN-SLC-int-FC2 was also produced.

Figures 12, 12A:
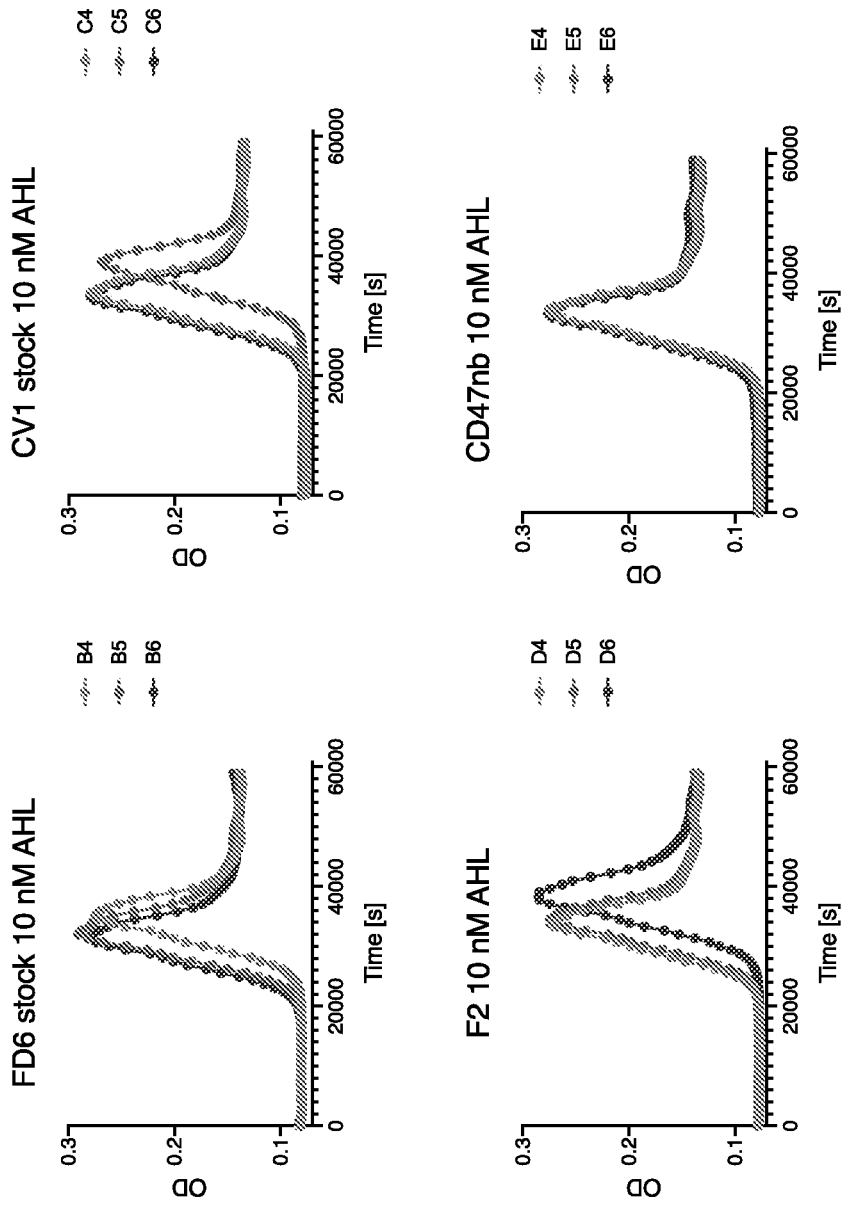
FIG. 12—Intratumoral production of CD47 nanobodies and SIRPα variants by EcN-SLCint elicited antitumor responses in multiple syngeneic murine tumor models.
FIG. 12A are graphs showing the results of plate reader experiments using SLC-integrated *E. coli* Nislux with therapeutics expressed in p246_AT stabilized backbone.

Plate reader lysis experiments as described in Example 3 were performed and showed that the EcN-SLC containing the various nanobody plasmids expressed the nanobodies (FIG. 12A).

Figure 12B:
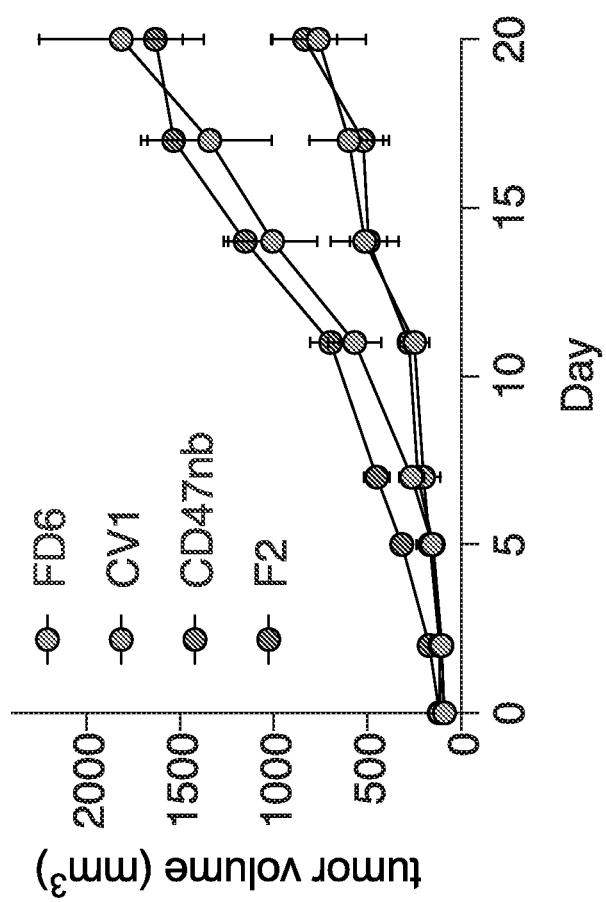
FIG. 12B is a graph of tumor volume in A20 mice receiving intratumoral injections on day 0 and day 7 with EcN-SLC-int-F2 (scrambled nanobody control), EcN-SLC-int-CV1 (high-affinity human SIRPa variant, also binds mCD47), EcN-SLC-int-FD6 (high-affinity human SIRPa variant, also binds mCD47), or EcN-SLC-int-CD47nb (mouse-specific anti-CD47 nanobody) in both tumors. Tumor growth curves. * P<0.001.

Next the therapeutic efficacy of the various EcN-SLCs was evaluated. BALB/c mice (n=7-8 tumors per group) were implanted subcutaneously with $5 \times 10^6$ A20 B cell lymphoma cells on both hind flanks. When tumor volumes were 100-150 mm$^3$, the mice received intratumoral injections on day 0 and day 7 with EcN-SLC-int-F2 (scrambled nanobody control), EcN-SLC-int-CV1 (high-affinity human SIRPa variant, also binds mCD47), EcN-SLC-int-FD6 (high-affinity human SIRPa variant, also binds mCD47), or EcN-SLC-int-CD47nb (mouse-specific anti-CD47 nanobody) in both tumors. As shown in FIG. 12B, EcN-SLC-int-CD47nb and EcN-SLC-int-CV1 reduced tumor growth.

Figure 12C:
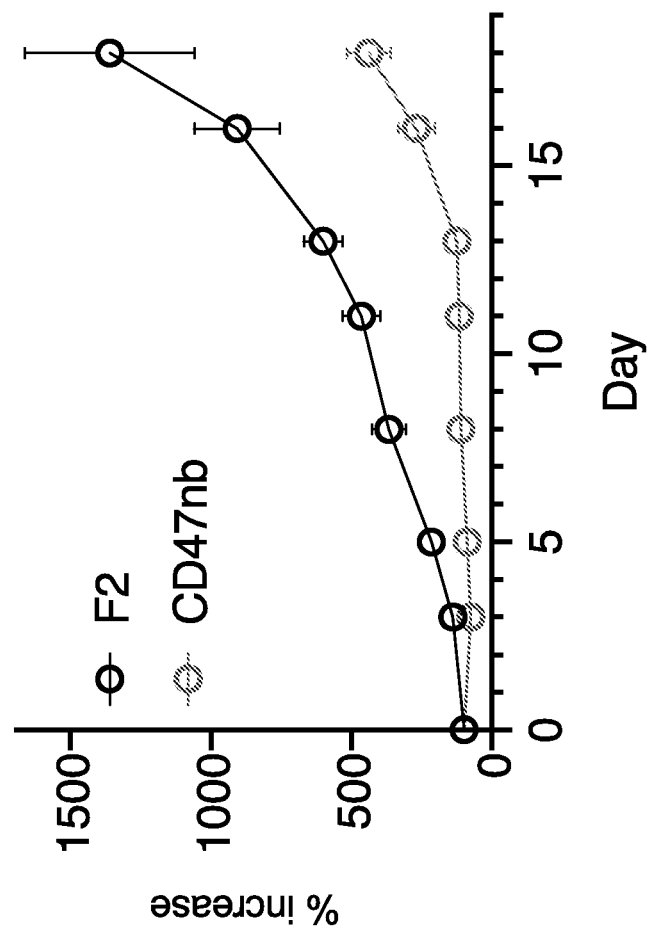
FIG. 12C is a graph of the percent increase of tumor from baseline in CT26 mice receiving intratumoral injections every 3 days with EcN-SLC-int-F2 (scrambled nanobody control), or EcN-SLC-int-CD47nb (mouse-specific anti-CD47 nanobody) in both tumors for a total of 4 doses. % increase of tumor from baseline. ** P<0.0001

The experiments were repeated using CT26 murine colon cancer model. BALB/c mice (n=7-8 tumors per group) were implanted subcutaneously with $10^6$ CT26 colon carcinoma cells on both hind flanks. When tumor volumes were 80-150 mm$^3$, mice received intratumoral injections every 3 days with EcN-SLC-int-F2 (scrambled nanobody control), or EcN-SLC-int-CD47nb (mouse-specific anti-CD47 nanobody) in both tumors for a total of 4 doses. As shown in FIG. 12C, the EcN-SLC-int-CD47nb reduced tumor growth.

These data showed the efficacy of using the integrated SLC with additional therapeutic agents including high affinity variants and nanobodies.

Example 13—Bacteria Containing Chemokine Ligand 16 (CXCL16) as the Deliverable Therapeutic Agent Considering the number of cancers that metastasize to the liver and the adverse prognosis associated with this event, it is hypothesized that local treatment of secondary liver metastases presents a viable and promising strategy to drive intrahepatic priming of antitumor immunity to attack systemically growing lesions. An EcN-SLC strain expressing a soluble variant of human CXCL16 (EcN-SLC-CXCL16) will be engineered to produce a new programmable bacteria producing a soluble variant of human CXCL16. CXCL16 is a chemokine that is predominantly expressed by antigen-presenting dendritic cells (DC) and macrophages of the hematopoietic lineage and functions as both a cell adhesion molecule (in its transmembrane form) or as a soluble chemoattractant when cleaved from the cell surface by the metalloproteinase ADAM10. CXCL16 promotes the infiltration and retention of T cells and macrophages into tumors and suppresses liver metastasis. Notably, the beneficial effects of CXCL16 appear to depend on its local expression—circulating levels are associated with vascular disorders and can promote tumor cell migration and metastatic spread. Elevated levels of CXCL16 are also associated with better prognosis in non-small cell lung cancer and correlate with increased numbers of tumor-infiltrating lymphocytes in colorectal cancer.

Notably, the beneficial effects of CXCL16 appear to depend on its local expression—circulating levels are associated with vascular disorders and can promote tumor cell migration and metastatic spread. Thus, by engineering a probiotic strain that locally releases high levels of CXCL16 within the necrotic core of a growing tumor, its potent pro-inflammatory characteristics can be utilized, while avoiding complications that have traditionally prohibited its use as a systemic cancer therapeutic.

The SLC integrated into the genome of the E. coli Nissle 1917 as described in Examples 1 and 3 is constructed. Next plasmids encoding the soluble extracellular domain of human CXCL16 (Asn49-Pro137) that also activates mouse CXCR6 are constructed similar to the methods described in Examples 1, 2, and 7. The approach using the human CXCL16 for EcN-SLC-CXCL16 permits direct translation of preclinical mouse experiments to future human studies. These constructs are optimized with promoter and retention sequences for stable, high-copy expression in EcN-SLC. These are constructed on a conditional-replication, integration, and modular (CRIM) vector, which can be maintained as a plasmid for in vitro tests, but then conveniently integrated into the genome for stability during preclinical experiments.

To confirm that EcN-SLC-CXCL16 releases soluble chemokine in an SLC-dependent manner, engineered plasmids are expressed in both EcN and EcN-SLC and levels of CXCL16 in pelleted bacteria and overnight stationary phase culture supernatants will be quantified by CXCL16 ELISA and western blot as described in Example 1.

For enhancing the safety profile of EcN-SLC-CXCL16, variants are constructed wherein CXCL16 expression is regulated by luxI promoter elements for AHL-dependent quorum-restricted firing, as well as stable variants wherein the CXCL16 construct has been integrated into the EcN-SLC genome. Confirmed lysis-dependent intermediate and high CXCL16 expressers will be tested for therapeutic efficacy by intratumoral or oral delivery to mice with subcutaneous or hepatic metastases of A20 B cell lymphoma, respectively, as described in Example 7.

The goal of these experiments will be to assess the priming and systemic activity of antitumor T cells following treatment with immunotherapeutic probiotics. Using three different mouse models of experimental hepatic metastasis, the growth of liver metastases and matched subcutaneous tumors are monitored and antitumor T cell responses following oral or intratumoral delivery of the programmable bacteria is quantified. It is hypothesized that treatment with immunotherapeutic probiotic bacteria will promote the regression of colonized metastatic liver lesions and activate abscopal immunity against distant tumor foci.

Further experiment are done to determine the therapeutic efficacy for antitumor immune responses elicited by treatment of primary tumors and hepatic metastases with programmable bacteria delivering CXCL16. Elevated levels of systemically circulating CXCL16 are observed in settings of bacterial sepsis, where it has also been suggested to regulate sepsis-associated inflammatory events that result in liver failure; thus, as with other forms of immunotherapy, systemic administration can lead to numerous, and potentially fatal, side-effects. It is hypothesized that localized delivery of CXCL16 by EcN-SLC within the necrotic core of a growing tumor will promote the infiltration and local priming of tumor antigen—specific T cells without systemic side effects. For this aim, mice receive A20-OVA-Luc B cell lymphoma cells by intravenous injection and A20-OVA cells subcutaneously, seeding the liver and lungs and providing an external subcutaneous tumor expressing ovalbumin as a shared tumor antigen. A similar experimental setup has been used to test systemic abscopal immunity elicited by intra-tumoral treatment of a single lesion (see Examples 7 and 11). When subcutaneous tumors reach approximately 100 mm$^3$, animals receive EcN-SLC-CXCL16 by oral gavage every 3 days for a total of 4 treatments.

Growth of intrahepatic and subcutaneous tumors are monitored by IVIS imaging and caliper measurement, respectively (Example 7). As an alternative approach, in separate experiments, EcN-SLC-CXCL16 is intratumorally injected into subcutaneous tumors to test reciprocal efficacy of subcutaneous priming for the clearance of hepatic metastases.

In addition to monitoring tumor growth, flow cytometric analyses is performed to quantify the infiltration and activity of Ova-specific T cells within colonized liver metastases and distant subcutaneously growing A20-OVA tumors using I-Ad-OVA323-339 MHC tetramers for CD4+ T cells and ex vivo restimulation of CD4+ and CD8+ antitumor T cells using OVA323-339 and A20-Idiotype106-114 (for Kd 68) peptides. Efficacy in two additional tumor models is tested by subcutaneous implantation and hepatic portal vein injection (to seed liver metastases) of B16 melanoma and CT26 colorectal carcinoma in C57BL/6 and BALB/c mice, respectively.

It is expected that robust anti-A20 immunity will be elicited within colonized liver tumors and function to prime responses against distant subcutaneous lesions in an abscopal fashion as seen with the EcN-SLC-CD47nb.

Example 14—Selection of Probiotic Strains for Enhanced Colonization of Liver Metastases Following Oral Delivery One challenge of bacteria therapies is the inherent trade-off between the beneficial immune stimulation generated intra-tumorally and the toxicity associated with the immune response upon systemic delivery. To mitigate toxicity from systemic delivery, genetic attenuations that modify LPS structure and hence recognition have been made, which in turn reduce TNFα response. Although these approaches succeed in reducing immune stimulation for systemic delivery, they inevitably produce strains that have diminished colonization, intra-tumoral immune-stimulation, and overall therapeutic response.

A multitude of bacteria therapy studies have demonstrated the selective colonization of bacteria, either through intravenous, intratumoral, or oral delivery. Probiotic strain, E. coli Nissle 1917 (EcN), was able to efficiently colonize 90% of liver metastases as small as 1 mm when orally delivered.

This advance was derived from the known translocation phenomena observed in probiotics across the GI tract, through which a small fraction of bacteria reaches the portal-vein system and lead to liver tumor colonization. While the specific mechanism for EcN translocation was not studied, general properties including the dose of bacteria, local microbiota, and invasion ability are known factors that affect translocation efficiency.

To improve upon this efficiency, two approaches will be utilized: (1) directed-evolution to enrich for strains with enhanced translocation, and (2) engineering of increased expression of translocation-associated genes. Directed evolution is utilized to serially, orally deliver probiotic bacteria and recover them from liver metastases, selecting for enhanced tumor-targeting strains. RNA-seq and bacteria-cell attachment assays are performed to determine associated mutations that lead to improved colonization of EcN.

To evolve strains, we orally deliver EcN with an integrated luciferase and erythromycin (Er) cassette to mice with liver metastases. The mice are imaged with IVIS to confirm colonization, explant and homogenize tumors, and plate onto Er plates to obtain single colonies of bacteria as described in Example 7. These strains are grown up in cultures, then mixed in equal parts to obtain the inoculum for the subsequent round of colonization. Two additional rounds of oral delivery and isolation are performed, enriching for strains that have most efficiently translocated and colonized liver metastases. From each of the 3 rounds, approximately 30-50 bacteria colonies are be selected for downstream analysis using RNA-seq of bacteria colonies to determine upregulated gene expression.

To compliment this analysis, cell-attachment assays are performed, whereby individual colonies are be co-cultured with endothelial cells, and cancer cells, to observe enhancement of cell-attachment. Additionally, individual colonies are tested for their enhanced efficacy by orally delivering the top 5 candidates to mice with liver metastases at several doses, assessing colonization by IVIS and explanting of livers as described in Example 7. Since previous directed evolution studies have observed rapid selection of efficient strains in vivo, it is expected that the present approach will improve the tumor-targeting abilities of EcN following oral delivery, allowing for reduced dose and improved safety of using the programmable bacteria.

REFERENCES

Advani et al. (2018) CD47 Blockade by Hu5F9-G4 and Rituximab in Non-Hodgkin's Lymphoma. *N Engl J Med* 379:1711-1721.

Armstrong et al. (2002) Immunization with a recombinant adenovirus encoding a lymphoma idiotype: induction of tumor-protective immunity and identification of an idiotype-specific T cell epitope. *J. Immunol.* 168, 3983-3991.

Bannas et al. (2017) Nanobodies and nanobody-based human heavy chain antibodies as antitumor therapeutics. *Frontiers in immunology* 8:1603.

Baumeister et al. (2016) Coinhibitory pathways in immunotherapy for cancer. *Annual review of immunology* 34:539-573.

Contardi et al. (2005) CTLA-4 is constitutively expressed on tumor cells and can trigger apoptosis upon ligand interaction. *International journal of cancer* 117(4):538-550.

Danino et al. (2012) In vivo gene expression dynamics of tumor-targeted bacteria. *ACS synthetic biology* 1(10):465-470.

Danino et al. (2015) Programmable probiotics for detection of cancer in urine. *Science translational medicine* 7(289): 289ra284.

Derman et al. (2012) Alp7R regulates expression of the actin-like protein Alp7A in *Bacillus subtilis*. *J Bacteriol* 194:2715-2724.

Din et al. (2016) Synchronized cycles of bacterial lysis for in vivo delivery. *Nature* 536(7614):81-85.

Dunn et al. (2002) Cancer immunoediting: from immunosurveillance to tumor escape. *Nature immunology* 3:991-998.

Fedorec et al. (2018) Two new plasmid post-segregational killing mechanisms for the implementation of synthetic gene networks in *E. coli. bioRxiv:* 350744.

Fedorec (2014) Mechanisms for Plasmid Maintenance. CoMPLEX, University College London Gerdes et al. (1986) Mechanism of postsegregational killing by the hok gene product of the parB system of plasmid R1 and its homology with the relF gene product of the *E. coli* relB operon. *EMBO J* 5:2023-2029.

Haldimann and Wanner (2001) Conditional-replication, integration, excision, and retrieval plasmid-host systems for gene structure-function studies of bacteria. *Journal of Bacteriology* 183:6384-93.

Hu et al. (2017) Nanobody-based delivery systems for diagnosis and targeted tumor therapy. *Frontiers in immunology* 8:1442.

Huang et al. (2017) Targeting CD47: the achievements and concerns of current studies on cancer immunotherapy. *J Thorac Dis* 9:E168-E174.

Ingram et al. (2017) Localized CD47 blockade enhances immunotherapy for murine melanoma. *Proc Natl Acad Sci USA* 114:10184-10189.

Kauder et al. (2018) ALX148 blocks CD47 and enhances innate and adaptive antitumor immunity with a favorable safety profile. *PloS one* 13:e0201832.

Kim et al. (2014) Eradication of metastatic mouse cancers resistant to immune checkpoint blockade by suppression of myeloid-derived cells. *Journal for immunotherapy of cancer* 2(3):P267.

Kong et al. (2007) LPS-induced down-regulation of signal regulatory protein {alpha} contributes Lee and Jeong (2015) Challenges to production of antibodies in bacteria and yeast. *Journal of bioscience and bioengineering* 120(5):483-490.

Liu et al. (2015) CD47 blockade triggers T cell-mediated destruction of immunogenic tumors. *Nat Med* 21:1209-1215.

Majeti et al. (2009) CD47 is an adverse prognostic factor and therapeutic antibody target on human acute myeloid leukemia stem cells. *Cell* 138:286-299.

Murphy and Weaver (2016) *Janeway's immunobiology*. 9th edition. edn, (Garland Science/Taylor & Francis Group, LLC).

Naidoo et al. (2015) Toxicities of the anti-PD-1 and anti-PD-L1 immune checkpoint antibodies. *Annals of Oncology* 26:2375-2391.

Redelman-Sidi et al. (2014) The mechanism of action of BCG therapy for bladder cancer—a current perspective. *Nature Reviews Urology* 11(3):153.

Sandage et al. (2017) *Abstract* 2619: Combination of ECP1014 and anti-PD-L1 reduces tumor growth in the CT26 murine colon carcinoma of a cold tumor. *Cancer research* 77(13 supplement): 2619.

Sagiv-Barfi et al. (2015) Therapeutic antitumor immunity by checkpoint blockade is enhanced by ibrutinib, an inhibitor of both BTK and ITK. *Proc Natl Acad Sci USA* 201500712.

Secher et al. (2017) Oral administration of the probiotic strain *Escherichia coli* Nissle 1917 reduces susceptibility to neuroinflammation and repairs experimental autoimmune encephalomyelitis-induced intestinal barrier dysfunction. *Frontiers in immunology* 8:1096.

Skinner et al. (2013) Measuring mRNA copy number in individual *Escherichia coli* cells using single-molecule fluorescent in situ hybridization. *Nat Protoc* 8, 1100-1113.

Sockolosky et al. (2016) Durable antitumor responses to CD47 blockade require adaptive immune stimulation. *Proc Natl Acad Sci USA* 113, E2646-2654.

Swann and Smyth (2007) Immune surveillance of tumors. *Journal of Clinical Investigation* 117:1137.

Weiskopf et al. (2013) Engineered SIRPα Variants as Immunotherapeutic Adjuvants to Anticancer Antibodies. *Science* 341:88-91.

Willingham et al. (2012) The CD47-signal regulatory protein alpha (SIRPa) interaction is a therapeutic target for human solid tumors. *Proc Natl Acad Sci USA* 109:6662-6667.

INCORPORATION BY REFERENCE

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

The invention claimed is:

1. A programmable bacterium, comprising:
   a. at least one synchronized lysis circuit, contained in a single operon and integrated into the genome of the bacterium;
   b. at least one plasmid comprising a nucleic acid sequence which encodes a therapeutic agent, wherein the at least one plasmid is a high copy plasmid,
   wherein the programmable bacterium delivers the therapeutic agent to a tumor and activates an immune response against the tumor, and
   wherein the at least one synchronized lysis circuit comprises a nucleic acid encoding a quorum-sensing gene, a nucleic acid encoding a lysis gene, a promoter, and a terminator contained on a single operon.

2. The programmable bacterium of claim 1, wherein the bacterium is *E. coli*.

3. The programmable bacterium of claim 1, wherein the bacterium is *E. coli* Nissle 1917 bacteria.

4. The programmable bacterium of claim 1, wherein the at least one synchronized lysis circuit comprises a plux promoter, a nucleic acid encoding a LuxR gene, a nucleic acid encoding a luxI gene, a nucleic acid encoding the lysis gene E from bacteriophage ΦXΓ74, and a terminator contained on a single operon.

5. The programmable bacterium of claim 1, wherein the therapeutic agent is chosen from the group consisting of nanobodies to checkpoint inhibitors and over-expressed markers in cancers, toxins, tumor antigens, cytokines, and chemokines.

6. The programmable bacterium of claim 5, wherein the therapeutic agent is a nanobody to checkpoint inhibitors and is chosen from the group consisting of CTLA-4 and PDL1.

7. The programmable bacterium of claim 5, wherein the therapeutic agent is a nanobody to an over-expressed marker in cancer and is chosen from the group consisting of CD47 and SIRPα.

8. A composition comprising the programmable bacterium of claim 1.

9. The composition of claim 8, further comprising a pharmaceutically acceptable carrier.

10. A method of treating cancer in a subject in need thereof comprising administering to the subject a therapeutically effective amount of the programmable bacterium of claim 1.

11. The method of claim 10, wherein a therapeutically effective amount a first and a second programmable bacterium is administered to the subject, wherein the first and the second programmable bacterium differ in one or more of the following traits: strain of bacterium, and the therapeutic agent.

12. The method of claim 11, wherein the cancer to be treated is chosen from the group consisting of primary cancer and metastatic cancer.

13. The method of claim 11, wherein the cancer to be treated is chosen from the group consisting of include breast, melanoma, renal cancer, prostate cancer, pancreatic adenocarcinoma, colon cancer (CRC), lung cancer, esophageal cancer, squamous cell carcinoma of the head and neck, liver cancer, ovarian cancer, cervical cancer, thyroid cancer, glioblastoma, and glioma.

14. A method of treating cancer in a subject in need thereof comprising administering to the subject a therapeutically effective amount of the composition of claim 8.

15. The method of treating cancer of claim 10, wherein the programmable bacterium is administered by a method chosen from the group consisting of intratumoral, oral, intravenous, intraperitoneal, or subcutaneous administration.

16. The method of treating cancer of claim 1, wherein a tumor which is reduced or eliminated does not contain a programmable bacterium.

17. A method of inducing systemic adaptive immunity in a subject with cancer, comprising administering the programmable bacterium of claim 10, wherein the administration of the programmable bacterium reduces or limits the growth of untreated tumors.

18. A method of inducing systemic adaptive immunity in a subject with cancer, comprising administering the composition of claim 8, wherein the administration of the programmable bacterium reduces or limits the growth of untreated tumors.

* * * * *